(12) United States Patent
Nishimiya et al.

(10) Patent No.: US 11,060,108 B2
(45) Date of Patent: Jul. 13, 2021

(54) DNA ELEMENT HAVING THE ACTIVITY OF ENHANCING FOREIGN GENE EXPRESSION

(71) Applicant: Daiichi Sankyo Company, Limited, Tokyo (JP)

(72) Inventors: Daisuke Nishimiya, Tokyo (JP); Tatsuya Inoue, Tokyo (JP)

(73) Assignee: Daiichi Sankyo Company, Limited, Tokyo (JP)

(*) Notice: Subject to any disclaimer, the term of this patent is extended or adjusted under 35 U.S.C. 154(b) by 0 days.

(21) Appl. No.: 16/523,547

(22) Filed: Jul. 26, 2019

(65) Prior Publication Data
US 2019/0345515 A1 Nov. 14, 2019

Related U.S. Application Data

(60) Division of application No. 15/162,294, filed on May 23, 2016, now Pat. No. 10,407,694, which is a division of application No. 13/728,809, filed on Dec. 27, 2012, now Pat. No. 9,371,543, which is a continuation of application No. PCT/JP2011/065916, filed on Jul. 6, 2011.

(30) Foreign Application Priority Data

Jul. 7, 2010 (JP) .................................. 2010-154782

(51) Int. Cl.
*C12N 15/85* (2006.01)
*C07K 16/00* (2006.01)
*C12P 21/00* (2006.01)

(52) U.S. Cl.
CPC .............. *C12N 15/85* (2013.01); *C07K 16/00* (2013.01); *C12P 21/00* (2013.01); *C07K 2317/14* (2013.01); *C07K 2317/24* (2013.01); *C07K 2317/51* (2013.01); *C07K 2317/515* (2013.01); *C12N 2800/107* (2013.01); *C12N 2830/46* (2013.01)

(58) Field of Classification Search
CPC .............. C12N 15/85; C12N 2800/107; C12N 2830/46; C12N 15/113; C12N 2310/10; C07K 16/00; C07K 2317/14; C07K 2317/24; C07K 2317/51; C07K 2317/515; C12P 21/00
See application file for complete search history.

(56) References Cited

U.S. PATENT DOCUMENTS

2007/0161003 A1 7/2007 Morris et al.

FOREIGN PATENT DOCUMENTS

| WO | 89/07644 A1 | 8/1989 |
| WO | 2009/118137 A1 | 10/2009 |

OTHER PUBLICATIONS

Alberts, B., et al., "Molecular Cell Biology," Peach Publishers, Moscow, 1994, p. 129.
Bell, A.C., et al., "Insulators and Boundaries: Versatile Regulatory Elements in the Eukaryotic Genome," Science 291(5503):447-450, Jan. 2001.
Birren, B., "*Homo sapiens* Chromosome 11, Clone RP11-702F3, Complete Sequence," Nucleic Acid Sequence Accession No. AC024475. 15, submitted to GenBank on Feb. 28, 2000, <http://www.ncbi.nlm.nih.gov/nuccore/AC024475.15> [retrieved Apr. 5, 2016], 54 pages.
Database Genbank: *Homo sapiens* all assemblies "*Homo sapiens* chromosome 15 genomic scaffold, GRCh38 alternate locus group ALT_REF_LOCI_1 HSCHR15_5_CTG8," NCBI Reference Sequence: NT_187606.1, Feb. 3, 2014, <http://www.ncbi.nlm.nih.gov/nuccore/568815403?report=genbank&to=43088> [retrieved Aug. 21, 2014], 16 pages.
"European Bioinformatics Institute, European Nucleotide Archive (ENA)," Sequence No. AC010724.6, "*Homo sapiens* BAC Clone RP11-152F13 From 15, Complete Sequence," Database ENA [Online], Sep. 23, 1999, <http://www.ebi.ac.uk/ena/data/view/AC010724> [retrieved Feb. 22, 2013], 6 pages.
"European Bioinformatics Institute, European Nucleotide Archive (ENA)," Sequence No. CZ458076.1, "MCF745I07TF Human MCF7 Breast Cancer Cell Line Library (MCF7_1) *Homo sapiens* Genomic Clone MCF7_45I07, Genomic Survey Sequence," Database ENA [Online], Oct. 21, 2005, <http://www.ebi.ac.uk/ena/data/view/CZ458076> [retrieved Feb. 22, 2013], 3 pages.
Girod, P.A., et al., "Genome-Wide Prediction of Matrix Attachment Regions That Increase Gene Expression in Mammalian Cells," Nature Methods 4(9):747-753, Sep. 2007.
Gorman, C., et al., "Use of MAR Elements to Increase the Production of Recombinant Proteins," in M. Al-Rubeai (ed.), "Cell Engineering," vol. 6, "Cell Line Development," Springer Science+Business Media, Berlin, 2009, pp. 1-32.
Harrison, E., "Human DNA Sequence From Clone RP6-137J22 on Chromosome 1," Nucleic Acid Sequence Accession No. BX248398. 9, submitted to European Nucleotide Archive on Jan. 13, 2009, <http://www.ebi.ac.uk/ena/data/view/BX248398&display=text> [retrieved Apr. 5, 2016], 38 pages.
Hattori, M., et al., "*Homo sapiens* Genomic DNA, Chromosome 11q, Clone RP11-643G5, Complete Sequence," Nucleic Acid Sequence Accession No. AP003400.2, submitted to GenBank on Mar. 8, 2001, <http://www.ncbi.nlm.nih.gov/nuccore/15320508> [retrieved Apr. 5, 2016], 31 pages.
"*Homo sapiens* Genomic DNA, Chromosome 11q, Clone:RP11-643G5," Database EMBL Accession No. AP003400, Mar. 19, 2001, retrieved from EB Accession No. EM_STD:AP003400, <http://ibis.internal.epo.org/exam/dbfetch.jsp?id=EM_STD:AP003400>, [retrieved Nov. 28, 2013], 29 pages.

(Continued)

*Primary Examiner* — Paul J Holland
(74) *Attorney, Agent, or Firm* — Christensen O'Connor Johnson Kindness PLLC

(57) ABSTRACT

A method for stably achieving high expression of a foreign gene in mammalian cells using a novel DNA element is disclosed. More specifically, the present application discloses a DNA element which enhances the activation of transcription by changing the chromatin structure around a gene locus into which a foreign gene expression unit has been introduced.

22 Claims, 14 Drawing Sheets

Specification includes a Sequence Listing.

(56) References Cited

OTHER PUBLICATIONS

Kwaks, T.H., and A.P. Otte, "Employing Epigenetics to Augment the Expression of Therapeutic Proteins in Mammalian Cells," Trends in Biotechnology 24(3):137-142, Mar. 2006.

Li, M., "Advanced Molecular Genetics," Science Press, Beijing, 2004, pp. 366-367.

Li, Q., et al., "Locus Control Regions," Blood 100(9):3077-3086, Nov. 2002.

Nakatani, Y., "Histone Acetylases—Versatile Players," Genes to Cells 6(2):79-86, Feb. 2001.

Otte, A.P., et al., "Various Expression-Augmenting DNA Elements Benefit From STAR-Select, a Novel High Stringency Selection System for Protein Expression," Biotechnology Progress 23(4):801-807, Jul.-Aug. 2007.

Shen, G., et al., "Molecular Biology Toward a Era of Postgenomics," Zhejiang Education Publishing House, 2005, p. 113.

Volik, S., et al., "Decoding the Fine-Scale Structure of a Breast Cancer Genome and Transcriptome," Genome Research 16(3):394-404, Mar. 2006.

Waterston, R.H., "*Homo sapiens* BAC Clone RP11-152F13 From 15, Complete Sequence," Nucleic Acid Sequence Accession No. AC010724.6, submitted to GenBank on Sep. 21, 1999, <http://www.ncbi.nlm.nih.gov/nuccore/AC010724> [retrievedApr. 5, 2016], 65 pages; Sulston, J.E., and R. Waterston, "Toward a Complete Human Genome Sequence," Genome Research (11):1097-1108, Nov. 1998.

Waterston, R.H., "*Homo sapiens* BAC Clone RP11-115A14 From 4, Complete Sequence," Nucleic Acid Sequence Accession No. AC093770.4, submitted to GenBank on Sep. 10, 2001, <http://www.ncbi.nlm.nih.gov/nuccore/AC093770> [retrieved Apr. 5, 2016], 32 pages.

Williams, S., et al., "CpG-Island Fragments From the HNRPA2B1/CBX3 Genomic Locus Reduce Silencing and Enhance Transgene Expression From the hCMV Promoter/Enhancer in Mammalian Cells," BMC Biotechnology 5:17, Jun. 2005, 9 pages.

Wurm, F.M., "Production of Recombinant Protein Therapeutics in Cultivated Mammalian Cells," Nature Biotechnology 22(11):1393-1398, Nov. 2004.

International Search Report dated Feb. 21, 2012, issued in corresponding International Application No. PCT/JP2011/065916, filed Jul. 6, 2011, 7 pages.

International Preliminary Report on Patentability dated Jan. 8, 2013, issued in corresponding International Application No. PCT/JP2011/065916, filed Jul. 6, 2011, 11 pages.

Extended European Search Report dated Dec. 16, 2013, issued in corresponding European Application No. 13 186 031.4, filed Sep. 25, 2013, 9 pages.

State Intellectual Property Office of P.R. China (SIPO) First Office Action, dated Nov. 4, 2013, issued in corresponding Chinese Application No. 201180043099.8, filed Jul. 6, 2011, 4 pages.

Written Opinion dated May 16, 2014, issued in corresponding Singapore Application No. 201209433-0, filed Jul. 6, 2011, 8 pages.

Russian Office Action dated Dec. 9, 2015, issued in corresponding Russian Application No. 2013104989/10 (007422), filed Jul. 6, 2011, 9 pages.

Reexamination Notice dated Jul. 19, 2017, in CN Application No. 201410141682.8, filed Jul. 6, 2011, 11 pages.

First Office Action dated May 3, 2018, issued in CN Application No. 2016102823375, filed Jul. 6, 2011, 10 pages.

Extended European Search Report dated Apr. 26, 2016, in EP Application No. 15188915.1, filed Jul. 6, 2011, 9 pages.

| ID | START LOCATION | END LOCATION | LENGTH (BP) |
|---|---|---|---|
| *A2* | *80966429* | *80974878* | *8450* |
| *A2-1* | *80966429* | *80969428* | *3000* |
| *A2-2* | *80969229* | *80972228* | *3000* |
| *A2-3* | *80971829* | *80974878* | *3050* |
| *A2-4* | *80967129* | *80969128* | *2000* |
| *A2-5* | *80967129* | *80968628* | *1500* |
| *A2-6* | *80967129* | *80970128* | *3000* |
| *A2-7* | *80968429* | *80971428* | *3000* |
| *A2-8* | *80970429* | *80973428* | *3000* |
| *A2-9* | *80966429* | *80970128* | *3700* |
| *A2-10* | *80968429* | *80972228* | *3800* |
| *A2-11* | *80969229* | *80973428* | *4200* |
| *A2-12* | *80967129* | *80972228* | *5100* |
| *A2-13* | *80968429* | *80973428* | *5000* |
| *A2-14* | *80969229* | *80974878* | *5650* |
| *A2-15* | *80966429* | *80972228* | *5800* |
| *A2-16* | *80967129* | *80973428* | *6300* |
| *A2-17* | *80968429* | *80974878* | *6450* |

*FIG. 7.*

| ID | START LOCATION | END LOCATION | LENGTH (BP) |
|---|---|---|---|
| A7 | 88992123 | 89000542 | 8420 |
| A7-1 | 88992723 | 88995722 | 3000 |
| A7-2 | 88995723 | 89000542 | 4820 |
| A7-3 | 88997523 | 89000542 | 3020 |
| A7-4 | 88995523 | 88998522 | 3000 |
| A7-5 | 88993623 | 88996622 | 3000 |
| A7-6 | 88996523 | 88999522 | 3000 |
| A7-7 | 88994523 | 88997522 | 3000 |
| A7-8 | 88992123 | 88995722 | 3600 |
| A7-9 | 88993623 | 88997522 | 3900 |
| A7-10 | 88994523 | 88998522 | 4000 |
| A7-11 | 88995523 | 88999522 | 4000 |
| A7-12 | 88996523 | 89000542 | 4020 |
| A7-13 | 88992123 | 88997522 | 5400 |
| A7-14 | 88993623 | 88998522 | 4900 |
| A7-15 | 88994523 | 88999522 | 5000 |
| A7-16 | 88995523 | 89000542 | 5020 |
| A7-17 | 88992123 | 88998522 | 6400 |
| A7-18 | 88993623 | 88999522 | 5900 |

FIG. 9.

| ID | START LOCATION | END LOCATION | LENGTH (BP) |
|---|---|---|---|
| A18 | 111275976 | 111284450 | 8475 |
| A18-1 | 111275976 | 111281015 | 5040 |
| A18-2 | 111276976 | 111281977 | 5002 |
| A18-3 | 111277976 | 111282975 | 5000 |
| A18-4 | 111278975 | 111282975 | 4001 |

| ID | START LOCATION | END LOCATION | LENGTH (BP) |
|---|---|---|---|
| B5 | 143034684 | 143043084 | 8401 |
| B5-1 | 143034684 | 143038684 | 4001 |
| B5-2 | 143034684 | 143037883 | 3200 |
| B5-3 | 143037174 | 143040284 | 3111 |
| B5-4 | 143040056 | 143043084 | 3029 |
| B5-5 | 143035584 | 143038684 | 3101 |
| B5-6 | 143038684 | 143041683 | 3000 |

| ID | START LOCATION | END LOCATION | LENGTH (BP) |
|---|---|---|---|
| C14 | 46089056 | 46097482 | 8427 |
| C14-1 | 46090015 | 46093070 | 3056 |
| C14-2 | 46091042 | 46094069 | 3028 |
| C14-3 | 46093075 | 46096174 | 3100 |
| C14-4 | 46090015 | 46097196 | 7182 |
| C14-5 | 46090015 | 46095066 | 5052 |
| C14-6 | 46093994 | 46097196 | 3203 |
| C14-7 | 46090015 | 46094069 | 4055 |
| C14-8 | 46092049 | 46096174 | 4126 |
| C14-9 | 46093075 | 46097196 | 4122 |
| C14-10 | 46089056 | 46094069 | 5014 |
| C14-11 | 46091042 | 46096174 | 5133 |
| C14-12 | 46092049 | 46097196 | 5148 |
| C14-13 | 46090015 | 46096174 | 6160 |
| C14-14 | 46091042 | 46097196 | 6155 |

THE START AND END POINTS ON THE BASIS OF THE FULL LENGTH SEQUENCE OF THE DNA ELEMENT A2

| A2 | START POINT | END POINT |
|---|---|---|
| A2 | 1 | 8450 |
| A2-1 | 1 | 3000 |
| A2-2 | 2801 | 5800 |
| A2-3 | 5401 | 8450 |
| A2-4 | 701 | 2700 |
| A2-5 | 701 | 2200 |
| A2-6 | 701 | 3700 |
| A2-7 | 2001 | 5000 |
| A2-8 | 4001 | 7000 |
| A2-9 | 1 | 3700 |
| A2-10 | 2001 | 5800 |
| A2-11 | 2801 | 7000 |
| A2-12 | 701 | 5800 |
| A2-13 | 2001 | 7000 |
| A2-14 | 2801 | 8450 |
| A2-15 | 1 | 5800 |
| A2-16 | 701 | 7000 |
| A2-17 | 2001 | 8450 |

THE START AND END POINTS ON THE BASIS OF THE FULL LENGTH SEQUENCE OF THE DNA ELEMENT A7

| A7 | START POINT | END POINT |
|---|---|---|
| A7 | 1 | 8420 |
| A7-1 | 601 | 3600 |
| A7-2 | 3601 | 8420 |
| A7-3 | 5401 | 8420 |
| A7-4 | 3401 | 6400 |
| A7-5 | 1501 | 4500 |
| A7-6 | 4401 | 7400 |
| A7-7 | 2401 | 5400 |
| A7-8 | 1 | 3600 |
| A7-9 | 1501 | 5400 |
| A7-10 | 2401 | 6400 |
| A7-11 | 3401 | 7400 |
| A7-12 | 4401 | 8420 |
| A7-13 | 1 | 5400 |
| A7-14 | 1501 | 6400 |
| A7-15 | 2401 | 7400 |
| A7-16 | 3401 | 8420 |
| A7-17 | 1 | 6400 |
| A7-18 | 1501 | 7400 |

THE START AND END POINTS ON THE BASIS OF THE FULL LENGTH SEQUENCE OF THE DNA ELEMENT A18

| A18 | START POINT | END POINT |
|---|---|---|
| A18 | 1 | 8475 |
| A18-1 | 1 | 5040 |
| A18-2 | 1001 | 6002 |
| A18-3 | 2001 | 7000 |
| A18-4 | 3000 | 7000 |

FIG. 19.

| THE START AND END POINTS ON THE BASIS OF THE FULL LENGTH SEQUENCE OF THE DNA ELEMENT B5 | | |
|---|---|---|
| | START POINT | END POINT |
| B5 | 1 | 8401 |
| B5-1 | 1 | 4001 |
| B5-2 | 1 | 3200 |
| B5-3 | 2491 | 5601 |
| B5-4 | 5373 | 8401 |
| B5-5 | 901 | 4001 |
| B5-6 | 4001 | 7000 |

| THE START AND END POINTS ON THE BASIS OF THE FULL LENGTH SEQUENCE OF THE DNA ELEMENT C14 | | |
|---|---|---|
| | START POINT | END POINT |
| C14 | 1 | 8427 |
| C14-1 | 960 | 4015 |
| C14-2 | 1987 | 5014 |
| C14-3 | 4020 | 7119 |
| C14-4 | 960 | 8141 |
| C14-5 | 960 | 6011 |
| C14-6 | 4939 | 8141 |
| C14-7 | 960 | 5014 |
| C14-8 | 2994 | 7119 |
| C14-9 | 4020 | 8141 |
| C14-10 | 1 | 5014 |
| C14-11 | 1987 | 7119 |
| C14-12 | 2994 | 8141 |
| C14-13 | 960 | 7119 |
| C14-14 | 1987 | 8141 | ps of uniformly increasing gene expression has not yet been

DNA ELEMENT HAVING THE ACTIVITY OF ENHANCING FOREIGN GENE EXPRESSION

CROSS-REFERENCES TO RELATED APPLICATIONS

This application is a division of U.S. patent application Ser. No. 15/162,294, filed May 23, 2016, which is a division of U.S. patent application Ser. No. 13/728,809, filed Dec. 27, 2012, now U.S. Pat. No. 9,371,543, which is a continuation of International Application No. PCT/JP2011/065916, filed Jul. 6, 2011, which claims the benefit of Japanese Patent Application 2010-154782, filed Jul. 7, 2010, the disclosures of which are incorporated by reference herein.

STATEMENT REGARDING SEQUENCE LISTING

The sequence listing associated with this application is provided in text format in lieu of a paper copy and is hereby incorporated by reference into the specification. The name of the text file containing the sequence listing is 69258_Seq_Final_2019-07-26.txt. The text file is 79.6 KB; was created on Jul. 26, 2019; and is being submitted via EFS-Web with the filing of the specification.

TECHNICAL FIELD

The present invention relates to a transformed mammalian host cell whose ability to secrete a foreign protein has been enhanced by using a foreign gene expression vector having a DNA element and a method for producing the foreign protein using the host cell.

BACKGROUND ART

Due to the development of genetic recombination techniques, the market for protein pharmaceutical products such as therapeutic proteins and antibody drugs has rapidly expanded. In particular, antibody drugs have high specificity and do not cause an adverse immunoreaction even if they are administered to the human body, and therefore, the development thereof has been actively performed.

As a host cell in which a protein pharmaceutical typified by an antibody drug is produced, a microorganism, a yeast, an insect, an animal or plant cell, a transgenic animal or plant cell, or the like can be used. In order for the protein pharmaceutical to have biological activity or immunogenicity, post-translational modification such as folding or glycosylation is essential, and therefore a microorganism with which complicated post-translational modification cannot be performed or a plant having a different glycan structure is not suitable as a host cell operating as a bioreactor. The use of a cultured mammalian cell such as a CHO cell which is from a species closely related to humans is currently standard considering that such a cell has a glycan structure similar to that of humans and is safe, and post-translational modification can be performed using such a cell.

In cases where a cultured mammalian cell is used as a host cell, there are the problems that the growth rate is low, the productivity is low, the cost is high, etc., as compared with a microorganism or the like (see Non-Patent Document 1). In addition, in order to use a protein pharmaceutical product in a clinical trial, it is necessary to administer a large amount of the product. Therefore, the lack of production ability thereof is also a worldwide problem. Accordingly, in order to improve the productivity of a foreign gene in a cultured mammalian cell, a lot of studies of promoters, enhancers, drug selection markers, gene amplification and culturing engineering techniques, and the like have been performed so far. However, the current situation is that a system capable of uniformly increasing gene expression has not yet been established. As one of the causes of the low productivity of a foreign protein, a "position effect" is considered (see Non-Patent Document 2). When a foreign gene is introduced into a host cell, it is randomly integrated into the host chromosomal genome, and the transcription of the foreign gene is greatly affected by DNA around the region where the foreign gene has been integrated. A position effect is affected by factors such as the insertion site, copy number, structure, etc. of the foreign gene, however, it is very difficult to control the insertion site in the chromosome.

In order to solve the problem, regulatory polynucleotide sequences (also known as DNA elements) such as a locus control region (LCR), a scaffold/matrix attachment region (S/MAR), an insulator, a ubiquitous chromatin opening element (UCOE), and an anti-repressor (STAR element) have recently been identified (see Non-Patent Documents 3 to 6). A LCR is not required to open the chromatin structure at an endogenous gene locus. However, a LCR is a transcription regulatory element having an ability to open the chromatin structure around the DNA where the foreign gene has been integrated and to remodel a wide range of chromatin when it is used along with a foreign gene expression unit, and is said to require an AT-rich region (see Non-Patent Document 7).

The above-mentioned DNA element typified by LCR is often used in combination with a promoter, and it is known that in cases where a DNA element is used in combination with a promoter, the expression level of a foreign gene is increased as compared with cases where only the promoter is used. However, very few types of DNA elements have been reported so far, and the various mechanisms contributing to the enhancement of foreign gene expression are different from one another. Further, even if a DNA element and a promoter are used in combination, sufficient amounts of a therapeutic protein under the control of the DNA element and the promoter are not produced. Therefore, it cannot be said that sufficient knowledge of a DNA element capable of increasing the productivity of a foreign protein has been obtained.

Accordingly, an object of the invention is to provide a method for increasing the production of a foreign protein to be used in a protein pharmaceutical product using a DNA element having high activity in enhancing foreign gene expression in a host cell such as a cultured mammalian cell.

CITATION LIST

Non Patent Literature

NPL 1: Florian M. Wurm. (2004) Production of recombinant protein therapeutics in cultivated mammalian cells. Nat. Biotechnol. 22 (11): 1393-1398

NPL 2: Ted H. J. Kwaks and Arie P. Otte. (2006) Employing epigenetics to augment the expression of therapeutic proteins in mammalian cells. TRENDS in Biotechnol. 24(3): 137-142

NPL 3: Pierre-Alain Girod, Duc-Quang Nguyen. et al. (2007) Genome-wide prediction of matrix attachment regions that increase gene expression in mammalian cells. Nat. Methods 4(9):747-753

NPL 4: Adam C. Bell, Adam G. West, Gary Felsenfeld (2001) Insulators and Boundaries: Versatile Regulatory Elements in the Eukaryotic Genome. Science 291:447-450

NPL 5: Steven Williams, Tracey Mustoe. et al. (2005) CpG-island fragments from the HNRPA2B1/CBX3 genomic locus reduce silencing and enhance transgene expression from the hCMV promoter/enhancer in mammalian cells. BMC Biotechnol. 5(17):1-9

NPL 6: Arie P. Otte, Ted H. J. Kwaks. et al. (2007) Various Expression-Augmenting DNA Elements Benefit from STAR-Select, a Novel High Stringency Selection System for Protein Expression. Biotechnol. Prog. 23:801-807

NPL 7: Qiliang Li, Kenneth R. Peterson, Xiangdong Fang, and George Stamatoyannopoulos, (2002) Locus control regions. Blood 100(9):3077-3086

SUMMARY OF INVENTION

Technical Problems

As described above, there are still not many types of DNA elements which are regulatory polynucleotide sequences, and, further, there are very few DNA elements among them that are highly effective in enhancing foreign gene expression. An object of the invention is to provide a method for stably achieving high expression in a mammalian cell using a DNA element which enhances the activation of transcription by being accompanied by a change in chromatin structure around a gene locus into which a foreign gene expression unit has been introduced, etc.

Solution to Problem

The present inventors made intensive studies in order to solve the above problems, and as a result, they found that the productivity and secretion of a foreign protein which is to be expressed can be improved by using one or more specific types of DNA elements in a cultured mammalian cell, and thus, completed the invention.

That is, the invention includes the following inventions.

(1) A polynucleotide consisting of a polynucleotide sequence represented by SEQ ID NO:1 in the Sequence Listing.

(2) A polynucleotide consisting of a polynucleotide sequence represented by SEQ ID NO:2 in the Sequence Listing.

(3) A polynucleotide consisting of a polynucleotide sequence represented by SEQ ID NO:3 in the Sequence Listing.

(4) A polynucleotide consisting of a polynucleotide sequence represented by SEQ ID NO:4 in the Sequence Listing.

(5) A polynucleotide consisting of a polynucleotide sequence represented by SEQ ID NO:5 in the Sequence Listing.

(6) A polynucleotide comprising at least 3000 consecutive nucleotides of a polynucleotide sequence represented by any one of SEQ ID NOS:1 to 5 in the Sequence Listing.

(7) A polynucleotide comprising at least 2000 consecutive nucleotides of a polynucleotide sequence represented by any one of SEQ ID NOS:1 to 5 in the Sequence Listing.

(8) A polynucleotide comprising at least 1500 consecutive nucleotides of a polynucleotide sequence represented by any one of SEQ ID NOS:1 to 5 in the Sequence Listing.

(9) A polynucleotide consisting of a polynucleotide sequence having a homology of 95% or more to the polynucleotide sequence of the polynucleotide according to any one of (1) to (8).

(10) A polynucleotide consisting of a polynucleotide sequence having a homology of 99% or more to the polynucleotide sequence of the polynucleotide according to any one of (1) to (8).

(11) A polynucleotide consisting of a polynucleotide sequence containing two or more sequences of the polynucleotide sequence of the polynucleotide according to any one of (1) to (10).

(12) A polynucleotide consisting of two or more types of polynucleotides selected from the polynucleotides according to any one of (1) to (10).

(13) A foreign gene expression vector comprising the polynucleotide sequence of a polynucleotide according to any one of (1) to (12).

(14) The foreign gene expression vector according to (13), wherein the protein encoded by the foreign gene is a multimeric protein.

(15) The foreign gene expression vector according to (14), wherein the protein encoded by the foreign gene is a hetero-multimeric protein.

(16) The foreign gene expression vector according to (15), wherein the protein encoded by the foreign gene is an antibody or a functional fragment thereof.

(17) A transformed cell into which the foreign gene expression vector according to any one of (13) to (16) has been introduced.

(18) The transformed cell according to (17), wherein the cell is a cultured cell derived from a mammal.

(19) The transformed cell according to (18), wherein the cultured cell derived from a mammal is a cell selected from the group consisting of COS-1 cells, 293 cells, and CHO cells.

(20) The transformed cell according to any one of (17) to (18), wherein the protein encoded by the foreign gene is a multimeric protein.

(21) The transformed cell according to (20), wherein the protein encoded by the foreign gene is a hetero-multimeric protein.

(22) The transformed cell according to (21), wherein the protein encoded by the foreign gene is an antibody or a functional fragment thereof.

(23) A method for producing a protein characterized by comprising culturing the transformed cell according to any one of (17) to (22) and obtaining the protein encoded by the foreign gene from the resulting culture product.

(24) A method for enhancing foreign gene expression in a transformed cell into which a foreign gene or a foreign gene expression vector has been introduced, characterized by using a polynucleotide according to any one of (1) to (12) or a foreign gene expression vector according to any one of (13) to (16).

(25) Use of the polynucleotide according to any one of (1) to (12) for enhancing foreign gene expression in a transformed cell.

Advantageous Effects of Invention

According to the invention, by introducing a foreign gene expression vector using a DNA element into a mammalian host cell, the expression of a foreign gene for a therapeutic protein, an antibody, or the like can be significantly enhanced.

BRIEF DESCRIPTION OF DRAWINGS

FIG. 7 is a table showing the sequence lengths of DNA element A2 and related sequences.

FIG. 8A (A2-1-A2-8), FIG. 8B (A2-9-A2-11), and FIG. 8C (A2-12-A2-17). The effects of DNA element A2 and related sequences on enhancement of expression were confirmed.

FIG. 9 is a table showing the sequence lengths of DNA element A7 and related sequences.

FIG. 10A (A7-1-A7-7), FIG. 10B (A7-8-A7-12), and FIG. 10C (A7-13-A7-18). The effects of DNA element A7 and related sequences on enhancement of expression were confirmed.

FIG. 15 is a table showing the sequence lengths of DNA element C14 and related sequences.

FIG. 16A (C14-1-C14-6), FIG. 16B (C14-7-C14-9), and FIG. 16C (C14-10-C14-14). The effects of DNA element C14 and related sequences on enhancement of expression were confirmed.

FIG. 18 is a view showing nucleotides at the starting and end points on the basis of the full-length sequence of a DNA element A2, A7, or A18.

FIG. 19 is a view showing nucleotides at the starting and end points on the basis of the full-length sequence of a DNA element B5 or C14.

DESCRIPTION OF EMBODIMENTS

Figure 1:
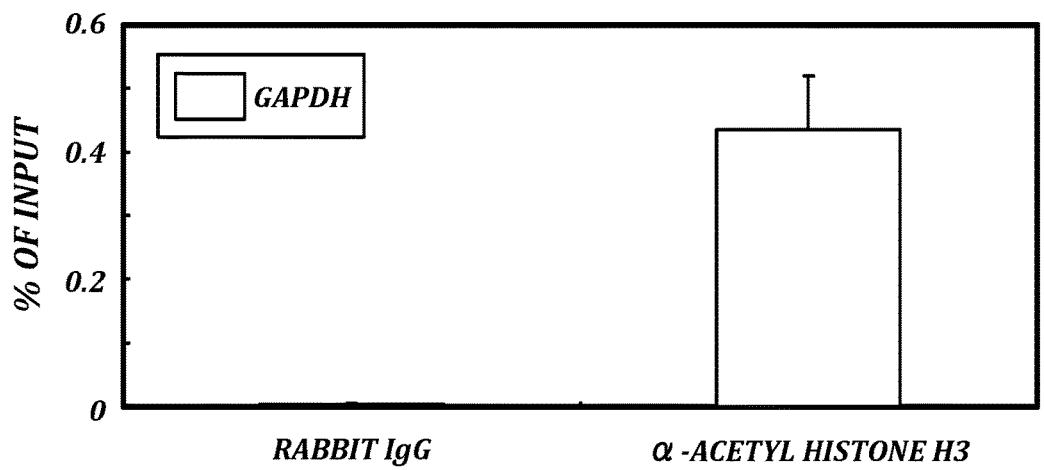
FIG. 1 shows a graph in which it was confirmed by the amplification of a GAPDH region that a sample subjected to ChIP-on-chip was chromatin-immunoprecipitated specifically with an anti-acetylated histone H3 antibody.

Hereinafter, the invention will be specifically described with reference to the Examples. However, these Examples do not limit the technical scope of the invention. The plasmids, restriction enzymes, DNA modification enzymes, and the like to be used in the Examples of the invention are commercially available products and can be used according to common procedures. Further, procedures used for DNA cloning, polynucleotide sequence determination, transformation of a host cell, culturing of a transformed host cell, isolation of an antibody from an obtained culture solution, purification of an antibody, and the like are also well known to those skilled in the art or are available from the literature.

The term "gene" as used herein includes not only DNA, but also mRNA thereof, cDNA, and RNA thereof.

The term "polynucleotide" as used herein is used in the same meaning as a nucleic acid and also includes DNA, RNA, probes, oligonucleotides, and primers.

The terms "polypeptide" and "protein" as used herein are used without distinction.

The term "gene expression" as used herein refers to a phenomenon in which an mRNA is transcribed from a gene and/or a phenomenon in which a protein is translated from the mRNA.

The term "foreign gene" as used herein refers to a gene which is artificially introduced into a host cell.

The term "foreign protein" as used herein refers to a protein encoded by a foreign gene.

The term "gene expression unit" as used herein refers to a polynucleotide having, in the direction of the reading frame of transcription, at least a promoter region, a foreign gene, and a transcription terminator region (poly(A) addition signal).

The term "activity of enhancing foreign gene expression" as used herein refers to the activity of enhancing the production of a foreign protein in a host cell by creating an environment advantageous to transcription and translation for DNA around a gene expression unit containing a foreign gene and significantly improving the transcription and translation efficiency.

The term "DNA element" as used herein refers to a polynucleotide having an activity of enhancing foreign gene expression in cases where the polynucleotide is located in the vicinity of a gene expression unit or in a foreign gene expression vector containing a gene expression unit.

The term "functional fragment of an antibody" as used herein refers to a partial fragment of an antibody having antigen-binding activity and includes Fab, F(ab')$_2$, and the like. However, the term is not limited to these molecules as long as the fragment has a binding affinity for an antigen.

1. DNA Element to be Used for Enhancing Foreign Gene Expression

As shown in Example 1, a DNA element according to the invention can be obtained by using the interaction between acetylated histone H3 and genomic DNA. In general, it is said that the acetylation of histones (H3 and H4) is associated with the activation of transcription, and two main theories have been advocated. One theory is that the acetylation of histones is associated with a change in nucleosome conformation in such a manner that histone tails are acetylated, thereby being electrically neutralized, resulting in weakening of DNA-histone interactions (Mellor J. (2006) Dynamic nucleosomes and gene transcription. Trends Genet. 22(6):320-329). The other theory is that the acetylation of histones is associated with the recruitment of various transcription factors (Nakatani Y. (2001) Histone acetylases—versatile players. Genes Cells 6(2):79-86). In either theory, there is a high possibility that the acetylation of histones is associated with the activation of transcription, and by performing chromatin immunoprecipitation (ChIP) using an anti-acetylated histone H3 antibody, it is possible to concentrate a DNA element interacting with acetylated histone H3.

In the present invention, A2 is an example of a DNA element to be used for enhancing foreign gene expression. A2 is located in the region from 80966429 to 80974878 of human chromosome 15 and is a polynucleotide sequence of 8450 bp, having an AT content of 62.2%. The polynucleotide sequence of A2 is represented by SEQ ID NO:1 in the Sequence Listing.

A7, A18, B5, and C14 are examples of similar DNA elements. A7 is located in the region from 88992123 to 89000542 of human chromosome 11 and is a polynucleotide sequence of 8420 bp, having an AT content of 64.52%. The polynucleotide sequence of A7 is represented by SEQ ID NO:2 in the Sequence Listing.

A18 is located in the region from 111275976 to 111284450 of human chromosome 4 and is a polynucleotide sequence of 8475 bp, having an AT content of 62.54%. The polynucleotide sequence of A18 is represented by SEQ ID NO:3 in the Sequence Listing.

B5 is located in the region from 143034684 to 143043084 of human chromosome 1 and is a polynucleotide sequence of 8401 bp, having an AT content of 66.37%. The polynucleotide sequence of B5 is represented by SEQ ID NO:4 in the Sequence Listing.

Finally, C14 is located in the region from 46089056 to 46097482 of human chromosome 11 and is a polynucleotide sequence of 8427 bp, having an AT content of 63.81%. The polynucleotide sequence of C14 is represented by SEQ ID NO:5 in the Sequence Listing.

In the invention, the activity of enhancing foreign gene expression of the DNA element can be assayed by using the activity of a protein encoded by a reporter gene such as SEAP as an index. In cases where the activity of a reporter protein in the presence of the DNA element is increased, preferably by two times or more, more preferably four times or more, even more preferably five times or more as compared with the case where the DNA element is not present, the DNA element can be determined to have an activity of enhancing foreign gene expression. Even in cases where the activity is increased by two times or more, it is expected that this will reduce the cell culture scale and the cell culture time, and as a result, it is possible to increase the yield and reduce the cell culture cost. If the yield is increased, then it is possible to supply stably a foreign protein to be used as a pharmaceutical. In addition, if the cell culture cost is reduced, the cost for the foreign protein to be used as a pharmaceutical is reduced, and the financial burden on patients to whom the foreign protein is to be administered is also reduced.

In the invention, any one of the above DNA elements may be used alone, and two or more copies of one type of the DNA element may be used. Alternatively, two or more different types of the above DNA elements may be used in combination.

A2, A7, A18, B5, and C14 are preferred examples of the DNA element to be used in the invention.

The DNA element to be used in the invention may be a polynucleotide sequence which comprises a polynucleotide sequence having a homology of 80% or more to any of the polynucleotide sequences represented by SEQ ID NOS:1 to 5 and has an activity of enhancing foreign gene expression. The homology of 80% or more is preferably a homology of 90% or more, more preferably a homology of 95% or more, most preferably a homology of 99% or more. The polynucleotide sequence homology search can be performed in, for example, the DNA Databank of Japan or the like, using a program such as FASTA or BLAST.

The DNA element to be used in the invention may be a DNA element which hybridizes to a polynucleotide consisting of a polynucleotide sequence complementary to a polynucleotide consisting of a polynucleotide sequence selected from the group consisting of the polynucleotide sequences represented by SEQ ID NOS:1 to 5 under stringent conditions and has an activity of enhancing foreign gene expression.

The term "stringent conditions" as used herein refers to conditions in which a so-called specific hybrid is formed but a non-specific hybrid is not formed. For example, conditions in which a complementary strand of a nucleic acid consisting of a polynucleotide sequence having a high homology, i.e., a polynucleotide sequence having a homology of 80% or more, preferably 90% or more, more preferably 95% or more, most preferably 99% or more to a polynucleotide sequence selected from the group consisting of the polynucleotide sequences represented by SEQ ID NOS:1 to 5 hybridizes, and a complementary strand of a nucleic acid comprising a polynucleotide sequence having a lower homology does not hybridize are exemplary stringent conditions. To be more specific, conditions in which the concentration of sodium salt is from 15 to 750 mM, preferably from 50 to 750 mM, more preferably from 300 to 750 mM, the temperature is from 25 to 70° C., preferably from 50 to 70° C., more preferably from 55 to 65° C., and the concentration of formamide is from 0 to 50%, preferably from 20 to 50%, more preferably from 35 to 45% can be exemplified. Further, as the stringent conditions, conditions for washing a filter after hybridization in which the concentration of sodium salt is generally from 15 to 600 mM, preferably from 50 to 600 mM, more preferably from 300 to 600 mM, and the temperature is from 50 to 70° C., preferably from 55 to 70° C., more preferably from 60 to 65° C. can be exemplified.

A person skilled in the art can easily obtain such a homologue gene with reference to Molecular Cloning (Sambrook, J. et al., Molecular Cloning: a Laboratory Manual 2nd ed., Cold Spring Harbor Laboratory Press, 10 Skyline Drive Plainview, N.Y. (1989)) or the like. Further, the homology of the above-mentioned polynucleotide sequence can be determined by a FASTA search or BLAST search in the same manner.

Introduction of a mutation (deletion, substitution, and/or addition) into the above-mentioned polynucleotide sequence can be performed by a method known in this technical field such as a Kunkel method or a gapped duplex method, or based on this method. For example, a mutation introduction kit utilizing a site-directed mutagenesis method (for example, Mutant-K (manufactured by TaKaRa Bio, Inc.), Mutant-G (manufactured by TaKaRa Bio, Inc.), or a LA PCR in vitro Mutagenesis series kit (manufactured by TaKaRa Bio, Inc.)), or the like can be used. Such a mutated polynucleotide can also be used as the DNA element of the invention.

As the DNA element of the invention, a partial fragment comprising at least 3000 or at least 2000 consecutive nucleotides of a polynucleotide sequence represented by any one of SEQ ID NOS: 1 to 5 in the Sequence Listing can be used. Examples of such a partial fragment include: A2-1 to A2-17 which are partial fragments of A2; A7-1 to A7-18 which are partial fragments of A7; A18-1 to A18-4 which are partial fragments of A18; B5-1 to B5-6 which are partial fragments of B5; and C14-1 to C14-14 which are partial fragments of C14. However, the DNA element is not limited to these partial fragments as long as it has an activity of enhancing foreign gene expression.

In the invention, any one of the above partial fragments may be used alone, and also two or more copies of one type of the partial fragment may be used. Alternatively, two or more different types of the partial fragments may be used in combination. Further, a full-length sequence and a partial fragment of any of the above-mentioned DNA elements may be used in combination. In the above combination, the full-length sequence and the partial fragment may be derived from the same DNA element or from different DNA elements.

As for the polynucleotide sequences of the respective fragments of A2, A2-1 corresponds to the polynucleotide sequence of nucleotides 1 to 3000 of SEQ ID NO:1 in the Sequence Listing; A2-2 corresponds to the polynucleotide sequence of nucleotides 2801 to 5800 of SEQ ID NO:1 in the Sequence Listing; A2-3 corresponds to the polynucleotide sequence of nucleotides 5401 to 8450 of SEQ ID NO:1 in the Sequence Listing; A2-4 corresponds to the polynucleotide sequence of nucleotides 701 to 2700 of SEQ ID NO:1 in the Sequence Listing; A2-5 corresponds to the polynucleotide sequence of nucleotides 701 to 2200 of SEQ ID NO:1 in the Sequence Listing; A2-6 corresponds to the polynucleotide sequence of nucleotides 701 to 3700 of SEQ ID NO:1 in the Sequence Listing; A2-7 corresponds to the polynucleotide sequence of nucleotides 2001 to 5000 of SEQ ID NO:1 in the Sequence Listing; A2-8 corresponds to the polynucleotide sequence of nucleotides 4001 to 7000 of SEQ ID NO:1 in the Sequence Listing; A2-9 corresponds to the polynucleotide sequence of nucleotides 1 to 3700 of SEQ ID NO:1 in the Sequence Listing; A2-10 corresponds to the polynucleotide sequence of nucleotides 2001 to 5800 of SEQ ID NO:1 in the Sequence Listing; A2-11 corresponds to the polynucleotide sequence of nucleotides 2801 to 7000 of SEQ ID NO:1 in the Sequence Listing; A2-12 corresponds to the polynucleotide sequence of nucleotides 701 to 5800 of SEQ ID NO:1 in the Sequence Listing; A2-13 corresponds to the polynucleotide sequence of nucleotides 2001 to 7000 of SEQ ID NO:1 in the Sequence Listing; A2-14 corresponds to the polynucleotide sequence of nucleotides 2801 to 8450 of SEQ ID NO:1 in the Sequence Listing; A2-15 corresponds to the polynucleotide sequence of nucleotides 1 to 5800 of SEQ ID NO:1 in the Sequence Listing; A2-16 corresponds to the polynucleotide sequence of nucleotides 701 to 7000 of SEQ ID NO:1 in the Sequence Listing; and A2-17 corresponds to the polynucleotide sequence of nucleotides 2001 to 8450 of SEQ ID NO:1 in the Sequence Listing.

As for the polynucleotide sequences of the respective fragments of A7, A7-1 corresponds to the polynucleotide sequence of nucleotides 601 to 3600 of SEQ ID NO:2 in the Sequence Listing; A7-2 corresponds to the polynucleotide sequence of nucleotides 3601 to 8420 of SEQ ID NO:2 in the Sequence Listing; A7-3 corresponds to the polynucleotide sequence of nucleotides 5401 to 8420 of SEQ ID NO:2 in the Sequence Listing; A7-4 corresponds to the polynucleotide sequence of nucleotides 3401 to 6400 of SEQ ID NO:2 in the Sequence Listing; A7-5 corresponds to the polynucleotide sequence of nucleotides 1501 to 4500 of SEQ ID NO:2 in the Sequence Listing; A7-6 corresponds to the polynucleotide sequence of nucleotides 4401 to 7400 of SEQ ID NO:2 in the Sequence Listing; A7-7 corresponds to the polynucleotide sequence of nucleotides 2401 to 5400 of SEQ ID NO:2 in the Sequence Listing; A7-8 corresponds to the polynucleotide sequence of nucleotides 1 to 3600 of SEQ ID NO:2 in the Sequence Listing; A7-9 corresponds to the polynucleotide sequence of nucleotides 1501 to 5400 of SEQ ID NO:2 in the Sequence Listing; A7-10 corresponds to the polynucleotide sequence of nucleotides 2401 to 6400 of SEQ ID NO:2 in the Sequence Listing; A7-11 corresponds to the polynucleotide sequence of nucleotides 3401 to 7400 of SEQ ID NO:2 in the Sequence Listing; A7-12 corresponds to the polynucleotide sequence of nucleotides 4401 to 8420 of SEQ ID NO:2 in the Sequence Listing; A7-13 corresponds to the polynucleotide sequence of nucleotides 1 to 5400 of SEQ ID NO:2 in the Sequence Listing; A7-14 corresponds to the polynucleotide sequence of nucleotides 1501 to 6400 of SEQ ID NO:2 in the Sequence Listing; A7-15 corresponds to the polynucleotide sequence of nucleotides 2401 to 7400 of SEQ ID NO:2 in the Sequence Listing; A7-16 corresponds to the polynucleotide sequence of nucleotides 3401 to 8420 of SEQ ID NO:2 in the Sequence Listing; A7-17 corresponds to the polynucleotide sequence of nucleotides 1 to 6400 of SEQ ID NO:2 in the Sequence Listing; and A7-18 corresponds to the polynucleotide sequence of nucleotides 1501 to 7400 of SEQ ID NO:2 in the Sequence Listing.

As for the polynucleotide sequences of the respective fragments of A18, A18-1 corresponds to the polynucleotide sequence of nucleotides 1 to 5040 of SEQ ID NO:3 in the Sequence Listing; A18-2 corresponds to the polynucleotide sequence of nucleotides 1001 to 6002 of SEQ ID NO:3 in the Sequence Listing; A18-3 corresponds to the polynucleotide sequence of nucleotides 2001 to 7000 of SEQ ID NO:3 in the Sequence Listing; and A18-4 corresponds to the polynucleotide sequence of nucleotides 3000 to 7000 of SEQ ID NO:3 in the Sequence Listing.

The start and end points of the respective fragments of A2, A7 and A18 are also set forth in FIG. 18.

As for the polynucleotide sequences of the respective fragments of B5, B5-1 corresponds to the polynucleotide sequence of nucleotides 1 to 4001 of SEQ ID NO:4 in the Sequence Listing; B5-2 corresponds to the polynucleotide sequence of nucleotides 1 to 3200 of SEQ ID NO:4 in the Sequence Listing; B5-3 corresponds to the polynucleotide sequence of nucleotides 2491 to 5601 of SEQ ID NO:4 in the Sequence Listing; B5-4 corresponds to the polynucleotide sequence of nucleotides 5373 to 8401 of SEQ ID NO:4 in the Sequence Listing; B5-5 corresponds to the polynucleotide sequence of nucleotides 901 to 4001 of SEQ ID NO:4 in the Sequence Listing; and B5-6 corresponds to the polynucleotide sequence of nucleotides 4001 to 7000 of SEQ ID NO:4 in the Sequence Listing.

As for the polynucleotide sequences of the respective fragments of C14, C14-1 corresponds to the polynucleotide sequence of nucleotides 960 to 4015 of SEQ ID NO:5 in the Sequence Listing; C14-2 corresponds to the polynucleotide sequence of nucleotides 1987 to 5014 of SEQ ID NO:5 in the Sequence Listing; C14-3 corresponds to the polynucleotide sequence of nucleotides 4020 to 7119 of SEQ ID NO:5 in the Sequence Listing; C14-4 corresponds to the polynucleotide sequence of nucleotides 960 to 8141 of SEQ ID NO:5 in the Sequence Listing; C14-5 corresponds to the polynucleotide sequence of nucleotides 960 to 6011 of SEQ ID NO:5 in the Sequence Listing; C14-6 corresponds to the polynucleotide sequence of nucleotides 4939 to 8141 of SEQ ID NO:5 in the Sequence Listing; C14-7 corresponds to the polynucleotide sequence of nucleotides 960 to 5014 of SEQ ID NO:5 in the Sequence Listing; C14-8 corresponds to the polynucleotide sequence of nucleotides 2994 to 7119 of SEQ ID NO:5 in the Sequence Listing; C14-9 corresponds to the polynucleotide sequence of nucleotides 4020 to 8141 of SEQ ID NO:5 in the Sequence Listing; C14-10 corresponds to the polynucleotide sequence of nucleotides 1 to 5014 of SEQ ID NO:5 in the Sequence Listing; C14-11 corresponds to the polynucleotide sequence of nucleotides 1987 to 7119 of SEQ ID NO:5 in the Sequence Listing; C14-12 corresponds to the polynucleotide sequence of nucleotides 2994 to 8141 of SEQ ID NO:5 in the Sequence Listing; C14-13 corresponds to the polynucleotide sequence of nucleotides 960 to 7119 of SEQ ID NO:5 in the Sequence Listing; and C14-14 corresponds to the polynucleotide sequence of nucleotides 1987 to 8141 of SEQ ID NO:5 in the Sequence Listing.

The start and end points of the respective fragments of B5 and C14 are also set forth in FIG. 19.

2. Acquisition of Polynucleotide

In the invention, a polynucleotide containing a foreign gene encoding a foreign protein the production of which is to be increased, which will be described later, can be obtained by common procedures as described below. For example, such a polynucleotide can be isolated by screening a cDNA library derived from cells or tissues expressing the foreign gene using a DNA probe synthesized by being based on a fragment of the foreign gene. mRNA can be prepared by methods commonly used in this technical field. For example, the cells or tissues are treated with a guanidine reagent, a phenol reagent, etc., thereby obtaining total RNA, and thereafter, poly(A)+RNA (mRNA) is obtained by an affinity column method using an oligo(dT) cellulose column or a poly U-Sepharose column containing Sepharose 2B as a carrier, or the like, or by a batch method. Also, the poly(A)+RNA may further be fractionated by sucrose density-gradient centrifugation or the like. Then, a single-stranded cDNA is synthesized using the thus obtained mRNA as a template, and also using oligo dT primers and a reverse transcriptase. From the thus obtained single-stranded cDNA, a double-stranded cDNA is synthesized using DNA polymerase I, DNA ligase, RNase H, and the like. The thus synthesized double-stranded cDNA is blunted using T4 DNA polymerase, followed by ligation to an adapter (such as EcoRI adapter), phosphorylation, and the like, and the resulting DNA is incorporated into a lambda phage such as λgt11 to achieve in vivo packaging, whereby a cDNA library can be prepared. It is also possible to prepare a cDNA library using a plasmid vector other than lambda phages. Thereafter, a clone containing a target DNA (a positive clone) may be selected from the cDNA library.

In cases where the above-mentioned DNA element to be used for increasing the production of a protein or a polynucleotide containing a foreign gene is isolated from genomic DNA, or a polynucleotide containing promoter and terminator regions is isolated from genomic DNA, according to a common procedure (Molecular Cloning (1989), Methods in Enzymology 194 (1991)), genomic DNA is extracted from a cell line of an organism to be used as a collection source, and a polynucleotide is selected and isolated. The extraction of genomic DNA can be performed according to, for example, the method of Cryer et al. (Methods in Cell Biology 12:39-44 (1975)) or the method of P. Philippsen et al. (Methods Enzymol. 194:169-182 (1991)).

The target DNA element or the polynucleotide containing a foreign gene can also be obtained by, for example, the PCR method (PCR Technology. Henry A. Erlich, Atockton Press (1989)). In the amplification of a polynucleotide using the PCR method, 20- to 30-mer synthetic single-stranded DNAs are used as primers and genomic DNA is used as a template. The amplified gene is used after the polynucleotide sequence of the gene is confirmed. As the template for PCR, a genomic DNA library such as a bacterial artificial chromosome (BAC) can be used.

On the other hand, the polynucleotide containing a foreign gene whose sequence is not known can be obtained by (a) preparing a gene library according to a common procedure, and (b) selecting a desired polynucleotide from the prepared gene library and amplifying the polynucleotide. The gene library can be prepared by partially digesting chromosomal DNA obtained by a common procedure from a cell line of an organism to be used as a collection source using an appropriate restriction enzyme to fragment the chromosomal DNA, ligating the obtained fragments to an appropriate vector, and introducing the vector into an appropriate host. The gene library can also be prepared by extracting mRNA from the cells, synthesizing cDNA from the mRNA, ligating the cDNA to an appropriate vector, and introducing the vector into an appropriate host. As the vector to be used in such preparation, a plasmid generally known as a vector for gene library preparation, a phage vector, a cosmid, or the like can also be used. As the host to be transformed or transfected, a host suitable for the type of the above-mentioned vector may be used. The polynucleotide containing the foreign gene is selected from the above-mentioned gene library by a colony hybridization method, a plaque hybridization method, or the like using a labeled probe containing a sequence specific for the foreign gene.

Further, the polynucleotide containing the foreign gene can also be produced by total chemical synthesis. For example, the gene can be synthesized by a method in which two pairs of complementary oligonucleotides are prepared and annealed, a method in which several annealed DNA strands are ligated by a DNA ligase, a method in which several partially complementary polynucleotides are prepared and gaps are filled by PCR, or the like.

The determination of a polynucleotide sequence can be performed by a conventional technique, for example, a dideoxy method (Sanger et al., (1977) Proc. Natl. Acad. Sci. USA 74:5463-5467), or the like. Further, the above determination of a polynucleotide sequence can also be easily performed using a commercially available sequencing kit or the like.

3. Foreign Gene Expression Vector, Element Vector

As a foreign gene expression vector of the invention, a vector containing one type of the above-mentioned DNA elements, two or more copies of one type of the above-mentioned DNA elements, or two or more different types of the above-mentioned DNA elements in combination, and further containing a foreign gene expression unit is provided. When a foreign gene is expressed in a host cell using the above-mentioned foreign gene expression vector, the DNA element may be located immediately upstream or downstream of the gene expression unit, or may be located at a position away from the gene expression unit. Further, one foreign gene expression vector containing a plurality of such DNA elements may be used. Incidentally, the DNA element may be inserted in either forward or reverse orientation with respect to the gene expression unit.

Further, as the vector to be used in the invention, a vector containing one type of the above-mentioned DNA elements, two or more copies of one type of the above-mentioned DNA elements, or two or more different types of the above-mentioned DNA elements in combination, and containing no gene expression unit (hereinafter also referred to as an "element vector") is also included. Such an element vector can be used in combination with the above-mentioned foreign gene expression vector containing the DNA element or a foreign gene expression vector containing no DNA element and containing only the foreign gene expression unit. By allowing the element vector to coexist with the foreign gene expression vector, the expression of the foreign gene is enhanced as compared with cases where the foreign gene expression vector is used alone and, therefore, the combination of the above-mentioned vectors is also included in the foreign gene expression vector of the invention.

The gene encoding the foreign protein is not particularly limited, however, examples thereof include reporter genes such as secretory alkaline phosphatase (SEAP), a green fluorescent protein (GFP), and luciferase; various enzyme genes such as an α-amylase gene and an α-galactosidase gene; genes of various interferons which are pharmaceutically useful and physiologically active proteins such as interferon α and interferon γ; genes of various interleukins such as IL-1 and IL-2; various cytokine genes such as an erythropoietin (EPO) gene and a granulocyte colony-stimulating factor (G-CSF) gene; growth factor genes; and antibody genes. These genes may be obtained by any method.

The invention is particularly effective in relation to a protein which is highly hydrophobic and a protein which is difficult to get secreted and produced due to composite formation. Thus, the above-mentioned foreign protein includes a multimeric protein such as a heteromultimer which is an antibody or a functional fragment thereof. The "functional fragment of an antibody" refers to a partial fragment of an antibody having an antigen-binding activity and includes Fab, F(ab')2, Fv, scFv, diabodies, linear antibodies, polyspecific antibodies formed from antibody fragments, and the like. The functional fragment of an antibody also includes Fab' which is a monovalent fragment in a variable region of an antibody obtained by treating F(ab')2 under reducing conditions. However, the functional fragment is not limited to these molecules as long as the fragment has a binding affinity for an antigen. Further, these functional fragments include not only a fragment obtained by treating a full-length molecule of an antibody protein with an appropriate enzyme, but also a protein produced in an appropriate host cell using a genetically modified antibody gene.

The gene expression unit has, in the direction of the reading frame of transcription, at least a promoter region, a foreign gene, and a transcription terminator region (poly(A) addition signal). The promoter which can be used here may be a constitutive expression promoter or an inducible expression promoter. Examples of a constitutive expression promoter include various natural promoters such as an SV40 early promoter, an adenovirus E1A promoter, a CMV (cytomegalovirus) promoter, an EF-1α (human elongation factor-1α) promoter, an HSP70 promoter, an MT promoter, an RSV promoter, a UBC promoter, and an actin promoter; and artificial (fusion) promoters such as an SRα promoter and a CAG promoter. Further, the poly(A) addition sequence may be a sequence having the activity of causing transcription termination for the transcription from the promoter, and may be a sequence from a gene the same as or different from the promoter.

It is necessary to use a strong promoter in order to increase the production of a foreign protein. However, when it is attempted to produce a protein which is difficult to have fold or a protein which is difficult to get secreted using a highly active promoter, the protein may instead fail to be secreted. This is because when the protein is produced in an amount exceeding the capacity of the ribosome in which translation is performed and the endoplasmic reticulum where folding and secretion are performed, the excessively produced protein is denatured, accumulated, and ubiquitinated in cells, and then degraded by proteosomes. Accordingly, it is preferred that a promoter, which can attain an expression level to such an extent that the resulting protein is not denatured or aggregated or the amount of the resulting protein does not exceed the secretion capacity, is appropriately selected. Alternatively, the promoter is used by adjusting (for example, decreasing) the activity of the promoter. Among the multimeric proteins, a molecule forming a heteromultimer is susceptible to the above-described effect, and, in particular a molecule, such as an antibody, which is a heterotetramer. An antibody has two heavy chain molecules and two light chain molecules which are associated with one another, and therefore, in order to appropriately associate the molecules, the expression level thereof is an important factor.

Further, the foreign gene expression vector and the element vector of the invention can each contain a selection marker for selecting a transformant. By using, for example, a drug-resistant marker which imparts resistance to a drug such as cerulenin, aureobasidin, Zeocin, canavanine, cycloheximide, hygromycin, puromycin, blasticidin, tetracycline, kanamycin, ampicillin, or neomycin, a transformant can be selected. Further, where a gene which imparts resistance to a solvent such as ethanol, resistance to the osmotic pressure of glycerol, a salt, or the like, resistance to a metal ion such as a copper ion, or the like is used as a marker, a transformant can also be selected.

The foreign gene expression vector and the element vector of the invention may each be a vector which is not incorporated into the chromosomal DNA. In general, the foreign gene expression vector is transfected into a host cell, and thereafter randomly incorporated into the chromosome. However, by using a constituent component derived from a mammalian virus such as simian virus 40 (SV40), a papillomavirus (BPV, HPV), or EBV, the vector can be used as an episomal vector which is self-replicable in the transfected host cell. For example, a vector containing an SV40-derived replication origin (oriP) and a sequence encoding an SV40 large T antigen which is a trans-acting factor, a vector containing an EBV-derived oriP and a sequence encoding EBNA-1, or the like can be used. The effect of the DNA element can be expressed by the activity of enhancing foreign gene expression regardless of the type of vector or the presence or absence of incorporation thereof into the chromosome.

4. Transformed Cell

The transformed cell of the invention is a transformed cell into which the foreign gene expression vector described in the above item "3" containing the DNA element described in the above item "1" has been introduced. As the foreign gene expression vector, only a foreign gene expression vector containing a DNA element may be introduced (A), or a foreign gene expression vector containing a DNA element and also an element vector described in the above item "3" may be introduced in combination (B). Alternatively, a foreign gene expression vector containing no DNA element and an element vector may be introduced in combination (C).

The expression of a foreign gene in a host cell using the above combination of (B) or (C) can be performed according to, for example, the method of Girod et al. (Biotechnology and Bioengineering 91:2-11 (2005)) and the method of Otte et al. (Biotechnol. Prog. 23:801-807 (2007)).

Examples of the host cell to be transformed include eucaryotic cells, preferred examples thereof include mammalian cells, more preferred examples include cells derived from humans, mice, rats, hamsters, monkeys, or cattle. Examples of such mammalian cells include COS-1 cells, 293 cells, and CHO cells (CHO-K1, DG44, CHO dhfr-, CHO-S); however, the host cell is not limited thereto.

In the invention, any method may be used for introducing the expression vector into the host cell as long as the method allows the introduced gene to be stably present in the host cell and to be adequately expressed therein. Examples of the method which is generally used include a calcium phosphate method (Ito et al. (1984) Agric. Biol. Chem. 48:341), an electroporation method (Becker, D. M. et al. (1990) Methods. Enzymol., 194:182-187), a spheroplast method (Creggh et al. (1985) Mol. Cell. Biol. 5:3376), a lithium acetate method (Itoh, H. (1983) J. Bacteriol. 153:163-168), and a lipofection method.

5. Method for Producing Foreign Protein

In the invention, a foreign protein can be produced by culturing the transformed cell described in the above item "4", into which a gene encoding the foreign protein has been introduced using the vector described in the above item "3" by a known method, collecting the protein from the resulting culture product, followed by purification of the protein. The term "culture product" as used herein refers to cultured cells or a cell homogenate in addition to a culture supernatant. Incidentally, as the foreign protein which can be produced using the transformed cell described in the above item "4", not only a monomeric protein, but also a multimeric protein can be selected. In cases where a hetero-multimeric protein formed of a plurality of different subunits is produced, it is necessary to introduce a plurality of genes encoding these subunits into the host cell described in the above item "4", respectively.

The method for culturing the transformed cell can be performed according to conventional methods for culturing host cells.

In cases where the transformed cell is a mammalian cell, the cell is cultured under conditions of, for example, 37° C. and 5% or 8% $CO_2$ for a culture time of from about 24 to 1000 hours. The culturing can be performed through batch culture, fed-batch culture, continuous culture, or the like under static, shaking, stirring, or aeration conditions.

The confirmation of the expression product of the gene encoding the foreign protein from the above-mentioned culture product (culture solution) can be performed by SDS-PAGE, a Western analysis, ELISA, or the like. In order to isolate and purify the produced protein, a conventional protein isolation and purification method may be used. After completion of the culturing, in cases where the target protein is produced in the cells, the cells are homogenized using an ultrasonic homogenizer, a French press, a Manton-Gaulin homogenizer, Dinomil, or the like, thereby obtaining the target protein. Further, cases where the target protein is produced outside the cells, the culture solution is used as such, or the cells are removed by centrifugation or the like. Thereafter, the target protein is collected by extraction or the like using an organic solvent, and then the collected target protein may be isolated and purified by using techniques such as various chromatography techniques (hydrophobic chromatography, reverse-phase chromatography, affinity chromatography, ion exchange chromatography, etc.), gel filtration using a molecular sieve, and electrophoresis using a polyacrylamide gel or the like alone or in combination according to need.

The above-mentioned culturing methods and purification methods are only examples, and the methods are not limited thereto. The amino acid sequence of the purified gene product can be confirmed by a known amino acid analysis technique, such as automated amino acid sequence determination using the Edman degradation method.

6. Method for Producing Antibody Protein

As the hetero-multimeric protein to be produced using the production method described in the above item "5", an antibody protein can be exemplified. The antibody protein is a tetrameric protein comprising two molecules of heavy chain polypeptides and two molecules of light chain polypeptides. Accordingly, in order to obtain such an antibody protein in a state of maintaining an antigen-binding affinity, it is necessary to introduce both heavy and light chain genes into the transformed cell described in the above item "4". In this case, the heavy and light chain gene expression units may be present on the same expression vector or different expression vectors.

As the antibody to be produced in the invention, an antibody prepared by immunizing an experimental animal such as a rabbit, a mouse, or a rat with a desired antigen can be exemplified. Further, a chimeric antibody and a humanized antibody obtained by using the above-mentioned antibody as a starting material can be also exemplified as the antibody to be produced in the invention. Further, a human antibody obtained using a genetically modified animal or a phage display method is also included in the antibody to be produced in the invention.

The antibody gene to be used for the production of the antibody is not limited to an antibody gene having a specific polynucleotide sequence as long as a combination of a heavy chain polypeptide and a light chain polypeptide to be transcribed and translated from the antibody gene has an activity of binding to a given antigen protein.

Further, it is not necessary that the antibody gene encodes the full-length molecule of the antibody, and a gene encoding a functional fragment of the antibody can be used. Such a gene encoding a functional fragment thereof can be obtained by genetically modifying a gene encoding the full-length molecule of an antibody protein.

7. Production Method for Other Foreign Proteins

Examples of the foreign protein to be produced using the production method of the invention include, in addition to the above-mentioned antibodies, various proteins derived from humans or non-humans, functional fragments thereof, and modified products thereof. Examples of such proteins and the like include peptide hormones such as atrial natriuretic peptide (ANP), brain natriuretic peptide (BNP), C-type natriuretic peptide (CNP), vasopressin, somatostatin, growth hormone (GH), insulin, oxytocin, ghrelin, leptin, adiponectin, renin, calcitonin, osteoprotegerin, and insulin-like growth factor (IGF); cytokines such as interleukin, chemokine, interferon, tumor necrosis factors (such as TNF-α, TNF-β, and TNF super family), nerve growth factors (such as NGF), cell growth factors (such as EGF, FGF, PDGF, HGF, and TGF), hematopoietic growth factors (such as CSF, G-CSF, and erythropoietin), and adipokine; receptors such as TNF receptors; enzymes such as lysozyme, protease, proteinase, and peptidase; functional fragments thereof (fragments having part or all of the biological activity of the original protein), and fusion proteins comprising any of these proteins. However, the proteins are not limited thereto.

EXAMPLES

Hereinafter, the invention will be specifically described with reference to the Examples. However, these Examples do not limit the technical scope of the invention. The plasmids, restriction enzymes, DNA modification enzymes, and the like to be used in the Examples of the invention are commercially available products and can be used according to common procedures. Further, procedures used for DNA cloning, polynucleotide sequence determination, transformation of a host cell, culturing of a transformed host cell, collection of a protein from the resulting culture product, purification of a protein, and the like are also well known to those skilled in the art or can be found in the literature.

Example 1

Extraction of DNA Element
(1-1) Chromatin Immunoprecipitation Using Anti-Acetylated Histone H3 Antibody ChIP using an anti-acetylated histone antibody was performed using EZ ChIP (Upstate) according to the following procedure. Incidentally, unless otherwise stated, as the antibodies, buffers, and the like used in the following procedure, Upstate's products were used.

First, 293F cells (Invitrogen) were cultured using GIBCO (registered trademark) FreeStyle™ 293 Medium (Invitrogen) under conditions of 37° C. and 8% $CO_2$, followed by centrifugation (1000 rpm, 5 min, room temperature), whereby cells in the growth phase were collected. After $2\times10^7$ cells were fixed in a medium containing 1% formaldehyde for 10 minutes, 10× glycine was added thereto, followed by incubation at room temperature for 5 minutes. After centrifugation (3000 rpm, 5 min, 4° C.), the supernatant was removed, and PBS was added to the cell pellet to suspend the cells. Then, the cell suspension was centrifuged again to remove PBS, and thereafter an SDS lysis buffer was added to the cell pellet to suspend and lyse the cells. Each sample obtained by cell lysis was subjected to DNA fragmentation using an ultrasonic homogenizer (BRANSON) while cooling the sample with ice water, and a dilution buffer containing a protease inhibitor cocktail and Protein G-immobilized agarose were added thereto. The resulting mixture was rotated at 4° C. for 1 hour, followed by centrifugation, and then the supernatant was collected. Subsequently, 10 μg of normal rabbit IgG or an α-acetyl histone H3 antibody was added thereto, followed by rotating overnight at 4° C. To the resulting solution, Protein G-immobilized agarose was added, and the resulting mixture was rotated at 4° C. for 1 hour, followed by centrifugation, and then the pellet was collected. The thus obtained pellet was washed twice with Low Salt Immune Complex Wash Buffer, twice with High Salt Immune Complex Wash Buffer, twice with LiCl Immune Complex Wash Buffer, and finally four times with TE Buffer. Then, an elution buffer (containing 20 μl of 1 M sodium hydrogen carbonate, 10 μl of SDS, and 170 μl of sterile water) was added thereto. After 30 minutes, the mixture was centrifuged, and the supernatant was collected.

Subsequently, 5 M sodium chloride was added to the supernatant, and the resulting mixture was heated overnight at 65° C. Then, RNase A was added thereto, and the resulting mixture was incubated at 37° C. for 30 minutes. Then, 0.5 M EDTA, 1 M Tris-HCl, and Proteinase K were added thereto, and the resulting mixture was incubated at 45° C. for 2 hours.

Finally, Reagents A, B, and C were added thereto in an amount 5 times greater than that of the solution obtained by the treatment with Proteinase K, followed by centrifugation (10000 rpm, 30 sec, room temperature) using Spin filter, whereby chromatin-immunoprecipitated DNA was purified.

(1-2) Microarray Analysis

By using GenomePlex Complete Whole Genome Amplification (WGA) Kit (Sigma), each ChIP sample obtained in (1-1) was amplified. The procedure was in accordance with Sigma's protocol accompanying the Kit.

In order to confirm ChIP, by using 320 ng of each DNA amplified by WGA as a template, and also using the following primers and SYBR (registered trademark) Premix Ex Taq™ (Perfect Real Time) (TAKARA), a glycelaldehyde-3-phosphate dehydrogenase (GAPDH) internal gene was amplified by the PCR method (95° C. for 5 sec and 60° C. for 20 sec×45 cycles). Incidentally, GAPDH is a house keeping gene to be used as a positive control for confirming whether a DNA element is enriched by ChIP, and the PCR method was performed using primers attached to EZ ChIP (Upstate).

(SEQ ID NO: 8)
5'-TACTAGCGGTTTTACGGGCG-3'

(SEQ ID NO: 9)
5'-TCGAACAGGAGGAGCAGAGAGCGA-3'

As shown in FIG. 1, it was confirmed that GAPDH was amplified specifically in the sample subjected to immunoprecipitation with an anti-acetylated histone H3 antibody. Each of the DNA samples amplified by WGA was subjected to microarray analysis (NimbleGen) to perform Chromatin Immunoprecipitation-on-chip (ChIP-on-chip). "ChIP-on-chip" is a technique for identifying each DNA element by subjecting each DNA enriched in (1-1) to microarray analysis.

(1-3) Extraction of DNA Element

Based on the results of the ChIP-on-chip analysis obtained in (1-2), 5 sequences having an AT content of 62% or more were extracted.

A2: chromosome 15 (80966429 to 80974878)
A7: chromosome 11 (88992123 to 89000542)
A18: chromosome 4 (111275976 to Ser. No. 11/284,450)
B5: chromosome 1 (143034684 to 143043084)
C14: chromosome 11 (46089056 to 46097482)

Example 2

Effect of DNA Element Using Expression of Secretory Alkaline Phosphatase (SEAP) as Index
(2-1) Construction of SEAP Expression Vector By using pSEAP2-control (Clontech) as a template, the SEAP gene was amplified by the PCR method (94° C. for 30 sec and 68° C. for 2 min×40 cycles) using the following primers and KOD-plus-(TOYOBO).

(SEQ ID NO: 10)
5'-AAAGCTAGCATGCTGCTGCTGCTGCTGCTGGGCC-3'

(SEQ ID NO: 11)
5'-AAAAGATCTTCATGTCTGCTCGAAGCGGCCGGCCGC-3'

Subsequently, the amplified SEAP fragment was separated by agarose gel electrophoresis and cut out from the gel, followed by purification using a QIAquick Gel Extraction Kit (Qiagen). The thus obtained DNA fragment was used as an insert. The insert was digested with the restriction enzymes NheI and BglII, and a vector pIRES hyg3 (Clontech) was digested with the restriction enzymes NheI and BamHI. The resulting DNA fragments were subjected to agarose gel electrophoresis to separate the target fragments, respectively, and the target fragments were cut out from the gel, followed by purification. Then, a ligation reaction and transformation were performed. The ligation reaction was performed using LigaFast Rapid DNA Ligation System (Promega). The transformation was performed as follows. First, frozen competent cells JM109 (TAKARA) were thawed, and 10 µl of a solution obtained after the ligation reaction was added to a solution of the thawed cells, and the resulting mixture was left to stand on ice for 30 minutes. Thereafter, a heat shock (42° C., 45 sec) was applied to the mixture, and the mixture was cooled on ice for 5 minutes. To this cell suspension, 1 ml of LB medium was added, and the resulting mixture was shaken at 37° C. for 1 hour. Then, the mixture was plated on an LB plate containing 0.1 mg/ml ampicillin, and the plate was incubated at 37° C. for 14 to 16 hours. Thereafter, by alkaline lysis, a target plasmid was collected from colonies cultured on the LB plate. Finally, the polynucleotide sequence of SEAP in the plasmid obtained by alkaline lysis was determined, whereby pCMV/SEAP ires Hygro was constructed.

(2-2) Cloning of DNA Element

Subsequently, each of the DNA elements extracted in Example 1 was cloned into the SEAP expression vector obtained in (2-1) using BAC SUBCLONING Kit (Gene Bridges) from a bacterial artificial chromosome (BAC) containing a polynucleotide sequence corresponding to each of the DNA elements.

First, pCMV/SEAP ires Hygro obtained in (2-1) was digested with the restriction enzyme SpeI for several hours, followed by ethanol precipitation, and the precipitate was dissolved in sterile water. By using the vector digested with SpeI as a template, the PCR method (94° C. for 15 sec, 55° C. for 30 sec, and 68° C. for 10 min×30 cycles) was performed using the following primers and KOD-plus-(TOYOBO).

A2D:

(SEQ ID NO: 12)
5'-GGAAATTGAGAAGTATCATTCACAACAGTACCACAAACATGAAA

TAAATGTGGATCCTATTAATAGTAATCAATTACG-3'

A2R:

(SEQ ID NO: 13)
5'-CTCATTCTGTGGGTTGTCATTTCACTTCCTTGATGCTATCCTTT

CAAGCAAAATCCTAGTCAATAATCAATGTCAACG-3'

A7D:

(SEQ ID NO: 14)
5'-CTTATTTTCTAAGTAGTATAGACTTAATTGTGAGAACAAAATAA

AAACTTGGATCCTATTAATAGTAATCAATTACG-3'

A7R:

(SEQ ID NO: 15)
5'-CTCTTCCCATTCTCATTTGAATCTACTTCAAAAGGTTTACCATA

CTAAGACCTAGTCAATAATCAATGTCAACG-3'

A18D:

(SEQ ID NO: 16)
5'-CGCCTGTAATCCCAGCACTTTGGGAGGCTGAGGCGGGTGGATCA

CCTGAGGTCGATCCTATTAATAGTAATCAATTACG-3'

A18R:

(SEQ ID NO: 17)
5'-CATACAGAAGCCAGTTTGAACTGAGACCTCACTCCATTTCTTAC

AAGTTATGCCCTAGTCAATAATCAATGTCAACG-3'

B5D:

(SEQ ID NO: 18)
5'-ACCGTTTTATATTGTTTAAGCATTTCCTAGACATATTTGGCTAC

AAATCTAGATCCTATTAATAGTAATCAATTACG-3'

B5R:

(SEQ ID NO: 19)
5'-GATCTTAGGGGGGCTGATTATATAAAACAATAGAAATGTAGTCT

TAGATGAAACCTAGTCAATAATCAATGTCAACG-3'

C14D:

(SEQ ID NO: 20)
5'-CACAAAGTTCACTGTCAAGGCCAGGTGATGAGGCCCACACATGCCC

GGACCTTGATCCTATTAATAGTAATCAATTACG-3'

C14R:

(SEQ ID NO: 21)
5'-CAAAACCTCATCTCTACTGAAAATAGAAAATTAGCTGGGCGTGGTG

GCAGGTGCCCTAGTCAATAATCAATGTCAACG-3'

After the amplification was confirmed by agarose gel electrophoresis using a portion of the reaction solution, the rest of the reaction solution was subjected to ethanol precipitation. The precipitate was dissolved in sterile water, and the resulting solution was used as DNA for transformation.

Subsequently, preparation of *Escherichia coli* for transformation was performed.

BAC clones corresponding to the 5 sequences extracted in Example 1 are as follows.

| Extracted sequence | Corresponding BAC clone |
|---|---|
| A2 | RP11-152F13 |
| A7 | RP11-643G5 |
| A18 | RP11-115A14 |
| B5 | RP11-640M9 |
| C14 | RP11-702F3 |

Figure 2:
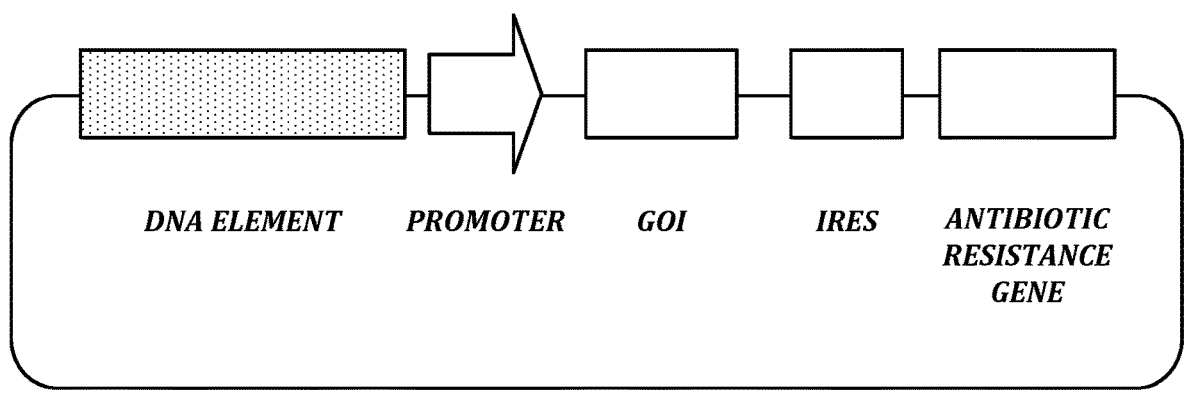
FIG. 2 is a schematic view of an SEAP expression vector into which a DNA element has been inserted.

10 μl of the above-mentioned BAC (Advanced Geno-Techs Co.) which was thawed was inoculated into 1 ml of a medium (containing chloramphenicol at a final concentration of 15 μg/ml) and incubated overnight at 37° C. 30 μl of the culture solution was transferred to 1.4 ml of a medium (containing chloramphenicol at a final concentration of 15 μg/ml) and incubated at 37° C. for 2 hours. Centrifugation and washing with sterile water were repeated twice, and the cells were suspended in 20 μl of sterile water. To a cooled cuvette (0.1 cm), 1 μl of pRED/ET (Gene Bridges) and *Escherichia coli* were added, followed by electroporation (1350 V, 10 μF). Then, 1 ml of SOC medium was added thereto, and the resulting mixture was incubated at 30° C. for 70 minutes. 100 μl of the culture solution was plated on an LB plate (containing tetracycline and chloramphenicol at final concentrations of 3 μg/ml and 15 μg/ml, respectively), and incubated overnight at 30° C. On the subsequent day, each colony thus obtained was inoculated into 1 ml of a medium (containing tetracycline and chloramphenicol at final concentrations of 3 μg/ml and 15 μg/ml, respectively), and incubated overnight at 30° C. 30 μl of the culture solution was transferred to 1.4 ml of a medium (containing tetracycline and chloramphenicol at final concentrations of 3 μg/ml and 15 μg/ml, respectively), and incubated at 30° C. for 2 hours. Then, 50 μl of 10% L-arabinose was added thereto, and incubation was further performed at 37° C. for 1 hour. Thereafter, washing with sterile water was repeated twice, and *Escherichia coli* which was suspended in 30 μl of sterile water and 1 μl of the DNA for transformation were added to a cooled cuvette (0.1 cm), followed by electroporation (1350 V, 10 μF). Then, 1 ml of SOC medium was added thereto, and the resulting mixture was incubated at 37° C. for 90 minutes. The total amount of the culture solution was plated on an LB plate (containing 100 μg/ml ampicillin), and the plate was incubated. Thereafter, a target plasmid was obtained by alkaline lysis. Finally, the sequence of the obtained plasmid and the restriction enzyme sites thereof were confirmed, whereby a target plasmid was constructed. The vector construct is shown in FIG. 2.

(2-3) Evaluation Using SEAP Expression as Index

Each plasmid constructed in (2-2) was evaluated using the host cell CHO-K1 (ATCC) and transfection reagent Lipofectamine 2000 (Invitrogen).

Antibiotic selection with hygromycin at 800 μg/ml was performed for about 2 weeks starting 2 days after transfection, whereby a stably expressing polyclonal cell line was established. The thus established cell line was subjected to medium replacement on the day before measurement, and a given number of the cells were seeded into a 24-well plate (IWAKI). At 24 hours after plating the cells, the culture supernatant was collected, and the activity of SEAP was measured. The activity of SEAP in the culture supernatant was measured using SensoLyte™ pNPP Secreted Alkaline Phosphatase Reporter Assay (ANASPEC).

Figure 3:
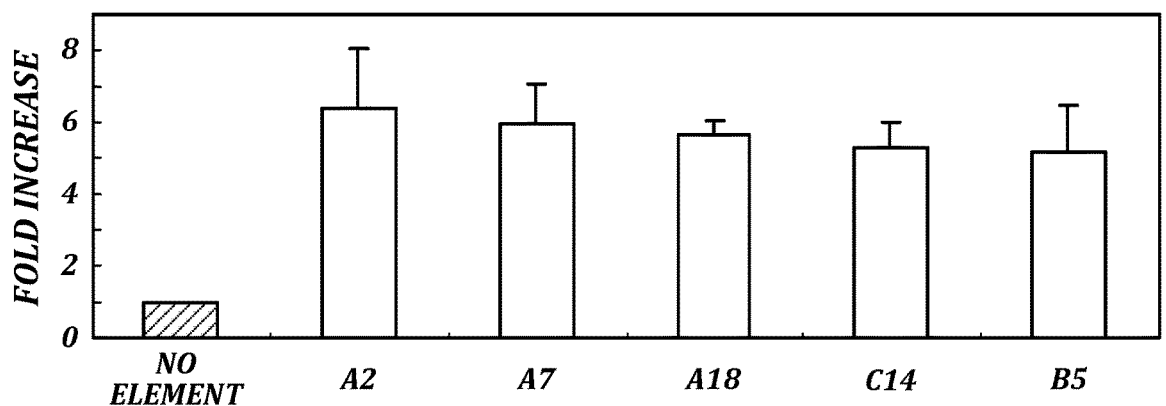
FIG. 3 is a graph showing the expression of SEAP under the control of a CMV promoter in a stably expressing CHO cell line either without a DNA element or with DNA element A2, A7, A18, B5, or C14. The effects of DNA elements A2, A7, A18, B5, and C14 on enhancement of expression were confirmed.

The measured results are shown in FIG. 3. When the activity of SEAP of the control with no element was normalized to 1, the activity of SEAP in the culture supernatant of the stably expressing CHO cell line having the DNA element A2, A7, A18, B5, or C14 showed a numerical value five times or more higher than that of the control. Based on the results, it was confirmed that all the 5 types of DNA elements dramatically enhance SEAP expression. Incidentally, the polynucleotide sequences of the above 5 types of DNA elements are represented by SEQ ID NOS:1 to 5 in the Sequence Listing, respectively.

Example 3

Generality of Promoter to be Used in Combination

The promoter for the vector used in the evaluation of the DNA elements in Example 2 was a CMV promoter, and thus the use of DNA elements in combination with other general promoters was studied in Example 3.

(3-1) Construction of SEAP Expression Vector Using EF-1α and SV40 Promoters

By using pSEAP2-control (Clontech) as a template, the SEAP gene was amplified by the PCR method (94° C. for 30 sec and 68° C. for 2 min×40 cycles) using the primers described in (2-1) and KOD-plus-. The amplified SEAP was prepared as an insert in the same manner as in (2-1). The insert was digested with the restriction enzymes NheI and BglII, and a vector pIRES puro3 (Clontech) was digested with the restriction enzymes NheI and BamHI, and pCMV/SEAP ires Puro was constructed in the same manner as in (2-1).

Subsequently, by using pEF1/V5-His A (Invitrogen) as a template, an EF-1a promoter was amplified by the PCR method (94° C. for 15 sec, 60° C. for 30 sec, and 68° C. for 2 min×30 cycles) using the following primers and KOD-plus-.

```
                                       (SEQ ID NO: 22)
5'-AAAACTAGTCAGAGAGGAATCTTTGCAGCTAATGGACC-3'

(SEQ ID NO: 23)
5'-AAAGATATCCCTAGCCAGCTTGGGTGGTACCAAGC-3'
```

By using the above-constructed pCMV/SEAP ires Puro as a vector, digestion with the restriction enzymes SpeI and EcoRV was performed for the vector and the promoter, and pEF/SEAP ires Puro was constructed according to the method described in (2-1).

Similarly, by using pcDNA3.1+(Invitrogen) as a template, an SV40 promoter was amplified by the PCR method (94° C. for 15 sec, 60° C. for 30 sec, and 68° C. for 1 min×30 cycles) using the following primers and KOD-plus-.

```
                                       (SEQ ID NO: 24)
5'-AAAACTAGTCTGTGGAATGTGTGTCAGTTAGGGTG-3'

(SEQ ID NO: 25)
5'-AAAGATATCAGCTTTTTGCAAAAGCCTAGGCCTC-3'
```

By using the above-constructed pCMV/SEAP ires Puro as a vector, digestion with the restriction enzymes SpeI and EcoRV was performed for the vector and the promoter, and pSV40/SEAP ires Puro was constructed according to the method described in (2-1).

(3-2) Cloning of DNA Element A2 or A7 Subsequently, cloning of the DNA element A2 or A7 was performed using pEF/SEAP ires Puro and pSV40/SEAP ires Puro constructed in (3-1) as basic structures.

First, pEF/SEAP ires Puro and pSV40/SEAP ires Puro were digested with the restriction enzyme SpeI for several hours, followed by ethanol precipitation, and the precipitate was dissolved in sterile water. By using the respective vectors digested with SpeI as templates, DNA for transformation was prepared by the PCR method (94° C. for 15 sec, 55° C. for 30 sec, and 68° C. for 10 min×30 cycles) using the following primers and KOD-plus-.

A2 (EF/D):

(SEQ ID NO: 26)
5'-GGAAATTGAGAAGTATCATTCACAACAGTACCACAAACATGAAA

TAAATGTGCTAGTCAGAGAGGAATCTTTGCAGC-3'

A2 (SV40/D):

(SEQ ID NO: 27)
5'-GGAAATTGAGAAGTATCATTCACAACAGTACCACAAACATGAAATA

AATGTGCTAGTCTGTGGAATGTGTGTCAGTTAG-3'

A2 (EF and SV40/R):

(SEQ ID NO: 28)
5'-CTCATTCTGTGGGTTGTCATTTCACTTCCTTGATGCTATCCTTTCA

AGCAAAATTTTAAAACTTTATCCATCTTTGCA-3'

A7 (EF/D):

(SEQ ID NO: 29)
5-CTTATTTTCTAAGTAGTATAGACTTAATTGTGAGAACAAAATAAAAA

CTTGCTAGTCAGAGAGGAATCTTTGCAGC-3'

A7 (SV40/D):

(SEQ ID NO: 30)
5'-CTTATTTTCTAAGTAGTATAGACTTAATTGTGAGAACAAAATAAAA

ACTTGCTAGTCTGTGGAATGTGTGTCAGTTAG-3'

A7 (EF and SV40/R):

(SEQ ID NO: 31)
5'-CTCTTCCCATTCTCATTTGAATCTACTTCAAAAGGTTTACCATACTA

AGAACTAGTTTTAAAACTTTATCCATCTTTGCA-3'

By using the thus prepared DNA for transformation and BAC transfected with pRed/ET, the DNA element A2 or A7 was cloned into the vector described in (3-1). The vector construct is shown in FIG. 2. Incidentally, the procedure was performed according to the method described in (2-2).

(3-3) Evaluation Using SEAP Expression as Index

Each plasmid constructed in (3-2) was evaluated using the host cell CHO-K1 (ATCC) and transfection reagent Lipofectamine 2000 (Invitrogen).

Antibiotic selection with puromycin at 8 μg/ml was performed for about 2 weeks starting 2 days after transfection, whereby a stably expressing polyclonal cell line was established. The thus established cell line was subjected to medium replacement on the day before measurement, and a given number of the cells were seeded into a 24-well plate. At 24 hours after plating the cells, the culture supernatant was collected, and the activity of SEAP was measured. The activity of SEAP in the culture supernatant was measured using SensoLyte™ pNPP Secreted Alkaline Phosphatase Reporter Assay (ANASPEC).

Figure 4A:
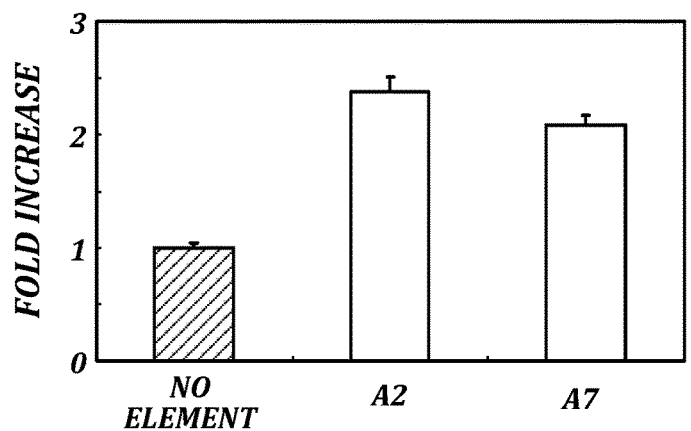
FIG. 4A and FIG. 4B comprise two graphs showing the expression of SEAP under the control of either an EF-1α (FIG. 4A) or an SV40 (FIG. 4B) promoter in a stably expressing CHO cell line either without a DNA element or with DNA element A2 or A7. The effects of DNA elements A2 and A7 on enhancement of expression were confirmed.
Figure 4B:
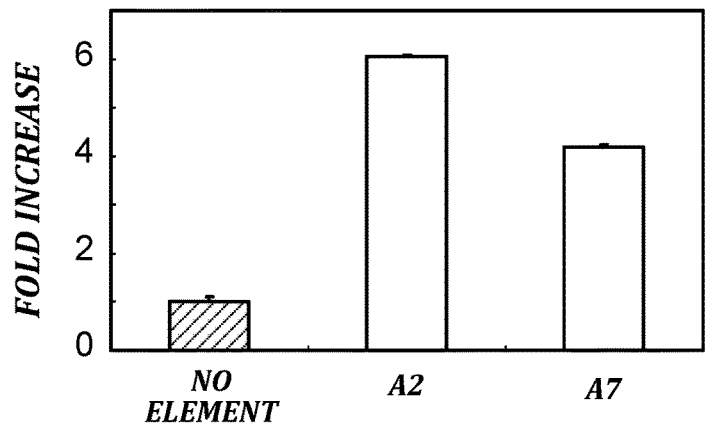

The measurement results are shown in FIG. 4. When the activity of SEAP of the control with no element was normalized to 1, the DNA element A2 or A7 exhibited an effect on enhancement of expression such that the activity of SEAP was twice or more as high in the case of use with the EF-1α promoter, and four times or more higher in the case of use with the SV40 promoter than that of the control. Based on the results, it was confirmed that these DNA elements exhibit the effect of enhancing foreign gene expression when used in combination with a general promoter.

Example 4

Evaluation Using Antibody Expression as Index (4-1) Construction of Human Light Chain Expression Vector pEF6KCL By using a plasmid pEF6/V5-HisB (Invitrogen) as a template, a DNA fragment between position 2174 (immediately downstream of BGHpA) and position 2958 (SmaI) (a DNA fragment containing an f1 origin of replication and SV40 promoter and origin, hereinafter referred to as "fragment A", the polynucleotide sequence of fragment A being represented by SEQ ID NO:6 in the Sequence Listing) was obtained by the PCR method using the following primers and KOD-plus-.

(SEQ ID NO: 32)
5'-CCACGCGCCCTGTAGCGGCGCATTAAGC-3'

(SEQ ID NO: 33)
5'-AAACCCGGGAGCTTTTTGCAAAAGCCTAGG-3'

The obtained fragment A and a DNA fragment containing a DNA sequence encoding a human κ chain secretory signal, a human κ chain constant region, and a human poly(A) addition signal (hereinafter referred to as "fragment B") were ligated by overlapping PCR. The thus obtained DNA fragment in which fragment A and fragment B were ligated was digested with the restriction enzymes KpnI and SmaI, and the resulting fragment was ligated to plasmid pEF6/V5-HisB (Invitrogen) which was digested with the restriction enzymes KpnI and SmaI, whereby a human light chain expression vector pEF6KCL having a signal sequence, a cloning site, a human κ chain constant region, and a human poly(A) addition signal sequence downstream of the EF-1α promoter was constructed.

A DNA fragment obtained by cleaving the pEF6KCL obtained by the above-mentioned method with the restriction enzymes KpnI and SmaI was ligated to pEF1/myc-HisB (Invitrogen) which was digested with KpnI and SmaI, followed by transformation alkaline lysis, and its sequence confirmation, whereby a plasmid pEF1KCL was constructed.

(4-2) Construction of Human Heavy Chain Expression Vector pEF1FCCU

A DNA fragment (the polynucleotide sequence of this DNA fragment is represented by SEQ ID NO: 7 in the Sequence Listing) containing a DNA sequence encoding a human IgG1 signal sequence and a constant region amino acid sequence was digested with the restriction enzymes NheI and PmeI, and the resulting fragment was ligated to plasmid pEF1KCL which was digested with NheI and PmeI, whereby a human heavy chain expression vector pEF1FCCU having a signal sequence, a cloning site, a human heavy chain constant region, and a human poly(A) addition signal sequence downstream of the EF-1α promoter was constructed.

(4-3) Construction of Single Humanized Antibody Gene X Expression Vector (Humanized Antibody Gene X/pEF_LHN #)

By ligating the L-chain or H-chain expression vector constructed in (4-1) or (4-2), a single humanized antibody expression vector (pEF_LHN (lacking a variable region)) was constructed.

A restriction enzyme SalI site was added by the PCR method to both ends of the gene expression unit from upstream of the promoter to downstream of poly(A) of pEF1KCL. Agarose gel electrophoresis, cutting out of a desired DNA fragment from the gel, and purification of the DNA fragment were then performed, whereby an insert was prepared. By digesting the pEF1FCCU constructed in (4-2) with the restriction enzyme SalI, the vector was linearized at the SalI site located upstream of the gene expression unit. Then, the linearized vector was ligated to the above insert, followed by transformation, alkaline lysis, and sequence confirmation, whereby a single humanized antibody expression vector (pEF_LHN (lacking a variable region)) was constructed.

Subsequently, the following oligonucleotides were introduced into an AatII site of the vector pEF_LHN (lacking a variable region).

(SEQ ID NO: 34)
5'-CGCGGCCGCACTAGTGACGT-3'

(SEQ ID NO: 35)
5'-CACTAGTGCGGCCGCGACGT-3'

The respective oligonucleotides were diluted to 5 pmol, and by using T4 Polynucleotide Kinase (TAKARA), a reaction was allowed to proceed at 37° C. for 1 hour. Then, 10× buffer (TAKARA) was added thereto, and annealing was performed at 96° C. for 1 minute at room temperature. These oligonucleotides and the vector pEF_LHN which was digested with the restriction enzyme AatII were ligated, followed by transformation, alkaline lysis, and sequence confirmation, whereby pEF_LHN # (lacking a variable region) was constructed.

By integrating a variable region of the humanized antibody gene X into the above-constructed universal vector (pEF_LHN # (lacking a variable region)), the construction of a humanized antibody gene X expression single vector (humanized antibody gene X/pEF_LHN #) was completed.

First, by using the following primers and KOD-plus-, an L-chain variable region of the humanized antibody gene X was amplified by the PCR method (94° C. for 15 sec, 55° C. for 30 sec, and 68° C. for 1 min×30 cycles).

L-Chain Variable Region:

(SEQ ID NO: 36)
5'-AAACATATGGCGACATCCAGATGAC-3'

(SEQ ID NO: 37)
5'-AAACGTACGCTTGATCTCCACCTTGG-3'

The amplified L-chain variable region fragment and the universal vector (pEF_LHN # (lacking a variable region)) were digested with the restriction enzymes NdeI and BsiWI, followed by agarose gel electrophoresis, cutting out of a desired fragment from the gel, purification, ligation reaction, transformation, alkaline lysis, and sequence confirmation, whereby the L-chain variable region was integrated into the vector. In the same manner, by using the following primers and KOD-plus-, an H-chain variable region of the humanized antibody gene X was amplified by the PCR method (94° C. for 15 sec, 55° C. for 30 sec, and 68° C. for 1 min×30 cycles).

H-Chain Variable Region:

(SEQ ID NO: 38)
5'-AAAGCTGAGCCAGGTGCAGCTGCAGG-3'

(SEQ ID NO: 39)
5'-AAAGCTGAGCTCACGGTCACCAGGGTTC-3'

The amplified H-chain variable region fragment and the vector having the L-chain variable region inserted therein were digested with the restriction enzyme BlpI, followed by agarose gel electrophoresis, cutting out of a desired fragment from the gel, purification, ligation reaction, transformation, alkaline lysis, and sequence confirmation, whereby the H-chain variable region was integrated into the vector and a single humanized antibody gene X expression vector (humanized antibody gene X/pEF_LHN #) was constructed.

(4-4) Construction of Single Humanized Antibody Gene X Expression Vector (Humanized Antibody Gene X/pCMV_LHN #)

By using the single humanized antibody gene X expression vector (humanized antibody gene X/pEF_LHN #) constructed in (4-3) as a basic vector structure, another single humanized antibody gene X expression vector (humanized antibody gene X/pCMV_LHN #) was constructed by replacing the promoter according to the following procedure.

By using ORES puro3 as a template, a CMV promoter fragment was amplified by the PCR method (94° C. for 30 sec and 68° C. for 3 min×40 cycles) using the following primers and KOD-plus-.

Upstream of H-Chain:

(SEQ ID NO: 40)
5'-CTTTTGCAAAAAGCTTCGCGTTACATAACTTACGGTAAATGGCC-3'

(SEQ ID NO: 41)
5'-TTCATGGTGGCGCTAGCCCGCAGATATCGATCCGAGCTCGGTA-3'

Upstream of L-Chain:

(SEQ ID NO: 42)
5'-TGACGTCGACAAGCTTCGCGTTACATAACTTACGGTAAATGGCC-3'

(SEQ ID NO: 43)
5'-CTGGATGTCGCCATATGCGCCGGAGATCCACAGCAGCAGGGAGATGA

ACACCTGGGTCTGCAGCACCATGGTGGCGCTAGCCCGCAGATATCGATCC

GAGCTCGGTA-3'

To the PCR reaction solution, the restriction enzyme DpnI was added, and a reaction was allowed to proceed at 37° C. for 1 hour, followed by purification using miniElute reaction Cleanup kit (Qiagen), whereby a sample for use in In-Fusion was prepared. Meanwhile, the humanized antibody gene X/pEF_LHN # was digested with the restriction enzymes HindIII, NheI, NdeI, and FseI, followed by agarose gel electrophoresis, whereby two large fragments among the resulting fragments were separated. Each of the fragments was cut out from the gel, and the DNA was extracted from the gel, whereby a sample for use in In-Fusion was prepared. All the samples for use in In-Fusion were put together, and cloning was performed using In-Fusion™ Advantage PCR Cloning Kit (TAKARA), followed by transformation, alkaline lysis, and sequence confirmation, whereby a single humanized antibody gene X expression vector (humanized antibody gene X/pCMV_LHN #) was constructed.

(4-5) Cloning of DNA Element A7

A7 was selected from the 5 types of the DNA elements which were confirmed to have an effect of enhancing SEAP expression, and cloned into an antibody expression vector.

In the same manner as in (2-2), by using each of the humanized antibody gene X expression single vectors (humanized antibody gene X/pEF_LHN # and humanized antibody gene X/pCMV_LHN #) digested with the restriction enzyme NotI as a template, DNA for transformation was prepared by the PCR method (94° C. for 15 sec, 55° C. for 30 sec, and 68° C. for 11 min×30 cycles) which was performed using the following primers and KOD-plus-.

Humanized Antibody Gene X/pEF_LHN # D:

(SEQ ID NO: 44)
5'-CTCTTCCCATTCTCATTTGAATCTACTTCAAAAGGTTTACCATACTA

AGACTCGAGGCACTAGTGACGTCAGGTGGCACT-3'

Humanized Antibody Gene X/pEF_LHN # R:

(SEQ ID NO: 45)
5'-CTCTTCCCATTCTCATTTGAATCTACTTCAAAAGGTTTACCATACTA

AGAGCACTAGTGACGTCAGGTGGCACTTTTCGG-3'

Humanized Antibody Gene X/pCMV_LHN # D:
Humanized antibody gene X/pEF_LHN # D was used.
Humanized Antibody Gene X/pCMV_LHN # R:
Humanized antibody gene X/pEF_LHN # R was used.

Figure 5:
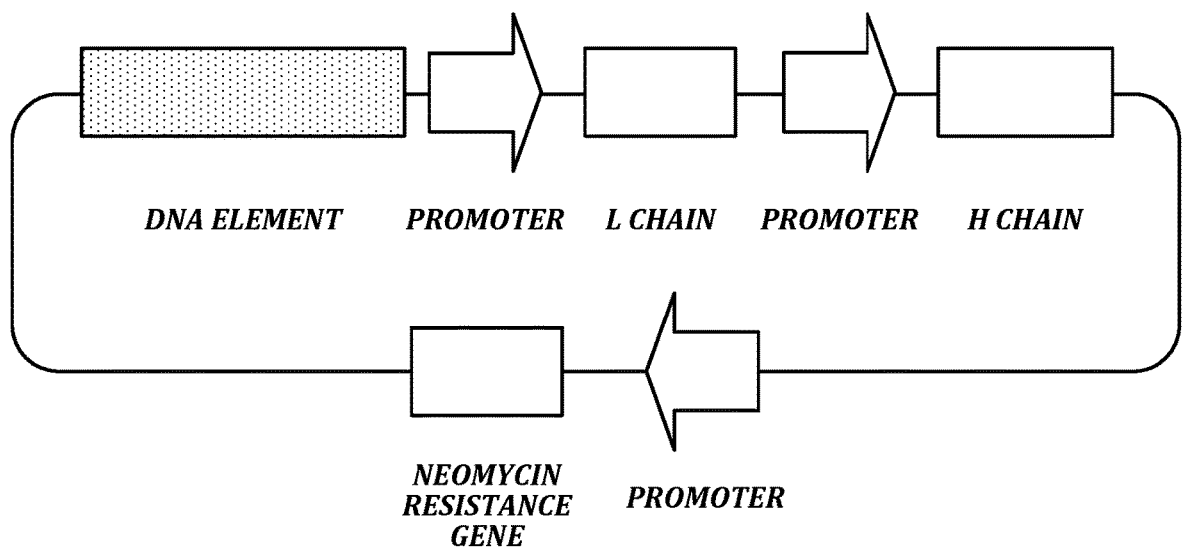
FIG. 5 is a schematic view of an antibody expression (antibody gene X heavy chain and light chain co-expression) vector into which a DNA element has been inserted.

By using the above-prepared DNA for transformation and BAC transfected with pRed/ET, the DNA element A7 was cloned into the single humanized antibody gene X expression vectors described in (4-3) and (4-4). The vector construct is shown in FIG. 5. Incidentally, the procedure was performed according to the method described in (2-2).

(4-6) Evaluation Using Antibody Expression as Index

Each plasmid constructed in (4-5) was evaluated using the host cell CHO-K1 (ATCC) and transfection reagent Lipofectamine 2000 (Invitrogen).

Antibiotic selection with Geneticin (Roche) at 800 µg/ml was performed for about 2 weeks starting 2 days after transfection, whereby a stably expressing polyclonal cell line was established. The thus established cell line was subjected to medium replacement on the day before measurement, and a given number of the cells were seeded into a 24-well plate. At 24 hours after plating the cells, the culture supernatant was collected, and the expression level of the antibody in the culture supernatant was measured by the ELISA method. Incidentally, the ELISA was performed as follows. To a 96-well plate coated with anti-kappa light chain at 50 ng/well, 100 µl of the cell-free culture supernatant was added to each well, and the plate was incubated at 37° C. for 1 hour. Subsequently, the sample (culture supernatant) was removed, and each well was washed with 200 µl of PBS-Tween (0.05%). Then, 100 µl of HRP-labeled anti-human IgG (Fc) was added to each well and the plate was incubated at 37° C. for an additional 1 hour. Thereafter, the HRP-labeled anti-human IgG (Fc) was removed, and each well was washed with PBS-Tween (0.05%). Then, a color was developed using a POD Substrate ABTS Kit (Nacalai), and an absorbance at a measurement wavelength of 405 nm was measured. For the dilution of the anti-kappa light chain, the anti-human IgG (Fc), and the sample, PBS-Tween (0.05%) was used. By using human IgG serially diluted to 12 ng, 6 ng, 3 ng, 1.5 ng, 0.75 ng, 0.375 ng, and 0.1875 ng as a standard, the concentration of the sample was calculated.

Figure 6A:
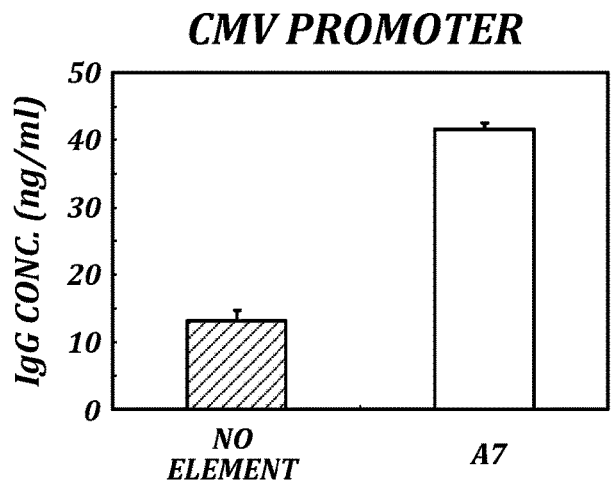
FIG. 6A and FIG. 6B comprise two graphs showing levels of secretion (measured by an ELISA method) of an antibody under the control of either a CMV (FIG. 6A) or an EF-1α (FIG. 6B) promoter in a stably expressing CHO cell line either without a DNA element or with DNA element A7. The effect of DNA element A7 on enhancement of expression was confirmed.
Figure 6B:
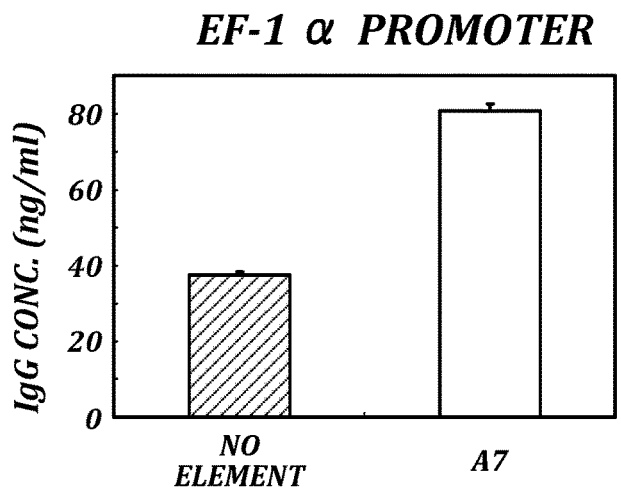
Figure 8A:
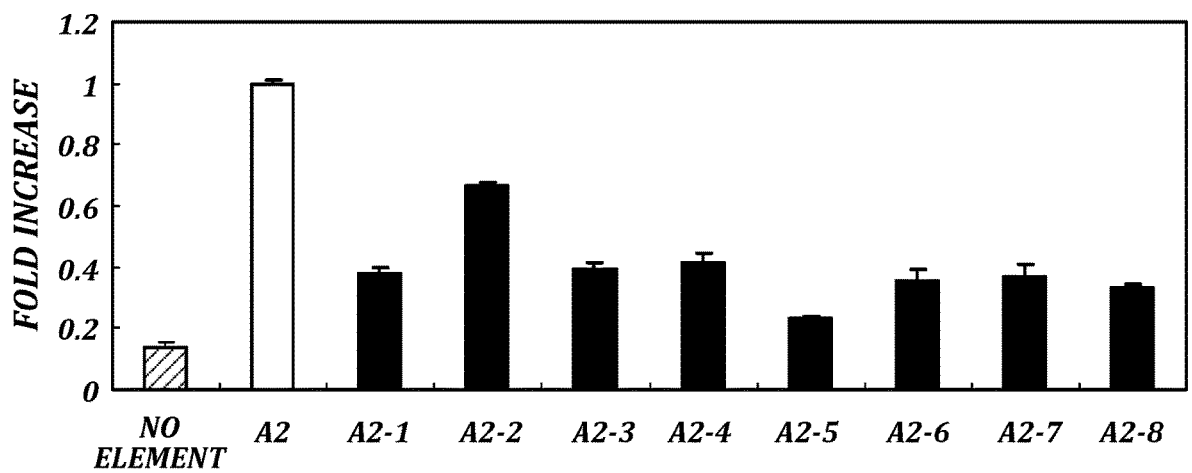
FIG. 8A through FIG. 8C comprise three graphs showing the expression of SEAP in a stably expressing CHO cell line either without a DNA element or with DNA element A2 or a related sequence.
Figure 8B:
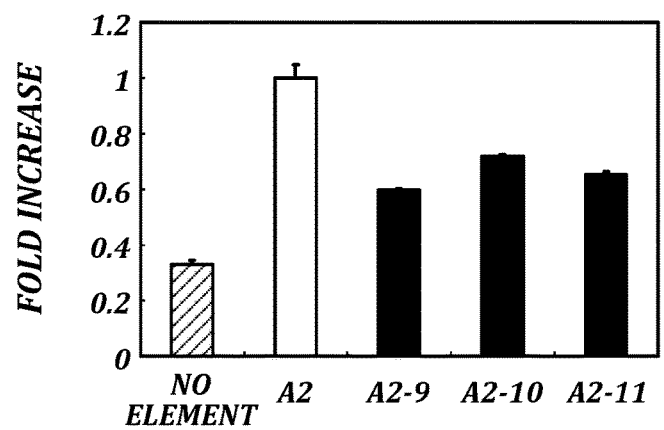
Figure 8C:
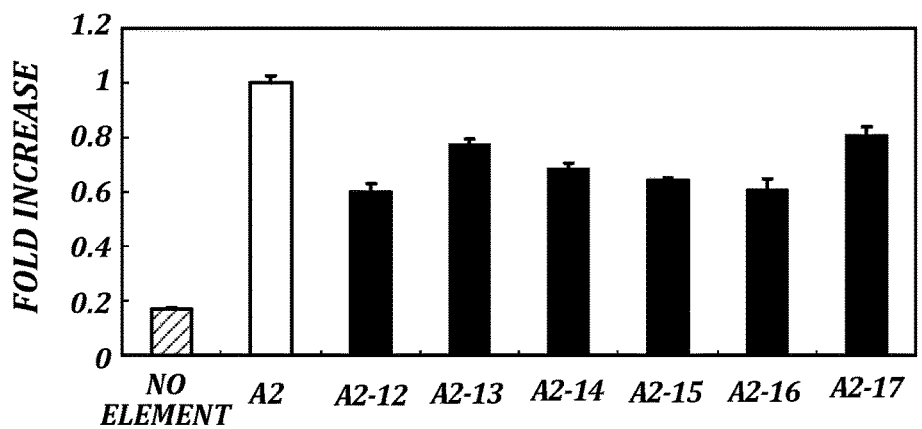
Figure 10A:
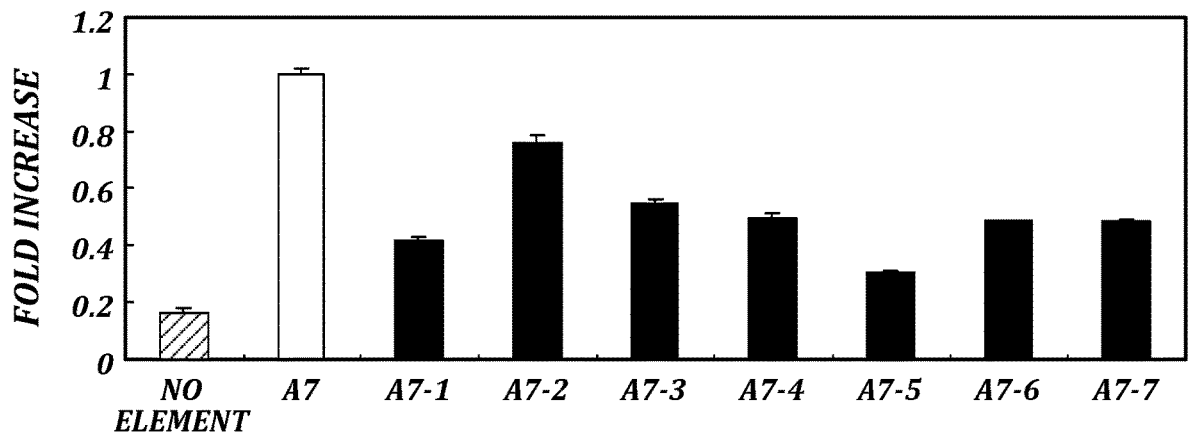
FIG. 10A through FIG. 10C comprise three graphs showing the expression of SEAP in a stably expressing CHO cell line either without a DNA element or with DNA element A7 or a related sequence.
Figure 10B:
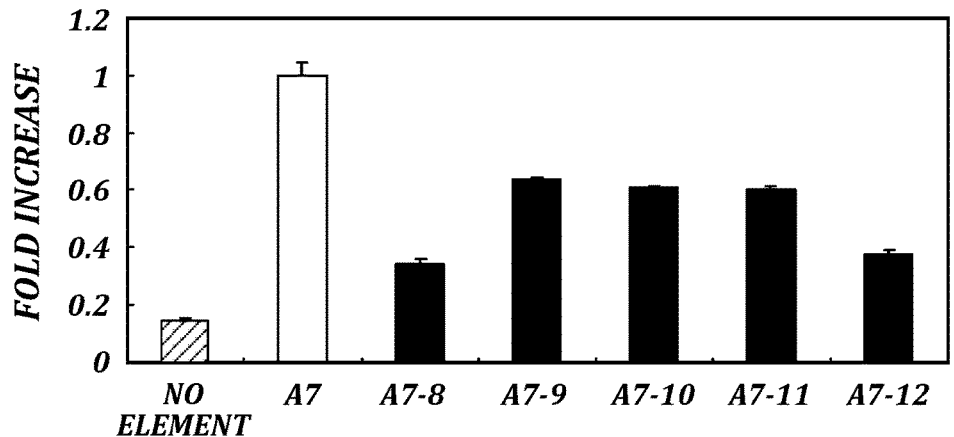
Figure 10C:
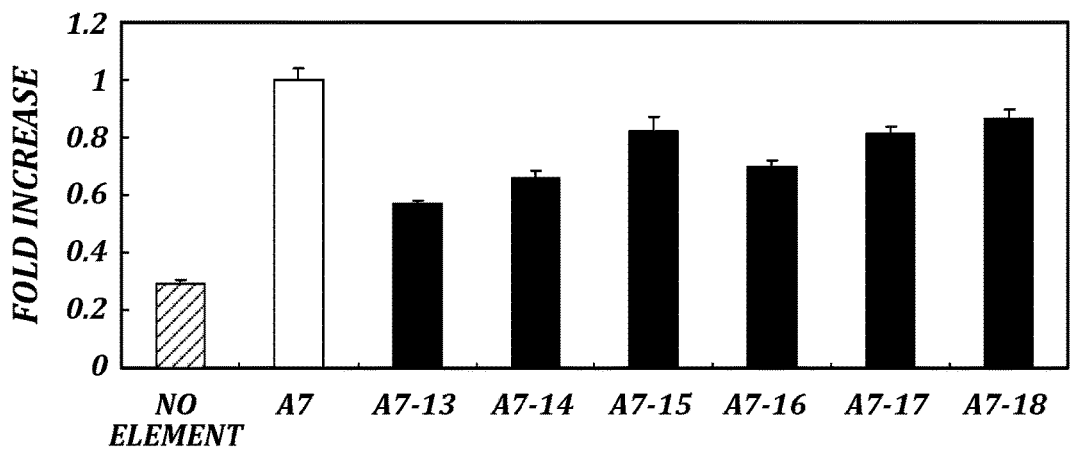
Figures 11, 12:
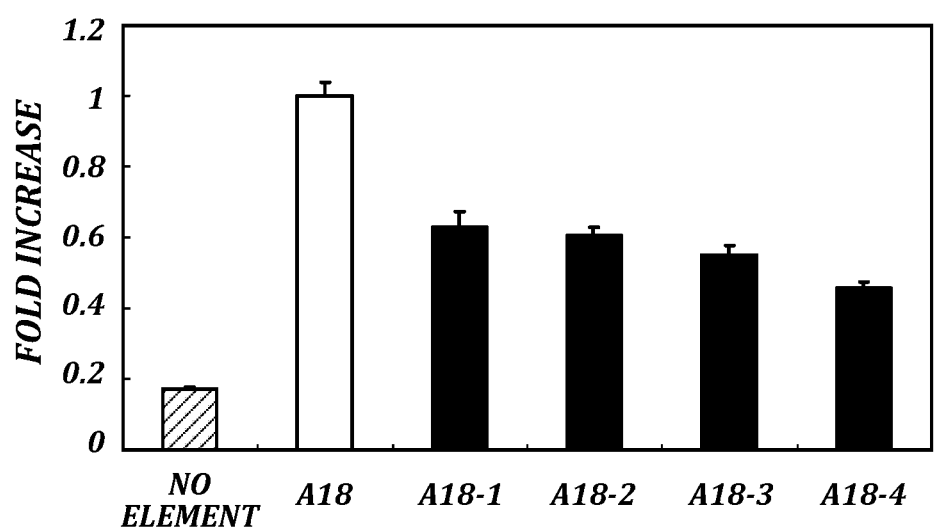
FIG. 11 is a table showing the sequence lengths of DNA element A18 and related sequences.
FIG. 12 is a graph showing the expression of SEAP in a stably expressing CHO cell line either without a DNA element or with DNA element A18 or a related sequence. The effects of DNA element A18 and related sequences on enhancement of expression were confirmed.
Figures 13, 14:
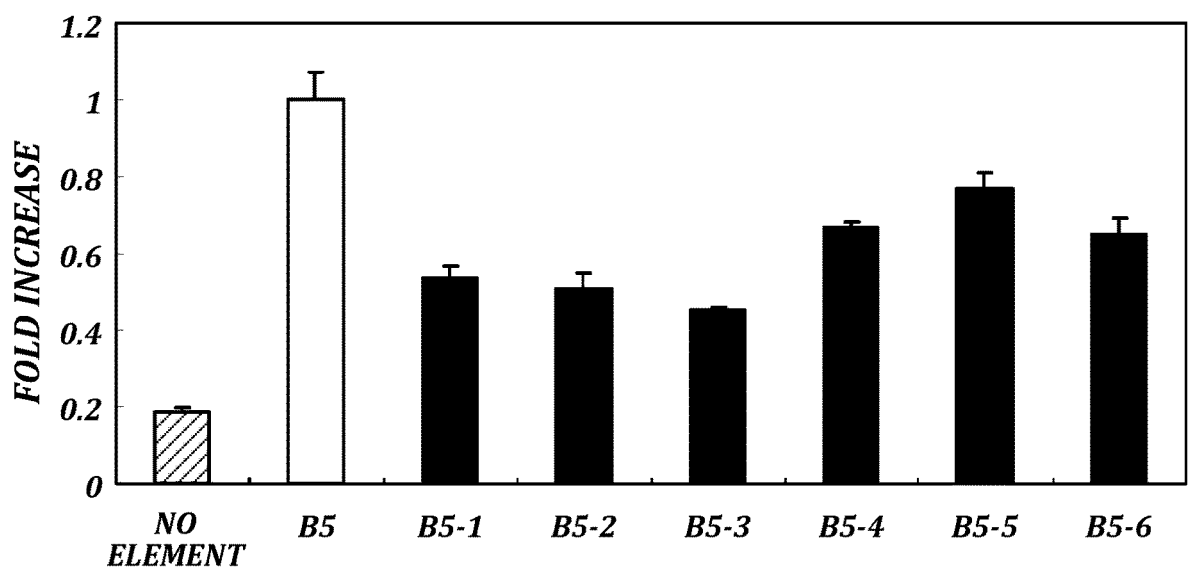
FIG. 13 is a table showing the sequence lengths of DNA element B5 and related sequences.
FIG. 14 is a graph showing the expression of SEAP in a stably expressing CHO cell line either without a DNA element or with DNA element B5 or a related sequence. The effects of DNA element B5 and related sequences on enhancement of expression were confirmed.
Figure 16A:
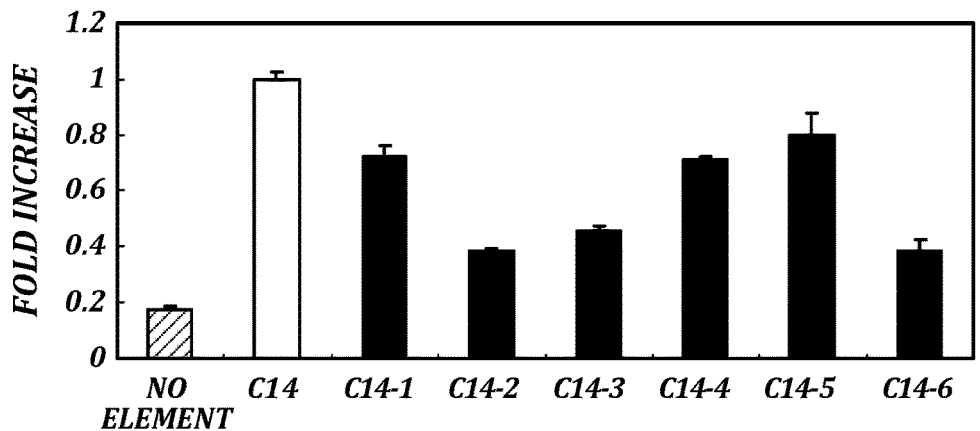
FIG. 16A through FIG. 16C comprise three graphs showing the expression of SEAP in a stably expressing CHO cell line either without a DNA element or with DNA element C14 or a related sequence.
Figure 16B:
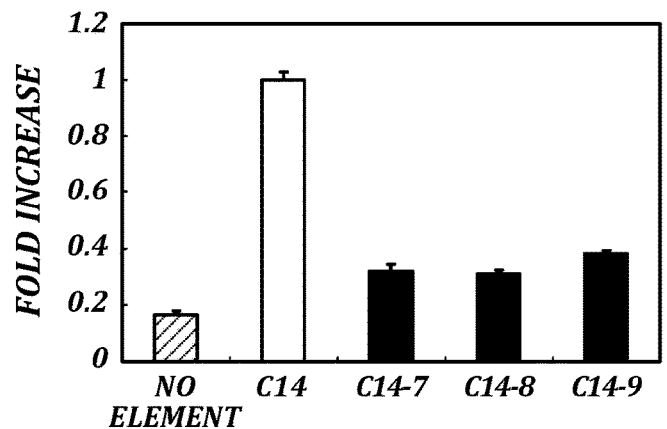
Figure 16C:
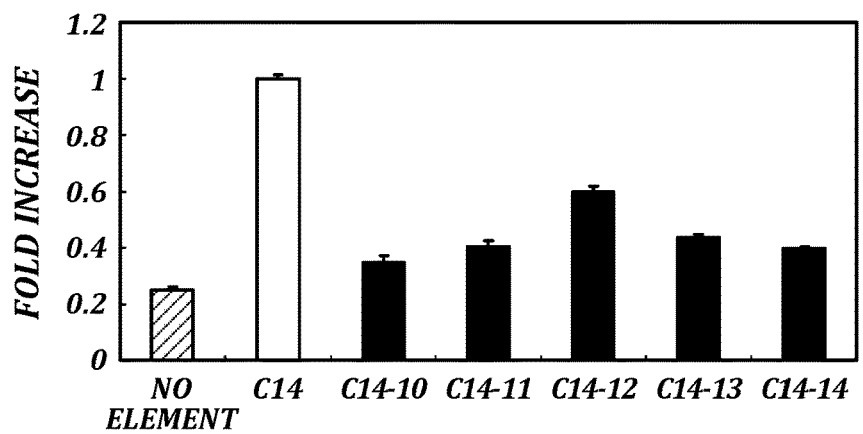

The results are shown in FIG. 6. It was confirmed that the sample having the DNA element A7 has a higher effect of enhancing antibody production as compared with a control with no element when the EF-1α promoter or the CMV promoter was used in the antibody expression vector.

Example 5

Length of Sequence Exhibiting Activity of Enhancing Foreign Gene Expression (5-1) Cloning of DNA Elements Having Different Sequence Lengths Based on the length of the sequence used in Example 2, vectors containing each of the DNA elements but having different sequence lengths were constructed.

The details of the DNA elements having different sequence lengths which were designed based on the full length of each of the DNA elements A2, A7, A18, B5, and C14 are shown in FIGS. 7, 9, 11, 13, 15, 18, and 19 respectively. The pCMV/SEAP ires Hygro described in (2-1) was digested with the restriction enzyme SpeI for several hours, followed by ethanol precipitation, and the precipitate was dissolved in sterile water. By using the vector digested with SpeI as a template, DNA for transformation was prepared by the PCR method (94° C. for 15 sec, 55° C. for 30 sec, and 68° C. for 10 min×30 cycles) using the following primers and KOD-plus-. By using the thus prepared DNA for transformation and the corresponding BAC transfected with pRed/ET, each DNA element having a different sequence length was cloned into the pCMV/SEAP ires Hygro described in (2-1). The vector construct is shown in FIG. 2. Incidentally, the procedure was performed according to the method described in (2-2).

A2-1D:

(SEQ ID NO: 46)
5'-CATGCACAGATTAGCCATTTAGTACTTACTAAATCAAACTCAATTTC

TGAAGTCTAGTTATTAATAGTAATCAATTACG-3'

A2-1R:

(SEQ ID NO: 47)
5'-CTCATTCTGTGGGTTGTCATTTCACTTCCTTGATGCTATCCTTTCA

AGCAAAATTCAATAATCAATGTCAACGCGTATAT-3'

A2-2D:

(SEQ ID NO: 48)
5'-ACACTGGTCAAAGGGACAGGTCATTGTTATGCTGGCAATGCAGGCT

GCTGAAAACTAGTTATTAATAGTAATCAATTACG-3'

A2-2R:

(SEQ ID NO: 49)
5'-ACTGTAGCTTCTTATTTTTTACCTGCAGTGCATTCCTGTAAAAGTAG

TGTGGAGTCAATAATCAATGTCAACGCGTATAT-3'

A2-3D:

(SEQ ID NO: 50)
5'-CTGGAAATTGAGAAGTATCATTCACAACAGTACCACAAACATGAAA
TAAATGTGCTAGTTATTAATAGTAATCAATTACG-3'

A2-3R:

(SEQ ID NO: 51)
5'-CCAAGCTTGTCCAACCGCGGCCTGCAGGCTGCATGCAGCCTGTGAA
GGCTTTGATCAATAATCAATGTCAACGCGTATAT-3'

A2-4D:

(SEQ ID NO: 52)
5'-TCAATCATTTATCAATTTTATCTTCAAAGTCCCTCACTTCAGGGAGA
TGATATACTAGTTATTAATAGTAATCAATTACG-3'

A2-4R:

(SEQ ID NO: 53)
5'-ATATATAAAAGTTCATGTATATATAAAATCATGCAATACACGGCCTT
TTGTGACTCAATAATCAATGTCAACGCGTATAT-3'

A2-5D:

(SEQ ID NO: 54)
5'-CGCATAAAAGGAAAAGCATCCTTAAAATAAACACCATCAATGGCTC
CTCGGTGGCTAGTTATTAATAGTAATCAATTACG-3'

A2-5R:
A2-4R was used.

A2-6D:

(SEQ ID NO: 55)
5'-GGGAGGCTACAGCTTGCCTCTCTAACCACTAAAAGGCATGACCCTC
CTCAAAGCTAGTTATTAATAGTAATCAATTACG-3'

A2-6R:
A2-4R was used.

A2-7D:

(SEQ ID NO: 56)
5'-TCTGGCTTCCCTGGGCCACGCTGGAAGAAGAATTGTCTTGCGCCAC
ACATAAAACTAGTTATTAATAGTAATCAATTACG-3'

A2-7R:

(SEQ ID NO: 57)
5'-AGCTGATTTTTACGTTAAATGTAACATGTAAAGAAATATATGTGTGT
TTTTAGATCAATAATCAATGTCAACGCGTATAT-3'

A2-8D:

(SEQ ID NO: 58)
5'-GTGAAGAGGAGGAGATGTCAAAATTCAAAGTCTTAAATGATGTAGT
TTTAAGTACTAGTTATTAATAGTAATCAATTACG-3'

A2-8R:

(SEQ ID NO: 59)
5'-ATGACACTTGATATTGTTGTTTATATTGCTGGTTAGTATGTGCCTT
CATTTACCTCAATAATCAATGTCAACGCGTATAT-3'

A2-9D:
A2-6D was used.
A2-9R:
A2R was used.
A2-10D:
A2-2D was used.
A2-10R:
A2-7R was used.
A2-11D:
A2-8D was used.
A2-11R:
A2-2R was used.
A2-12D:
A2-2D was used.
A2-12R:
A2-4R was used.
A2-13D:
A2-8D was used.
A2-13R:
A2-7R was used.
A2-14D:
A2D was used.
A2-14R:
A2-2R was used.
A2-15D:
A2-2D was used.
A2-15R:
A2R was used.
A2-16D:
A2-8D was used.
A2-16R:
A2-4R was used.
A2-17D:
A2D was used.
A2-17R:
A2-7R was used.

A7-1D:

(SEQ ID NO: 60)
5'-AAAAACAAAACTGGAGTAAACAAGATGAATTGTTTTAATAGAGGCA
CTGTATTACTAGTTATTAATAGTAATCAATTACG-3'

A7-1R:

(SEQ ID NO: 61)
5'-ATACAATGTTCCATGTATTCTGTGCCTGAACCTATGCAGCTGATGTA
GCTGAAGTCAATAATCAATGTCAACGCGTATAT-3'

A7-2D:

(SEQ ID NO: 62)
5'-GATCTTATTTTCTAAGTAGTATAGACTTAATTGTGAGAACAAAATAA
AAACTTGCTAGTTATTAATAGTAATCAATTACG-3'

A7-2R:

(SEQ ID NO: 63)
5'-TGTTGTTTTCAGCCACTAAGTTTGAGGTGATTTGTTCTGGCAGTCCT AGGAAACTCAATAATCAATGTCAACGCGTATAT-3'

A7-3D:
A7-2D was used.
A7-3R:

(SEQ ID NO: 64)
5'-AGCCTACACTACCCTTTGCAGCCTTTGGTAACTATCCTTCTGCTGT CTACCTCCTCAATAATCAATGTCAACGCGTATAT-3'

A7-4D:

(SEQ ID NO: 65)
5'-AGGAGCTCCTGAATGAAGGACATCACTCAGCTGTGTTAAGTATCTG GAACAATACTAGTTATTAATAGTAATCAATTACG-3'

A7-4R:

(SEQ ID NO: 66)
5'-GACATAAAATGTAAGATATGATATGCTATGTAAGATATGATACCTG CCTTAAAATCAATAATCAATGTCAACGCGTATAT-3'

A7-5D:

(SEQ ID NO: 67)
5'-CACTGCTTGATACTTACTGTGGACTTTGAAAATTATGAATGTGTGTG TGTGTGTCTAGTTATTAATAGTAATCAATTACG-3'

A7-5R:

(SEQ ID NO: 68)
5'-CAATTACATTCCAGTGATCTGCTACTTAGAATGCATGACTGAACTCC TGGGTGGTCAATAATCAATGTCAACGCGTATAT-3'

A7-6D:

(SEQ ID NO: 69)
5'-TTATTTTGAAGAGAAACTCCTGGTTCCCACTTAAAATCCTTTCTTGT TTCCAAGCTAGTTATTAATAGTAATCAATTACG-3'

A7-6R:

(SEQ ID NO: 70)
5'-AAGCAGTGTGTGTTTACCTGCATGTGTATGTGAATTAACTCTGTTCC TGAGGCATCAATAATCAATGTCAACGCGTATAT-3'

A7-7D:

(SEQ ID NO: 71)
5'-ATTGCATGTTCTCATTTATTTGTGGGATGTAAAAATCAAAACAATAG AACGTATCTAGTTATTAATAGTAATCAATTACG-3'

A7-7R:

(SEQ ID NO: 72)
5'-TTGGGAGGCCGCAGCTGGTAGATCACTTGAGGCCACGAATTTGACA CCAGCAGGTCAATAATCAATGTCAACGCGTATAT-3'

A7-8D:
A7-1D was used.
A7-8R:
A7R was used.
A7-9D:
A7-7D was used.
A7-9R:
A7-5R was used.
A7-10D:
A7-4D was used.
A7-10R:
A7-7R was used.
A7-11D:
A7-6D was used.
A7-11R:
A7-4R was used.
A7-12D:
A7-2D was used.
A7-12R:
A7-6R was used.
A7-13D:
A7-7D was used.
A7-13R:
A7R was used.
A7-14D:
A7-4D was used.
A7-14R:
A7-5R was used.
A7-15D:
A7-6D was used.
A7-15R:
A7-7R was used.
A7-16D:
A7-2D was used.
A7-16R:
A7-4R was used.
A7-17D:
A7-4D was used.
A7-17R:
A7R was used.
A7-18D:
A7-6D was used.
A7-18R
A7-5R was used.
A18-1:

(SEQ ID NO: 73)
5'-ATCCCCTGCTCTGCTAAAAAAGAATGGATGTTGACTCTCAGGCCCTA GTTCTTGATCCTATTAATAGTAATCAATTACG-3'

A18-1R:
A18R was used.
A18-2D:

(SEQ ID NO: 74)
5'-CTAAAGTGCTGGGATTACAGGCATAAGCCACCGTGCCCGGCTGGAG CATTGGGATCCTATTAATAGTAATCAATTACG-3'

A18-2R:

(SEQ ID NO: 75)
5'-ACTACTTACACATTTCGAGTTTTAAATAAGGCGTTCAATATAGAGTGAACACCTAGTCAATAATCAATGTCAACG-3'

A18-3D:

(SEQ ID NO: 76)
5'-CAGGCATAAGCCACCGCACCCGGCCACCCCTTACTAATTTTTAGTAACGTCGATCCTATTAATAGTAATCAATTACG-3'

A18-3R:

(SEQ ID NO: 77)
5'-CTGATTGACTTTGACCTCTGCTTTCCAACTTTGCCCCAAAGAAAGTTAGTCACCTAGTCAATAATCAATGTCAACG-3'

A18-4D:
A18-3D was used.
A18-4R:

(SEQ ID NO: 78)
5'-TTCAATGAAACAAGCTCTGTGAGGCTCATTTGTACCCATTTTGTTCAGTACTGCCTAGTCAATAATCAATGTCAACG-3'

B5-1D:

(SEQ ID NO: 79)
5'-ACATACCCAGAGACACTGAGAGAGACAGACAGACAGTAAACAGAGGAGCACGATCCTATTAATAGTAATCAATTACG-3'

B5-1R:
B5R was used.
B5-2D:

(SEQ ID NO: 80)
5'-GCTCAATTGTATCTTATGAAAACAATTTTTCAAAATAAAACAAGAGATATGATCCTATTAATAGTAATCAATTACG-3'

B5-2R:
B5R was used.
B5-3D:

(SEQ ID NO: 81)
5'-CCTGTGCTGAATACCGTCTGCATATGTATAGGAAAGGGTTAACTCAGCAGGGATCCTATTAATAGTAATCAATTACG-3'

B5-3R:

(SEQ ID NO: 82)
5'-TATGTGAATGGAAATAAAATAATCAAGCTTGTTAGAATTGTGTTCATAATGACCCTAGTCAATAATCAATGTCAACG-3'

B5-4D:
B5D was used.
B5-4R:

(SEQ ID NO: 83)
5'-GAAAGTCTACAATTTTTTCAGTTTAAAATGGTATTTATTTGTAACATGTACCCTAGTCAATAATCAATGTCAACG-3'

B5-5D:
B5-1D was used.
B5-5R:

(SEQ ID NO: 84)
5'-CAAAGATGAAGGATGAGAGTGACTTCTGCCTTCATTATGTTATGTGTTCATATCCTAGTCAATAATCAATGTCAACG-3'

B5-6D:

(SEQ ID NO: 85)
5'-CAGTGAATTATTCACTTTGTCTTAGTTAAGTAAAAATAAAATCTGACTGTGATCCTATTAATAGTAATCAATTACG-3'

B5-6R:

(SEQ ID NO: 86)
5'-GAACAGACAGGTGAATGAGCACAGAGGTCATTTGTAAACCGTTTGTGGTTAGCCTAGTCAATAATCAATGTCAACG-3'

C14-1D:

(SEQ ID NO: 87)
5'-CTTTTTGGCTTCTGTGTTTAAGTTATTTTTCCCCTAGGCCCACAAACAGAGTCGATCCTATTAATAGTAATCAATTACG-3'

C14-1R:

(SEQ ID NO: 88)
5'-AACCTTGGAAAAATTCTGTTGTGTTTAGAAGCATGTACCAATCTATCACTCCTAGTCAATAATCAATGTCAACG-3'

C14-2D:

(SEQ ID NO: 89)
5'-CTATTCACTGTCTGTAGGATGAAAAAGTTAATAACACCCTGAGAGGTTTCGATCCTATTAATAGTAATCAATTACG-3'

C14-2R:

(SEQ ID NO: 90)
5'-CCTTAGATTAGTTTATTGTATTTTTTATCAGCTACTATAAGGTTTACACACCCTAGTCAATAATCAATGTCAACG-3'

C14-3D:

(SEQ ID NO: 91)
5'-CAAGACCCTCAAAATTCAAAAATTTCCTTTATCTTGCTGTAGCACCTCCTGCGATCCTATTAATAGTAATCAATTACG-3'

C14-3R:

5'-GGAGGGGATAGGAAGGGGATGAGGCCTAACAGGTTGATGATCTA (SEQ ID NO: 92)

GGCTTTACCTAGTCAATAATCAATGTCAACG-3'

C14-4D:

5'-CTCAAAAAGGAGATAATTCCAGCCCCTCGCCTTAAAGAATCCCT (SEQ ID NO: 93)

ATCAAGTGATCCTATTAATAGTAATCAATTACG-3'

C14-4R:
C14-1R was used.
C14-5D:

5'-CGCTTGAACCTGGGAGGCAGAGGTTGCAGTGAGCCGAGATCACG (SEQ ID NO: 94)

CCGTTGGATCCTATTAATAGTAATCAATTACG-3'

C14-5R:
C14-1R was used.
C14-6D:
C14-4D was used.
C14-6R:

5'-TTAACTTTTTCATCCTACAGACAGTGAATAGTAAAGCTTTCTGT (SEQ ID NO: 95)

GAAGACATACCCTAGTCAATAATCAATGTCAACG-3'

C14-7D:
C14-2D was used.
C14-7R:
C14-1R was used.
C14-8D:
C14-3D was used.
C14-8R:

5'-AAATTATTTCCTGGTGGGCAATATTAGAATATGGGGAATGTTTG (SEQ ID NO: 96)

CTTCTGAGCCTAGTCAATAATCAATGTCAACG-3'

C14-9D:
C14-4D was used.
C14-9R:
C14-3R was used.
C14-10D:
C14-2D was used.
C14-10R:
C14R was used.
C14-11D:
C14-3D was used.
C14-11R:
C14-2R was used.
C14-12D:
C14-4D was used.
C14-12R:
C14-8R was used.
C14-13D:
C14-3D was used.
C14-13R:
C14-1R was used.
C14-14D:

C14-4D was used.
C14-14R:
C14-2R was used.

As for the polynucleotide sequences of the respective fragments of A2, A2-1 corresponds to the polynucleotide sequence of nucleotides 1 to 3000 of SEQ ID NO:1 in the Sequence Listing; A2-2 corresponds to the polynucleotide sequence of nucleotides 2801 to 5800 of SEQ ID NO:1 in the Sequence Listing; A2-3 corresponds to the polynucleotide sequence of nucleotides 5401 to 8450 of SEQ ID NO:1 in the Sequence Listing; A2-4 corresponds to the polynucleotide sequence of nucleotides 701 to 2700 of SEQ ID NO:1 in the Sequence Listing; A2-5 corresponds to the polynucleotide sequence of nucleotides 701 to 2200 of SEQ ID NO:1 in the Sequence Listing; A2-6 corresponds to the polynucleotide sequence of nucleotides 701 to 3700 of SEQ ID NO:1 in the Sequence Listing; A2-7 corresponds to the polynucleotide sequence of nucleotides 2001 to 5000 of SEQ ID NO:1 in the Sequence Listing; A2-8 corresponds to the polynucleotide sequence of nucleotides 4001 to 7000 of SEQ ID NO:1 in the Sequence Listing; A2-9 corresponds to the polynucleotide sequence of nucleotides 1 to 3700 of SEQ ID NO: 1 in the Sequence Listing; A2-10 corresponds to the polynucleotide sequence of nucleotides 2001 to 5800 of SEQ ID NO:1 in the Sequence Listing; A2-11 corresponds to the polynucleotide sequence of nucleotides 2801 to 7000 of SEQ ID NO:1 in the Sequence Listing; A2-12 corresponds to the polynucleotide sequence of nucleotides 701 to 5800 of SEQ ID NO: 1 in the Sequence Listing; A2-13 corresponds to the polynucleotide sequence of nucleotides 2001 to 7000 of SEQ ID NO:1 in the Sequence Listing; A2-14 corresponds to the polynucleotide sequence of nucleotides 2801 to 8450 of SEQ ID NO:1 in the Sequence Listing; A2-15 corresponds to the polynucleotide sequence of nucleotides 1 to 5800 of SEQ ID NO:1 in the Sequence Listing; A2-16 corresponds to the polynucleotide sequence of nucleotides 701 to 7000 of SEQ ID NO:1 in the Sequence Listing; and A2-17 corresponds to the polynucleotide sequence of nucleotides 2001 to 8450 of SEQ ID NO:1 in the Sequence Listing.

As for the polynucleotide sequences of the respective fragments of A7, A7-1 corresponds to the polynucleotide sequence of nucleotides 601 to 3600 of SEQ ID NO:2 in the Sequence Listing; A7-2 corresponds to the polynucleotide sequence of nucleotides 3601 to 8420 of SEQ ID NO:2 in the Sequence Listing; A7-3 corresponds to the polynucleotide sequence of nucleotides 5401 to 8420 of SEQ ID NO:2 in the Sequence Listing; A7-4 corresponds to the polynucleotide sequence of nucleotides 3401 to 6400 of SEQ ID NO:2 in the Sequence Listing; A7-5 corresponds to the polynucleotide sequence of nucleotides 1501 to 4500 of SEQ ID NO:2 in the Sequence Listing; A7-6 corresponds to the polynucleotide sequence of nucleotides 4401 to 7400 of SEQ ID NO:2 in the Sequence Listing; A7-7 corresponds to the polynucleotide sequence of nucleotides 2401 to 5400 of SEQ ID NO:2 in the Sequence Listing; A7-8 corresponds to the polynucleotide sequence of nucleotides 1 to 3600 of SEQ ID NO:2 in the Sequence Listing; A7-9 corresponds to the polynucleotide sequence of nucleotides 1501 to 5400 of SEQ ID NO:2 in the Sequence Listing; A7-10 corresponds to the polynucleotide sequence of nucleotides 2401 to 6400 of SEQ ID NO:2 in the Sequence Listing; A7-11 corresponds to the polynucleotide sequence of nucleotides 3401 to 7400 of SEQ ID NO: 2 in the Sequence Listing; A7-12 corresponds to the polynucleotide sequence of nucleotides 4401 to 8420 of SEQ ID NO:2 in the Sequence Listing; A7-13 corresponds to the polynucleotide sequence of nucleotides 1 to 5400 of SEQ ID NO:2 in the Sequence Listing; A7-14 corresponds to the polynucleotide sequence of nucleotides 1501 to 6400 of SEQ ID NO:2 in the Sequence Listing; A7-15 corresponds to the polynucleotide sequence of nucleotides 2401 to 7400 of SEQ ID NO:2 in the Sequence Listing; A7-16 corresponds to the polynucleotide sequence of nucleotides 3401 to 8420 of SEQ ID NO:2 in the Sequence Listing; A7-17 corresponds to the polynucleotide sequence of nucleotides 1 to 6400 of SEQ ID NO:2 in the Sequence Listing; and A7-18 corresponds to the polynucleotide sequence of nucleotides 1501 to 7400 of SEQ ID NO:2 in the Sequence Listing.

As for the polynucleotide sequences of the respective fragments of A18, A18-1 corresponds to the polynucleotide sequence of nucleotides 1 to 5040 of SEQ ID NO:3 in the Sequence Listing; A18-2 corresponds to the polynucleotide sequence of nucleotides 1001 to 6002 of SEQ ID NO:3 in the Sequence Listing; A18-3 corresponds to the polynucleotide sequence of nucleotides 2001 to 7000 of SEQ ID NO:3 in the Sequence Listing; and A18-4 corresponds to the polynucleotide sequence of nucleotides 3000 to 7000 of SEQ ID NO:3 in the Sequence Listing.

As for the polynucleotide sequences of the respective fragments of B5, B5-1 corresponds to the polynucleotide sequence of nucleotides 1 to 4001 of SEQ ID NO:4 in the Sequence Listing; B5-2 corresponds to the polynucleotide sequence of nucleotides 1 to 3200 of SEQ ID NO:4 in the Sequence Listing; B5-3 corresponds to the polynucleotide sequence of nucleotides 2491 to 5601 of SEQ ID NO:4 in the Sequence Listing; B5-4 corresponds to the polynucleotide sequence of nucleotides 5373 to 8401 of SEQ ID NO:4 in the Sequence Listing; B5-5 corresponds to the polynucleotide sequence of nucleotides 901 to 4001 of SEQ ID NO:4 in the Sequence Listing; and B5-6 corresponds to the polynucleotide sequence of nucleotides 4001 to 7000 of SEQ ID NO:4 in the Sequence Listing.

As for the polynucleotide sequences of the respective fragments of C14, C14-1 corresponds to the polynucleotide sequence of nucleotides 960 to 4015 of SEQ ID NO:5 in the Sequence Listing; C14-2 corresponds to the polynucleotide sequence of nucleotides 1987 to 5014 of SEQ ID NO:5 in the Sequence Listing; C14-3 corresponds to the polynucleotide sequence of nucleotides 4020 to 7119 of SEQ ID NO:5 in the Sequence Listing; C14-4 corresponds to the polynucleotide sequence of nucleotides 960 to 8141 of SEQ ID NO:5 in the Sequence Listing; C14-5 corresponds to the polynucleotide sequence of nucleotides 960 to 6011 of SEQ ID NO:5 in the Sequence Listing; C14-6 corresponds to the polynucleotide sequence of nucleotides 4939 to 8141 of SEQ ID NO:5 in the Sequence Listing; C14-7 corresponds to the polynucleotide sequence of nucleotides 960 to 5014 of SEQ ID NO:5 in the Sequence Listing; C14-8 corresponds to the polynucleotide sequence of nucleotides 2994 to 7119 of SEQ ID NO:5 in the Sequence Listing; C14-9 corresponds to the polynucleotide sequence of nucleotides 4020 to 8141 of SEQ ID NO:5 in the Sequence Listing; C14-10 corresponds to the polynucleotide sequence of nucleotides 1 to 5014 of SEQ ID NO:5 in the Sequence Listing; C14-11 corresponds to the polynucleotide sequence of nucleotides 1987 to 7119 of SEQ ID NO:5 in the Sequence Listing; C14-12 corresponds to the polynucleotide sequence of nucleotides 2994 to 8141 of SEQ ID NO:5 in the Sequence Listing; C14-13 corresponds to the polynucleotide sequence of nucleotides 960 to 7119 of SEQ ID NO: 5 in the Sequence Listing; and C14-14 corresponds to the polynucleotide sequence of nucleotides 1987 to 8141 of SEQ ID NO:5 in the Sequence Listing.

The start and end points of the respective fragments on the full-length sequence are also shown in FIGS. 18 and 19.

(5-2) Evaluation of DNA Elements Having Different Sequence Lengths

Each plasmid constructed in (5-1) was evaluated using the host cell CHO-K1 (ATCC) and transfection reagent Lipofectamine 2000 (Invitrogen).

In the same manner as in (2-3), antibiotic selection with hygromycin was performed after transfection, whereby a stably expressing polyclonal cell line was established. The thus established cell line was subjected to medium replacement on the day before measurement, and a given number of the cells were seeded into a 24-well plate. At 24 hours after plating the cells, the culture supernatant was collected, and the activity of SEAP was measured.

The measurement results are shown in FIGS. 8, 10, 12, 14, and 16. It was confirmed that not only the full-length DNA element, but also clones having a sequence length shorter than the full length have an effect of enhancement of expression. Based on the results, it was confirmed that the DNA elements A2, A7, A18, B5, and C14 have an activity of enhancing foreign gene expression even cases where they have a sequence length shorter than the full length. However, they exhibit the highest effect when the sequence length is the full length.

Example 6

Effect Using Host Cells Other than CHO Cell Line

A CHO cell line was used as the cell line in the evaluation in Examples 2 to 5. However, in Example 6 an HEK293 cell line was selected as a cell line other than the CHO cell line. The HEK293 cell line was subjected to static culture at 37° C. in the presence of 5% $CO_2$ using DMEM medium (Invitrogen) containing 10% FCS, and a given number of the cells were seeded into a 6-well plate on the day before transfection. In order to evaluate the SEAP expression vector containing each DNA element constructed in (3-2), transfection was performed using each plasmid and transfection reagent Lipofectamine 2000 (Invitrogen). Antibiotic selection with hygromycin was performed for about 2 weeks starting 2 days after transfection, whereby a stably expressing polyclonal cell line was established. The thus established cell line was subjected to medium replacement on the day before measurement, and a given number of the cells were seeded into a 24-well plate. At 24 hours after plating the cells, the culture supernatant was collected, and the activity of SEAP was measured. The activity of SEAP in the culture supernatant was measured using SensoLyte™ pNPP Secreted Alkaline Phosphatase Reporter Assay (ANASPEC).

Figure 17:
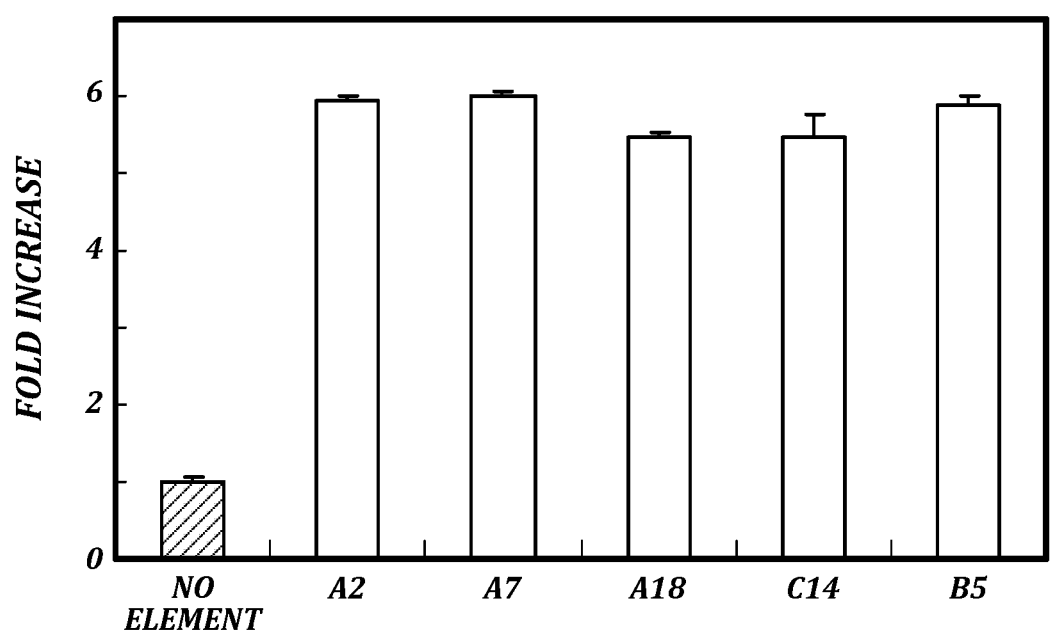
FIG. 17 is a graph showing the expression of SEAP in a stably expressing HEK293 cell line either without a DNA element or with DNA element A2, A7, A18, B5, or C14. The effects of DNA elements A2, A7, A18, B5, and C14 on enhancement of expression in HEK293 cells were confirmed.

The measurement results are shown in FIG. 17. In the same manner as in Example 3, it was confirmed that each element is also highly effective in enhancing the expression of a foreign gene (SEAP) in the HEK293 cell line.

INDUSTRIAL APPLICABILITY

By introducing a foreign gene expression vector using the DNA element according to the invention into mammalian host cells, it becomes possible to improve the productivity of a foreign gene of a therapeutic protein, an antibody, or the like.

The invention claimed is:

1. A foreign gene expression vector comprising a polynucleotide consisting of a polynucleotide selected from (a) to (h):
   (a) a polynucleotide consisting of the nucleotide sequence of SEQ ID NO:3;
   (b) a polynucleotide having at least 3000 consecutive nucleotides of the nucleotide sequence of SEQ ID NO:3;
   (c) a polynucleotide having at least 2000 consecutive nucleotides of the nucleotide sequence of SEQ ID NO:3;
   (d) a polynucleotide having at least 1500 consecutive nucleotides of the nucleotide sequence of SEQ ID NO:3;
   (e) a polynucleotide consisting of nucleotides 1 to 5040 of the nucleotide sequence of SEQ ID NO:3;
   (f) a polynucleotide consisting of nucleotides 1001 to 6002 of the nucleotide sequence of SEQ ID NO:3;
   (g) a polynucleotide consisting of nucleotides 2001 to 7000 of the nucleotide sequence of SEQ ID NO:3; and
   (h) a polynucleotide consisting of nucleotides 3000 to 7000 of the nucleotide sequence of SEQ ID NO:3;
   wherein said polynucleotide enhances foreign gene expression as compared to a foreign gene expression vector without the polynucleotide.

2. The foreign gene expression vector according to claim 1, wherein the foreign gene encodes a protein that is a multimeric protein.

3. The foreign gene expression vector according to claim 2, wherein the protein encoded by the foreign gene is a hetero-multimeric protein.

4. The foreign gene expression vector according to claim 3, wherein the protein encoded by the foreign gene is an antibody or a functional fragment thereof.

5. A transformed cell into which the foreign gene expression vector according to claim 1 has been introduced.

6. The transformed cell according to claim 5, wherein the cell is a cultured cell derived from a mammal.

7. The transformed cell according to claim 6, wherein the cultured cell derived from a mammal is a cell selected from COS-1 cells, 293 cells, or CHO cells.

8. The transformed cell according to claim 5, wherein the foreign gene encodes a protein that is a multimeric protein.

9. The transformed cell according to claim 8, wherein the protein encoded by the foreign gene is a hetero-multimeric protein.

10. The transformed cell according to claim 9, wherein the protein encoded by the foreign gene is an antibody or a functional fragment thereof.

11. A foreign gene expression vector comprising a polynucleotide consisting of (i) and (ii):
   (i) at least one sequence selected from (a) to (h):
      (a) a polynucleotide consisting of the nucleotide sequence of SEQ ID NO:3;
      (b) a polynucleotide having at least 3000 consecutive nucleotides of the nucleotide sequence of SEQ ID NO:3;
      (c) a polynucleotide having at least 2000 consecutive nucleotides of the nucleotide sequence of SEQ ID NO:3;
      (d) a polynucleotide having at least 1500 consecutive nucleotides of the nucleotide sequence of SEQ ID NO:3;
      (e) a polynucleotide consisting of nucleotides 1 to 5040 of the nucleotide sequence of SEQ ID NO:3;
      (f) a polynucleotide consisting of nucleotides 1001 to 6002 of the nucleotide sequence of SEQ ID NO:3;
      (g) a polynucleotide consisting of nucleotides 2001 to 7000 of the nucleotide sequence of SEQ ID NO:3; and
      (h) a polynucleotide consisting of nucleotides 3000 to 7000 of the nucleotide sequence of SEQ ID NO:3; and
   (ii) at least one sequence selected from (i) to (l):
      (i) a polynucleotide consisting of the nucleotide sequence of SEQ ID NO: 1, or a fragment thereof;
      (j) a polynucleotide consisting of the nucleotide sequence of SEQ ID NO: 2, or a fragment thereof;
      (k) a polynucleotide consisting of the nucleotide sequence of SEQ ID NO: 4, or a fragment thereof; and
      (l) a polynucleotide consisting of the nucleotide sequence of SEQ ID NO: 5, or a fragment thereof;
   wherein said polynucleotide enhances foreign gene expression as compared to a foreign gene expression vector without the polynucleotide.

12. The foreign gene expression vector according to claim 11, wherein the foreign gene encodes a protein that is a multimeric protein.

13. The foreign gene expression vector according to claim 11, wherein the foreign gene encodes a protein that is a hetero-multimeric protein.

14. The foreign gene expression vector according to claim 13, wherein the protein encoded by the foreign gene is an antibody or a functional fragment thereof.

15. A transformed cell into which the foreign gene expression vector according to claim 11 has been introduced.

16. The transformed cell according to claim 15, wherein the cell is a cultured cell derived from a mammal.

17. The transformed cell according to claim 16, wherein the cultured cell derived from a mammal is a cell selected from COS-1 cells, 293 cells, or CHO cells.

18. The transformed cell according to claim 15, wherein the foreign gene encodes a protein that is a multimeric protein.

19. The transformed cell according to claim 18, wherein the protein encoded by the foreign gene is a hetero-multimeric protein.

20. The transformed cell according to claim 19, wherein the protein encoded by the foreign gene is an antibody or a functional fragment thereof.

21. A method for enhancing foreign gene expression in a transformed cell, comprising introducing the foreign gene expression vector according to claim 1 or claim 11 into the transformed cell.

22. A method for producing a protein encoded by a foreign gene comprising culturing the transformed cell according to claim 5 or claim 15 and obtaining the protein encoded by the foreign gene from the resulting culture product.

* * * * *

SEQUENCE LISTING

<160> NUMBER OF SEQ ID NOS: 96

<210> SEQ ID NO 1
<211> LENGTH: 8450
<212> TYPE: DNA
<213> ORGANISM: Homo sapiens

<400> SEQUENCE: 1

| | | | | | |
|---|---|---|---|---|---|
| attttgcttg | aaaggatagc | atcaaggaag | tgaaatgaca | acccacagaa | tgagagataa | 60 |
| tttttgcaaa | tcatgtatct | gataagggac | ctgtagtcag | aatatgcaaa | gaacccttac | 120 |
| aattcaataa | gacaacccaa | tttaaaaaca | ggcaaaggat | gtgaataggc | atttctccaa | 180 |
| agatacggaa | aaacggccaa | taagcacata | aaaagatgct | caaaatcatt | tgccatttgg | 240 |
| gaaatgcaat | caaaaccaca | atgaggtatc | acttcacgcc | cattagggtg | gctatagatc | 300 |
| agaaagtcag | ataacatgtg | ttggcaagca | catggaaaca | ctgaagtcct | tacacactgc | 360 |
| tggtaggaat | gtaaaatggt | gcagccactg | tggaaaacag | ttttccaatt | tctcaaaatg | 420 |
| ttaaacacag | ttatcataca | cccaagcaat | tctactctta | ggtatatacc | caagagaaat | 480 |
| gaaaacatat | gtcttcacca | gaacttgctg | ttcacagcag | cattatgcat | aatagaccaa | 540 |
| aagtggaaac | aactcaactg | cccatcaact | ggtgaatgga | taagtaaaat | gtgatgtaac | 600 |
| cagtcattgg | actgtcattc | attaataaaa | agaacaaggt | actgattcat | gttctaacat | 660 |
| gagtgaatct | tgaaaacact | atgctaaatt | aaagaagcca | gtcacaaaag | gccgtgtatt | 720 |
| gcatgatttt | atatatacat | gaacttttat | atatatataa | ttatatatat | tatatataat | 780 |
| tttatatata | taaatttcta | tatataaata | tataaaatca | tatatatgat | atatattttt | 840 |
| tcatatacat | catatatatt | tacaaaaatt | atatatcata | tatcatatga | tatatgagat | 900 |
| atatatcatg | atatatatga | tatatgatat | atatcatatg | agatatatga | tatcatgaga | 960 |
| tatatgatat | catatgatat | atatgatata | gatatcatat | gatatatata | taatatatat | 1020 |
| atgatagata | tattatatat | gatagatatg | atagatatca | tattatatat | gatagatatg | 1080 |
| atagatatca | tattatatat | gatagatata | gatatcatat | tatatatgat | agatatgata | 1140 |
| gatatcatat | tatatatgat | agatatgata | gatatcatat | tatatatgat | agatatgata | 1200 |
| gatatcatat | tatatatgat | agatatgata | gatatcatat | tatatatgat | agatatgata | 1260 |
| gatatcatat | tatatatgat | agatatgata | gatatcatat | tatatatgat | agatatgata | 1320 |
| gatatcatat | tatatatgat | agatatgata | gatatcatat | tatatatgat | agatatgata | 1380 |
| gatatcatat | tatatatgat | agatatgata | gatatcatat | tatatatgat | agatatgata | 1440 |
| gatatcatat | tatatatgat | atcatatata | taccacatac | atcatatata | catcatatat | 1500 |
| acatcatata | tatcatacat | atatatgaac | tttccagaat | aggtatatca | ataaagacag | 1560 |
| gaagtataca | agtggttgcc | acagcctgag | aggagcaggg | aatggtgagt | gactgctaat | 1620 |
| ggatatggca | ctttttttgg | ggggtgatga | aaatgttctg | gtcagacaat | ggcaattaca | 1680 |
| aaactgtata | cacacgaaaa | accaaagaat | cacacacttt | aaaagggagg | atttagctcg | 1740 |
| gcatggtggc | atgcgcctgt | actcccagtt | actcgggagg | ctgaagcagg | actgcttaga | 1800 |
| gcccaggact | tcaaggctgc | agcgagctat | gatcgctcca | ctgcactcca | acaaggatga | 1860 |
| cagtgcgaga | cccgttttct | aaataataat | aataataata | ataataaata | acccaaggta | 1920 |
| cccagttcac | atgcaaaacc | actggtaaac | ataaattatc | tccaagtaat | ctagaaagaa | 1980 |
| aatgagcaca | taagacgtct | tctaaaaaca | cacatatatt | tctttacatg | ttacatttaa | 2040 |
| cgtaaaaatc | agctatgcag | aagttacatg | aacatttat | gttggaaagg | taaatgacta | 2100 |

```
ttattaatac agaatggtta agtacattta tgtttttatg tacaaacgca taaaaggaaa    2160
agcatcctta aaataaacac catcaatggc tcctcggtgg tcacaaaaca aaatcctcac    2220
acctttgtct tccttcacaa ttgagcttta tccacctttt caggcttatc tcccattatt    2280
acctgacaca aacttgggtg ggccagagtt tccactgacc atcccccgac tattcatcca    2340
acactatgtt cactgcctcc cattcctgac catttgcctt ttgtcttcaa ctaattctgg    2400
ggacgttttg tccaaataaa tgatccatat tcttgaaggc tggaatcaag tcctattaca    2460
aatatatttt ctcaccctct ccagagcata gcaacccagc atctactggc ctctcacagc    2520
tctaaccatc cacaacccta agctggcttc tcatcaaacg ggtacttttc accacccaaa    2580
ttcaattaat tcactcttac aataatgaag aatagtcgcc tacagcctac cttttccagc    2640
cttgattcaa tcatttatca attttatctt caaagtccct cacttcaggg agatgatata    2700
tcagctttca cccagagtcc taaagaaaac agcactcttg ccaatgacat agtgccacct    2760
agtggcaaca taaggtaaat cacagtggca gtagaaggat ctccacacta cttttacagg    2820
aatgcactgc aggtaaaaaa taagaagcta cagtactgtt tggcaggaca atttgtttca    2880
tacgtgcata ctatcgccct gactaaatta actcgcaagt cttacaggta ttatttgttt    2940
tcagttccat gcacagatta gccatttagt acttactaaa tcaaactcaa tttctgaagt    3000
gtcttacacc aatatattca tgcacatatg gttaaaattt tccttgagga tctatcatgt    3060
gagagtgtgg cttattataa caagtaaaca gaacaaataa atacaaaatg aaagaaatc    3120 gtatgattta ctcgcatata agggagcttg ttgtggatta agtttcatga cccaggacac    3180
tgaaacagaa atggaataaa tgagaataaa attaaaagtt gtcatcaaaa atatagaagc    3240
catctaaaga cctaggtgtc aagcatagct ctatgagtac aatcccgtgc ctgagattac    3300
catatgccca gctgtatgct atacactaag agatttagga aggaagcggg gtcagggatt    3360
gaccccagac tccatctttt caagtgggga agaaagatct tccgattgaa aaataaaggc    3420
aaaaaaggct tcaccgtcac agaagtttca acaaccaaca ggatatttaa aacagttatc    3480
aaagcaaaac cattgtatgt tcacttacat ttttacatag tccctcaaac tcacaaaatg    3540
ctgtttactc agggacttct tccggtctta ctagggagcc tggaaagtga cgggaggatt    3600
gcaagggacc actagaaccc tcttcctcaa ttcccttcct ctgagaaggg aggctacagc    3660
ttgcctctct aaccactaaa aggcatgacc ctcctcaaag ttaatagccg gattccctga    3720
tagatatttt cactaaatga attctcataa aactctcact aagatttaga gaaggcttcc    3780
agggttgaat tcctgaacat taagaacagc atgttttta aaagtttaac ttggtgattg    3840
gaccaggact tcatctaggc tatgaatgct cagaatggta ggtcctttac caaacagctt    3900
gagtttgtgt ataaagtgat ctcatcctct taagagtcag agaaacagaa ccaagcgact    3960
tcactataat ttgatctgag gaagtttctt actcacaata ggtaaatgaa ggcacatact    4020
aaccagcaat ataaacaaca atatcaagtg tcattcacac atgcaaaaaa cagacaaaat    4080
cccaaactct gtgttctaac aaatcgcaaa aacctcacta acaataaatt gaaatgacca    4140
aatgtttgga ctgaaaagca atgccttggt agcctagcca tgcctaactc aaataacaga    4200
accatctcga tgttaaaatc ctcacagatc aagctgtgta tgtctcgggt caagacttcg    4260
ccaaaaagca gtgagcacac acttaagagg gaaaaaatct acctcagcct cctaaatgca    4320
atcatctcta cacgagttgc aggccccaag cttcaacgtg ttctgctgga caacgcagta    4380
gaaagctgac aagcaggtgg ccttcccaca ctgactgaac cacctccatg cccatgtcca    4440
```

-continued

```
ttcattttct tgcccacccc atgtgctata acagacctcc tggctcaggg cactctttcc      4500
ttcctgactg ccttcactta atgactttgt acttttaggt gcaaaaatta tctgcagaaa      4560
tccacactga aaccaagct tgagaaaggc agcaataacc aacattttta caagaagaac       4620
aaggtcaata tcaagcccat cagattcaaa tagcaagcat ggatgaaaat gaaagattga     4680
aaggcttgag tgccttctta atgtattaaa tatccattta atttacaatt aagctcactg     4740
tgctcactgg cctttaatc agcttttccag gtcctgctca gacttgccta ggacatggga    4800
atgaaagaac ctatacattt atggaccaat ctaccttaac taacttgtca agtgttcctg     4860
catcaagcag aagaaacatc agtgaaactg atacaggaat taaccccttg ttaatccata     4920
aaacttaaag gagcgggatc caatcttctg gcttccctgg gccacgctgg aagaagaatt     4980
gtcttgcgcc acacataaaa tacacgaaca ctaataatag ctgctaagct ttaaaaaaat     5040
tgcaaaaaag gaaaatctca taattttttg tttgttgtga ggtggagcct cactctgtca     5100
cccaggccgg agtgcagtgg caccatcttg gctcactgca acctctgcct cctgggttca     5160
agccattctc ctgcctcagc ctcccgagta gctgggatga taggcgtgtg ccaccatgcc    5220
cagctaattt tcgtattttt agtagagacg gggtttcacc atgttggcca ggctggtctc     5280
aaactcctga cctcaggtga tccacccacc tcggcctccc aaagtgctgg gattacaggt     5340
gtgagccacc gtgcccggcc aatgttttaa gaacgtttac gaatttgtat tgggccacat     5400
tcaaagcctt cacaggctgc atgcagcctg caggccgcgg ttggacaagc ttggattaga     5460
gaaatctaca gagacaaact agtgacttag tagccctctg atagctcatg atttgcaaga     5520
aacttaggat gactatgtgt aaagaccaca acatcaatt taactgaatg gttcccgcca     5580
cactggaatg aggaagctga gcaaactcag aggactctaa gaaagggctg atgtcatctg     5640
aactgttcgg aattataaac tcctctaaac atgtttcaaa gccagaactt gtaggagttg     5700
ttctgataca cggattaaaa gagggatgac aaagtgtctg tcccccacac tggtcaaagg     5760
gacaggtcat tgttatgctg gcaatgcagg ctgctgaaaa gaatgtatct gtcaaaagta    5820
atcaaagtaa tgaccccaga aggctccaga aacagactgg taaattcagg ttgcttttcag   5880 acttccacaa tgctggcaca caaggggaaa gacaaaacta acatttacag agcattatat    5940
ttgatattac atttaatccc cattaaaaag atactatttc ccgtttcact agtgaaaaag     6000
ttgatctttc aaaggttaaa ttatttaaca ccaaggtcaa agggtaagtt ggagagacca     6060
gattcaaacc cagtctgaca ttaaaacatg tgttttcccc ccacatcgtc tcctgctaat     6120
aacctcaaat ctaaaaactg acttgcccta caccttgagc cccatcctac aaactctccc     6180
tgacgttatt aattcagctg tcactgtgca cctacaacgt gccagacacc atactcctca     6240
acactctgta ggcacagaag gaacagataa aaatccctac cttcatagat attattctag     6300
gggtaacaca ggtaaataaa acattaaaat agttttcaca tagtagcaaa ttccatatag     6360
caaaataaaa cagaagaagg aatagcaaat gagggagatg ccctcttaaa catggtgctg     6420
agggaaggcc tccctgagaa agatatcatt taccccaaaa ataaaaaagc aagtaataga     6480
aaaaacaggt aaaaggtgtt ctagacactt aaacctgcca cattgagaac tcagggttct    6540
gatgcaaaac ctcgctgcat agaatgcatt aacttatttt tatacattta aacaaacaaa    6600
ctctacttaa gaactgtgtt ctaaaggaag gagcatatta caggaaggca attttggtc     6660 agagtagaca cacttaaaaa ctaaacctat tgaaagacca agaacaactg aaagtctttg     6720 cttttgtcaga ttttttgacca aaaggaaaat taaagaaaca caccgtgccc atccaatgat  6780
ttcaccaagg aattttaaga gagaaaatcc tacttcttcc tcacccagta gccagtgaaa     6840
```

-continued

```
tgactgagca aattcacaag ttcactgggg ctgctttcat gtaacacagg gacaacacat      6900
gacagacaca gtggaaccct acaggttgcc tagtatttga aagactgtga agaggaggag      6960
atgtcaaaat tcaaagtctt aaatgatgta gttttaagta tgttcagcaa tttcaccact      7020
cagtagtaaa gccagctaca gttgaaagca atcagaaatt tgagggtgt gaaataagca       7080
gaagcacaga agttaaggat ttgtattctt cccacatttt ccactttatt ttatactgct      7140
gagaaaaaac aaatttaata gttttctgct gtataagaga gacacattca ctttatgtca      7200
cagtaagagt cactcaattt taatacaact atctcaatgt ataaattaac attctccccc      7260
ctgcccacac atagtaagtc tcttatgatg ttgctgatta gagaagcaaa agttgccgct      7320
acaattctct tcctgcattt taatataaac aatcatcagt ctttcttca tagagtgcag       7380
tgtgggcact atcatcagaa tgtaccagca ctgggtgtgc aaagtttaca aagattagca      7440
agagcaaaag tgttgagatt tttgaaattc atgctgctgc aaagaagtat gtaaaaactc      7500
actcaccata gaggaccaca cagaaactca ggcatgaagt tatatggctg tgtgagtggt      7560
ttgggagaag gaacggaaag cacttccacc aacctatatg cctgagcaaa ttaatgcaaa      7620
acctcagaag ctacaaaaaa gtttatctac ctaaattaaa attggtgtcc acagcagtag      7680
ccagcaaaat gcctgcgaag cgcaaagtgg taaatatttt agggtctgta ggtcatatgg      7740
tctctgttaa acaatatgta aatgaatggg tgtggctgtg ttccaataaa acttcattta      7800
taaaagagg cagcatggta catccagtca gcaagctata atgtaccaac ccccggtcta       7860
acactaacca aatacctctt aataagccaa agaaactgtg tcctcttagg ccggaagcgg      7920
tggctcacac ctataatccc agcattttgg gaggccgagg cggggagatc acctgaggtc      7980
aggagtttga gaccatcctg gccaacatgg tgaaacccta tttctactaa aaatacaaaa      8040
attagccagg cgtgctggcg gcgcctgta atgccaacta ctggggaggc tgaagcacga       8100
gaatcgcttg aacccaggag gcagaggttg cagcgagcct agatcacgcc attgcactcc      8160
agcctgggca acaagagaga aactccgtct caaaaaaaa aaggaaata aaagtataca        8220
aagtgaaaac aaagaaatta aactgcccctt atttgccagt gacattactg tctatgcaca    8280
aaattccaaa aatctacaaa aaagcttcta gtactaaaaa tgagtttagc aaggttgtag      8340
aatccaaggt cagcatataa cataaaaatca ccttcctata tactagcaat caccaactgg    8400
aaattgagaa gtatcattca caacagtacc acaaacatga aataaatgtg                8450
```

<210> SEQ ID NO 2
<211> LENGTH: 8420
<212> TYPE: DNA
<213> ORGANISM: Homo sapiens

<400> SEQUENCE: 2

```
tcttagtatg gtaaaccttt tgaagtagat tcaaatgaga atgggaagag agaaaaggga       60
gagaagcaac ataagaaatc tcttttaagg aattttatat agagagaaac agaggaatca     120
gttgatagtt ggaaattatt ttaaagaaaa tgggttattt taaagaaaaa aggtattaca     180
acatgtttgc actattgtgg gaataatcaa gttgagacag aaaattattt tttaaggaag     240
agtctaattg ctgaagtgaa agagaatgaa tgagaccctg tgcataagtg tgatcagata     300
ggagcatgta cagctcaagt aagaacagga agaaagagac aataaacatg tacagatagg     360
atgggctggt cgatgtggtg gtgaaaagac atgcgagtta ttactgatta cttctatttc     420
cccagtgaaa taggaagcca ggttcataaa ccaaaatgaa gaggagcgag gcagtattgg     480
```

```
aagttcagga aaagtaatag gtgtaaaaat atgtaaagta gaattaccag ggagtatgaa      540
gatacatttc caattaagga tgaagaattt aaagtgaggc cagccaatac ccctgctttg      600
cttcagctac atcagctgca taggttcagg cacagaatac atggaacatt gtatttaaat      660
agggcctgga ttttacaaaa gtaacacaat gaagaagaga gatgcaaggc tatttgaggg      720
tgtttgtggg agagattgta aaatattagc taagtaagaa ggggactgca aattttagtg      780
gtataaagga atgaggaaaa gtgtaaatac agtggggtca agaatgtttt ggagccaagg      840
cactagaggc aattagctga aaatgtaggt gattattggt gagtgacatg gtttaaatga      900
aaagtataga agggtacaat tatccatcat gaaaagttct agggtacaac taagatctga      960
gtagctgaag tagaatgaaa gtagaatgga cctttccata tccagccagg ttcagtgaca     1020
gaaggttagg aaacaaatta taaaccactt gagagaacat atcccctaag ttgttttttgc    1080 tattttttctt tcagcatata tttgttggaa tgccaactat gttcagttca attaatatgg    1140
gcttcttaaa taagggctcc agcactggat aatcctgcca tttattttga tacattccat     1200
cctgctgctc agatctattg gcatctacag gatgtctttt gagaagatgg gcattcacat     1260
ccctatgtcc tagcaaattt ccaactcaga aaaccacatt aggcttctct atatatcttc     1320
caactatttc aatggaaaat acaattctct gatttcttcc tatgatattt atcaaagaga     1380
atggtgcctg ccagttctag ggtgggggaa ctcaatacaa atcaccaacc tttagatgac     1440
accctgtctt caaagtgctt tcaaagtctg cagaaaaaa agtacccagt ggctataaga      1500
ccacccagga gttcagtcat gcattctaag tagcagatca ctggaatgta attggctagt     1560
gagttcattt tactcttctc ttcttggtca catgttaccg cccttgtacc ctgcacgttc     1620
tctttcccag acttacaaag catgttctct tgaattcgtt ctctttttaa attcacacag     1680
tcttaatgat tcttctttca caagagtctt tcactcttac aattcagttc aagtcatcca     1740
catgcttatt atgagcaagg gtctgggact tagggaaaa gggaataaaa agatgaatga      1800
aatgtgatcc ctgcagtcca agagcttgct gtgaaaaagg aagtttggct tacattgcct     1860
ccctaatccc ttggctaggc cagaacagaa tattgtctaa aacctcctca cgtcagcagt     1920
cctctggggt ggtgactgga agtagaattt aaacaaaaat ataattgaca cataataatt     1980
gtgcatactt atagggtaca atctgatgtt tcgatatgtg tttaaatggg tgcattgtgt     2040
aatgatcaaa ttgaggtaat ttatccacca ccttgaagag agattttttca atattctcat    2100 tgcgaagaag caggaatttt tagcagacaa ctgagatgct tcttgttcac actaagtcat     2160
tctgacgatg gatttacata acttgttgtt ttttttgtgt gtgtgttttt gagacagagt     2220
cttactttgt cgactaggct gaagtgcagt ggcacaatct cggctcactg caacctccac     2280
ctcccgggtt caaacgattc tcctgcctca gcctcctgag tagctgggat tacaggtgca     2340
tgcaactagg cctggctaat ttttatattt ttaatacaga tgggatttca ccatgttggc     2400
cctgctggtg tcaaattcgt ggcctcaagt gatctaccag ctgcggcctc ccaaagtgca     2460
gggattacag gtgtgagaca ccaagcctgg tacatttaca tttcttatct ggatctttcc     2520
tttagtaagt gctaaggaat cctacttccc ccaatatttt ttcctatttc aatgttttag     2580
catgtatcat gttactactt tgcagacatt tgattttccc ctttgtttac tgtaaagtat     2640
atttttatag cctttgtaat agaagtattc taaaatctgc ctgcaaccta tctttctgac     2700
tctgcatttt agggaataat tctctgttgt ggaatgaaaa aaaaaacaga gcctgtggag     2760
tcagagatct catttcaaat tatagttatc cctaggaata aatctgagtg acaggtagta     2820
tagtataata ataagtataa agctatggtt aaggaaaact caacaacctt atctgtaaat     2880
```

-continued

```
tgggatgaca acagcctacg tcaaaaaaat gtgaaggtaa atgagataat gtaaggctga    2940
tacttagtaa gcaatttaaa aacacccaaa aaactattgc catgattact ctacttactc    3000
tatttctcta tgctccaggc aaatgaacta ctaatgaccc aggggtcctt ccccattctc    3060
ttcttcacaa ggaaatattc tctctctgtg tgctgtttat taaaatctac tgccccttt    3120 agaagccttt ccagatcatc ccatggccaa gaacgatcgc tgcttcctct tctttacata    3180
cagatgtttt tctcctgctt gacaattatt tttgtgcaat tattttcctt ttgattgtgt    3240
ttttaatgtc ccccccaccc cacaattttc cagactgttt gctccacgag agaggagacc    3300
atcatctctg tgctcaccgt tgtatgacca gtatcctgag gagtggctgt tacataatta    3360
catcaggcac tcaataaaaa tttgatgaat aaacactgga ttttaaggca ggtatcatat    3420
cttacatagc atatcatatc ttacatttta tgtccctcac ataaatacca cagagtgaag    3480
tatatgacag ataaggtcat ttctcttgat aagtacatag tccagtctga aacagatatg    3540
ccaaaaaaaa acaaaactgg agtaaacaag atgaattgtt ttaatagagg cactgtatta    3600
gtttcctagg actgccagaa caaatcacct caaacttagt ggctgaaaac aacaaaaatt    3660
tattgtctca cagttataga tgttagaagt ataaaattaa ggtgtcagtg ggattggttc    3720
cttctggggg ctgtggaaga gaatctgtcc caagccttca cactgtaaag tacagtactg    3780
gagggatagg acttcaactt gctctatctc agatagagag gagccatttg ttgtgaattg    3840
agaagagggg tatgttgaat ccataataag cacataaaaa cttggctggt tcataggaga    3900
agtaacatgt ttccagctct agtaaaaaac aaattgaagt ggcctataaa aaggtacaga    3960
gtacgacaga atgaaaaata aatgaacaag aatacagaga ggatgtggta aattatcatg    4020
tttccctaat atgttattgg acactaaatg gtattagaat tatttatcaa taataattct    4080
aaactgttgc aattgaaaga atatattaag tggtgttata tgagaagtgc cagggcattc    4140
tcatttctgt ccaatgggag aaacattttc gtttgagacc tccgtgaata atacagtctt    4200
ttagttagga gagctgcatt ttgagtggtg caggcagaat ggcgatctct cacccacaca    4260
aacactaaga tagagagaga cagagacaga gacagagaca gcagagagag acagagaaag    4320
gaagtacagg tactcagata gagataagcc atttcttgac attaagaaat aaagtagaat    4380
ccattggagg gaaataaaac tgcctcagga acagagttaa ttcacataca catgcaggta    4440
aacacacact gcttgatact tactgtggac tttgaaaatt atgaatgtgt gtgtgtgtgt    4500
gtgtgtacat tcagccctcc atatccatgg attttgcatt cacagattca accaaccatg    4560
aattaaaaac atttggaaat aacaaacatt aaaatataac aatacaacaa taaaaataat    4620
acaaataaaa aatatagtgt aacaactgtt tacatagcat gtatgttgta ttaagtagta    4680
taaatctaga gattacttaa tgtataccag aggatgcata ggctatatgc aaatactatg    4740
ccactttaaa ctgataagaa cagatactaa acttcatctt agccaaaagt cagagaaaca    4800
atataactat gccattttac ataagggact tgagctgagc atcctcagat ttcagtatct    4860
ttggagttcc tggaaacaat tccttgtttt atatatatat atgtgtgtgt atatatatat    4920
atatatatac acacatatat atatatatat atatatgata gctactgagt gacaggtgat    4980
attataccat accacttgtc actcagtagc tgtatatgca tatgtatata tatacatata    5040
catatatgtg tgtatgtgta tgtgtgtgtg tgtgtgtgtg tgtgtgtatg ctgtctttcc    5100
tcggtatcac agggaattgg agatatatat attcttttca gtacaaaaaa aattgaacac    5160
agatgggtat ggtaccagaa cagaaggtaa agacacatga aaaaaatttg caacaacatg    5220
```

```
aatggaactg gagatcatta tttgaggaga aataatccag gcacagaaaa acaagcattt    5280
tattatttta ggtgaaagac aaacatttta ttttaggtga aataatccag gcacagaaag    5340
acaaacattg catgttctca tttatttgtg ggatgtaaaa atcaaaacaa tagaacgtat    5400
ggaggtagac agcagaagga tagttaccaa aggctgcaaa gggtagtgta ggctttgagg    5460
gtgaggtggg gatggttatt gggtacaaaa aatagttaga aagaataaat aatatctagt    5520
atttaatagc acaacaggtt gactatagtc aaaataacat aattgtacaa tttaaatatg    5580
aaattaaata tatatacaag actagaacac caagttgaat gactccagct tgcgaaaccc    5640
acattgatca ccatgcttgc cccaagggaa gctgtacaat gtctggctcg tccagaaccc    5700
catcatttat cactagcaat ctattgtcca taatcatgtt taaattaata gcattttaaa    5760
ggtacaaata ttttttaaaa aacaaataat tatttaattc gccttttaaa agcttttttaa    5820 aaacgttttt aaaaactttt ttaaagtcct gaggactatt ttcttaaag tgctcagtta     5880 cagagctcca tatattgggc tatgatagcc ttacctgatt cttgccaaga atctagtgcc    5940
cagaaaatgc aaatacaaag taagcaactg aaaaataaac aaataagttg gaggtatgct    6000
acctgttgaa atatgaccta gcgcaaacac ctatgccact tgcttatgaa atcatatagg    6060
ttttcggtgt gcagttttga ctgaatgagg gagtttacgc tggaccacaa gggggcccct    6120
ctgtcaataa cgtactccat ttgtgtatta agtcaaaaat gaaatggaag agaaaagaaa    6180
catcgatgac cccaagtctc tttaattgaa tggaggtaaa agggaaacaa cgaatgagaa    6240
aagtactctg ccctttttaag aatcttgcat tcacattcct gatgaagtta ttttttcctcc    6300 tctcactgat tccatttca ctctattaca tagcaccgtg ttccccagga gctcctgaat     6360
gaaggacatc actcagctgt gttaagtatc tggaacaata aatatactag tttcaatgtc    6420
taggctatgg gtattccttt ttactgaagg tatgacatat agctgcccag gcctgactaa    6480
attaatagta ataataatta ataatggcaa attttattc tattaagtta cttggcttga     6540
cttgtagaaa tagcaacatt catctgaaat gcccctcct acactatgt ctaaggacaa      6600 atcccacata caccacagat aacttcattt tacatgtttt attctgttac caaactaaat    6660
ttttatcata tagtctgttg ctcactgaac tcttcagtaa ttctcaacat accatgtaaa    6720
gcattaagca cagttccaac acagagcaaa tgagcaataa ctgttagtta ttataacatt    6780
attatgtgtt ttcagtgcat taaaccactg gtctgatacc tagcccaaca ttctattaaa    6840
ccacataatc cagttgaata atatatgata atataataaa atggcgataa gtgctaaata    6900
tccagataga aacacagatg gaatcagaca gcttttccca gaaatagaga aaatagtaga    6960
taggcgatct aggcctaagc actctaagca gaagctaagt tatcacagga tatcttggca    7020
atctgtggca cgtgaaccct tttcttctgg agtctggaac tatgttgcaa ctctcacttt    7080
ctccctatct agagactcag tttgttccct tgtgattatc agcagttgag aaatccttag    7140
accttctgaa aggactactt tttaaattta tatataaat atttaaaata catatcttta    7200
tatataatat atatttaaat atataatatt taaattaata tatatttaaa tatataatat    7260
ttaaattaat atatatttaa ataaataaat ttatatttaa atatataata attaaaatat    7320 attttaatg aacagagagt aaaggattat tttgaagaga aactcctggt tcccacttaa     7380
aatcctttct tgtttccaag ttttttcaaat ggagccctct ttaccagctt gcccccttcag  7440 agataagctg ttcccctact tattcagatc tgagatctga aaacattcct tttcctgtga    7500
gttcagctag gacaaagatg gagctttttg ataaatttg gcaaacacat ttttaaaga     7560 tgaaaatttt taaaaattga aaaaaaaaca tttatagaaa gagacttcta atccaaattt    7620
```

-continued

```
aacttctcaa actatgtttt gaccggctag cataatgttt cagtcttcct ggagaatgcc    7680
ccttgaaact gttttcttct acacaacttc ctcctttcct ttgactttcc tgctctggaa    7740
gggaagaaca ggaagaggac agatcaaatt actcaagagg aaggacaaga aataaggaac    7800
caaattatca acaattggag aaagaaagct gatgtcagta tcatttcata tatgattatg    7860
tcagagtcag gtggataagc caatcctgtt gaatagcata cttttcctgc tactcctgaa    7920
gggtaaagag gtctttctct tacaaagccg tcctagctag taatcttaca ggtgcaaaaa    7980
gcttgttttc atgttatttc ttagtaactc aaaatacctc taaagttata catattatga    8040
aagtactaca gtcacagtgc tgagaaaagg agtaaataag acaatgtata taaaaacact    8100
tggctcagcc cctggctctg tggttgataa atattaagtt agtattcatt attattataa    8160
tttccaaaga gtccattaaa agatatagaa gaagggaggc agcaataaca ctaagagaaa    8220
attccattat ctccaactat ttatcctcta gcccaaaata attgccatta gaaagagcaa    8280 cttaacaaa aatttaagt tgcaatagat gttcaacttt aaatccatcc cagaaaaatt     8340
tctaaccaaa ggagcataga agatttgatc ttatttcta agtagtatag acttaattgt     8400
gagaacaaaa taaaaacttg                                                8420
```

<210> SEQ ID NO 3
<211> LENGTH: 8475
<212> TYPE: DNA
<213> ORGANISM: Homo sapiens

<400> SEQUENCE: 3

```
gcataacttg taagaaatgg agtgaggtct cagttcaaac tggcttctgt atgacttcaa      60
agccaaagtc agcaacttag aaggcaaaaa ttataattta gttggcaaat acgagaaaag     120
gtcagaaaca catgaaatga agctcaatag gaacacttac agggtagcag ggtagtagcc     180
tagggaaaaa agtcagacac taaaattgtt taaataggta agttcaaggg acaggtaaag     240
accttagtgg gtaagaagcc aatcagcaga cgaactgcaa gcaagcactg tctctctttc     300
ccttctgtct cctcttgtag taactgacca caattaaggc tgcctagggg aataatgaag     360
taatcctcct attatcagca atggtctgat ccagtgccag gcaccacaga caacttggtg     420
ttcagagaag atccttcaag atgaacaaag ggtcaaaata aaaaattcta gaagagagaa     480
gactgatcac aatttaatgt aaggcttgga aggaactgat ctctaccttc cttaacatct     540
caagaacttc ctcagattca ttggatgttg agtgtgtgtg agtctagtag aaaaatgaat     600 ttttgttct taacttggat atgtgattag gatgttaata attaagtctg gctaatatt      660 gaaggtatct tatgatgggc ttcttaaagc attgatcaca aagactgcat gttcataaac     720
tgagctgcac ttgttaggat tctagatgtt tgaaatttct tgtgttattt tggtctcaga     780
tttctagaca aattttctca aattcctatt tcacttttg acatatcatg agtgactcaa      840
atgtttgccc ttgagtcgga aaacacccag cattaggaat aggcacataa acataatact     900
tcaagcttca gatttaagct caattataaa gtgtttaaag gctgtgctga tagttcttct     960
gagtagaatt cctacaacta tgggtttgtc tataataaaa tgttcactct atattgaacg    1020
ccttatttaa aactcgaaat gtgtaagtag taataaagaa aatatgtcct cctgtaacca    1080
aagctaggac cgattacatg ttcacttgac tgacagatac aatcacctat attaggagca    1140
atcagcactt ccttacaaac taacaacttg agatgtagtg ttcccattgg ctatgaagat    1200
tttctttatt tactcagaat agtctgtagg atctgccagc tgcccctgat tataccagct    1260
```

```
gcacccaatg atcacagtga acattatttt acattctaaa taactggtgc aaggtgagcc    1320 atgttttct gagtttccta tcacctttgt gtttcaggtc ctcaaatgtt aatttgtaaa    1380
gctgctgttt caggcaaaac taacaaaatt agcatctaat caataaccat actatgtcca    1440
cccatatcct ataacacaga agtagggaa gagtgagaaa ggtggaagtg gagaaataga    1500
ggcccaaaaa gaaagtttta tcacaggaat atctagatgt cttctgggat tgtctgttaa    1560
agagctgtga cactcatata aatgcagaat tactctcttt cttccttgtt ggttagaagg    1620
ccaagggtgc catggtaata ctaccaaaca tatatcaaag cttggcagga aaaatggtac    1680
cttcagaaat tttataatct gatatcaaat aggtcaagaa atataataaa actagttct    1740 ttggtttcct tagaaacctg gaaaacttta aattagaaac ttagaaagct ttaaatcaga    1800
ctttgtagtt aaaaaaggaa attttagttc cttccagcat tagaattccg tgattctctg    1860
actctgagcc tggattaaat ctagcccagc tgagtggaaa cttaagtaac tagctggttg    1920
cctttagtga tcttccactt tatggctgct tccgcctaag aagttcatca tcgtgactta    1980
ctttctttgg ggcaaagtcg tgactaactt tctttggggc aaagttggaa agcagaggtc    2040
aaagtcaatc agaaatggga caaactcact tcctactgcc tggtgaaggg gccattttca    2100
gtagcccctt ttcaagatta gtttcattca agatttgata agctgttttg actttactat    2160
agatcttatt atccatgtca gttaagttta tgcttccact aaatctatct gaattcaaaa    2220
ggtaaaaagc taatgctcag tcttatcaga tttatcttat ttattaatag aatgtggatt    2280
tttttaagca tataacaata atagtaatga taggaccata aatgtggatg gctctttaca    2340
agtcactaac attacataaa ttcctcaaca acacactctg aggccataac aaactttag    2400 aaataacaca attggctacg gaactccagc catctagctt catgggctcc cactttaatt    2460
tcaaaacaac agaactgtgc acattcattt acatgattag ggcagagctt aactgtatct    2520
catgtagcac ctacatcatt cttcagacaa acttattgcc ttttacagac aagaaaactg    2580
gggctcaaaa aaggacttgc ttataactgg ctaataaaga ggaactctgg gttcaaagtg    2640
agtccaattc tttcttccac ccacagcttc tgctaaagtc attacagaaa tgcatagagc    2700
agttcttcca cgttattgct taggttctca aagagcagtg acctaataca acatgctcta    2760
taatttatta ctgatttaac tatttcacta aggattcact tttaacttt aacttgtaaa    2820 tatgtctaat aaacaccact gaaatagcaa cctctttctt catggccttg tggttgtaaa    2880
gcaagctagt aatatatgtc tgtggatttg tgctaataaa gttctataca cctcattaat    2940
tccacaaatc ctactgggta tttcttatct gccagatcct acgctaggta ctggatacac    3000
agtactgaac aaaatgggta caaatgagcc tcacagagct tgtttcattg aaaagcagag    3060
agatacacac taatcaacaa attaatagta acacactacg atgtgttttg aaggaaaatt    3120
agagcatcaa agagacggtg ttagcaggtg gaggggagct cttttagatg gagaatgaga    3180
atgcctccct aaagacatgg gaataaattg agatcacaaa aaatgagaaa tagccagcct    3240
tgagaagagc agaaggaaga acattcaaag gaaaagaaag tgcatactgg aaagcctgaa    3300
cactagagtt tggtgtatgt aaggagctga gcaatggtca cttgtgtgat aagatgtgtg    3360
gatgtggggt gggggcagg ggtgagtccc acgcagctct taagtgtgtc ctcagactcc    3420
tgtggtttcc atcagccaca acctgaataa ctgtgtggta atccaaaaat gattacagat    3480
taaacatata aaaatatcat tacacccata gtacctaagc caaggacaca gtattctatc    3540
ttttcaatga agatctgcat gaagtaaaat tattatatat aatttaggt attgatatag    3600 atacatcagt ggatagatat agatatgtgt ctctggtata gaaaaaagtt ttaaagggat    3660
```

```
attaaaagtt cttatcttgc agggttgaag attgtggcaa ctttcatttc tttttaattt    3720
taagaaaaaa gtggtattat gggggattag catgtttgtg ggtatatgta tattttttaat   3780
taaaaaataa acaacaaaat gaaaacgttt ttcttctatg aaagcctaat aagaagaaat    3840
ttcagctgtt ttaacttagg gagctaaaaa catcaaatcc aagaatgttc tctggaactg    3900
agctcaatac attttttattt gagtaagaat tggatacatt tccatccccct tggggctcca   3960
gtctgtcaat attttacttt tcagcgataa aaagacacat gtagataatc acagtgacct    4020
cagtaacttt ccttctctta tttaagtttta ttttattttct atcgtagttt tccctgttaa   4080
agattttttc tttttgctta catatataat tttagagaat aacaatgcac acacaaaaaa    4140
ttcctcttgt tctgctagac ctggactttt tctctaatat atatctccat tttttgtctt    4200
ttttcagacg tattttggaa gcaaaggaga gaattgctat atagctgact tcctcttctc    4260
atcaacagtg ttttaacagt ttttaagcaa aagtcagctt tgtttatcta agattttttt    4320
tgctggcatt taacctaccc ctgcctcccc tttcccaagt ccacttcagc caacctctca    4380
ttcgacaggt accaccctct aacataactg aaataatgtc taccattact ggatcttgct    4440
agcaaagaat ctcaaatttt cccacttggt tgtaaattat tttgtaatct ctagtgttta    4500
aggtgcgctt gtcctatcta atcccctccc tggcaggaca ccttacagaa cctacccctt    4560
acactagtca ttaagcacca tcagggacgg atggctgtgt cactggtctg tttggtattc    4620
cctactgatc ctaccatgtg gtgattatct atgacttccc taatccctgg ctgccttagc    4680
tgggactggc tgacatgctt ctcaggttgc cgctggcttt acagtccttt actgcccatg    4740
ccactttgga gataggcagg gctagtactt ttctatataa gcccccaaac ttgactttgt    4800
gtttcacagt aggtgaaaaa gttgggtctc ttttctttta cttttctttc cacaagatga    4860
taaagctagg ggaagcctgt ggacatggtt tatttctgca actgcaatga ttgattggtg    4920
cttcctgctg cttacttcct aaactttgtg ctcagtgtca gatccctagc agtttctatc    4980
ccctgctctg ctaaaaaaga atggatgttg actctcaggc cctagttctt tttaattaaa    5040
ttgtatttttt gttatcatta ttattattat tattttgaga tggggtctta ctctgtcgcc    5100
caggctgaag tgcagtggtg caatcacagc tcactgtttt agcctcctga gtagctggga    5160
ctacaagcgt catgccacca tgcttctttt taatttttta aaatggtttt ctgccttcaa    5220
ttctaagcac ttctcaattg taaccaagag ataaatacttt ttatgaattc ttaaagttat    5280
caacagatac tcaaagtttt agcaaagtct aaatgatatt aagcttgtcc ttattgccca    5340
agtgacttca atgactattt gttaattgca accaagggtc atttttttaaa tgaatatata   5400
ttattattat atatataata ttaaggtcct caaatacctaa aagtttagc aaaatctaaa    5460
taatattgtg catattcttt tattactgta ttagtccgtt ttcatgttgc tgataaagac    5520
atacccaaga ctgggcaatt tacaaaagaa agaggttcac tggactcaca gttccacgtg    5580
gctggggagg cctcacaatc acggcagctt acgggattgt tgagaaatga cacttctcaa    5640
gctggggcta aactatctct gtggtagttg ttctgattca agtattgaat tggttttttt    5700
tgttttttttt gagatggagt ttcgttcttg ttgcccaggc tggagtgcaa tggcacgatc    5760
tcagctcacc gcaacctctg cctcccgggt tcaagtgatt ctcctgcttc agcctcccaa    5820
gtagctggga ctacaggcat gagccaccac acccagctaa ttttgtattt ttagtagaga    5880
catggtttct ccatgttggt caggctggtc tcaaactccc aacctcaggt gatccacctg    5940
ccttggcctc ctaaagtgct gggattacag gcataagcca ccgtgcccgg ctggagcatt    6000
```

```
ggtatataaa agctgcctag gtaactctaa cctttggccc catacatctg aaggatacct    6060
acaatgcacc tgaaaaatgc aactgaaaca gtagttccct gggaccacac actcagaaag    6120
ggggtgtatc aggagatcta gggaccagga gggtggaaga cctaaggcag cactacagat    6180
gatggagaaa aacccactgg ggaggggcga tcctaacctt gagaatcact gagatcatgc    6240
agaagtattt gatcctacag cattaatatt gtattgtatt gtattagtat atatatatag    6300
tgtatatata tagtattagt atatatattg tattgtatta gcatatatat actaattgta    6360
ttgtattgta tttatatata tagtattgta ttagtatata tatacagtat atatgtatat    6420
atactaatac aatgtactaa tacaatacaa taccatatat atatacacta acacaataca    6480
attagtatat atatatatat atatactaat acaatacaat actatatata tactaataca    6540
atatatacat atatactcac caagacatat tagtggtctg atgtctggct gccacactca    6600
tcttctacct tcagctctgc tctaccaaat atcatttgtt tctgggatct ttgcagtcca    6660
aggaacttca tccttgatat cccacccctt actaactttt ttttttttt tttttttga    6720 gacggagtct cgctgtgtca cccaggctgg agtgcagtgg tgtgatctcg gctcactgca    6780
agctccacct cctgggatca caccattctc ctgcctcagc ctcccaagta gctgggacta    6840
caggtgcccg ccaccacacc aggctaatgt tttaccgtgt tagcaaggat ggtctcgatc    6900
tcctgacctc atgatccatc cgccttggcc tcctaaagtg ctgggattac aggcataagc    6960
caccgcaccc ggccacccct tactaatttt tagtaacgtc caaggattaa aggaaatttg    7020
ccttacctat ttaacaggaa tcaacagggt taatctcact cccttctaa aaataattta    7080 taaacattgc agcaatctc atctatccct gtctaaactg tgtggaatta ctgccattta    7140
atgtaatcag tctactcatt tagtttgcct aaggaatttt tgaaaaaaca gttaaatgaa    7200
tgacttaatg gaataaccag gaagttgaag tctccaatag taagaatgaa ctcttgctct    7260
ctggataatc aaatgggtcc ttcctccttc aggtagatca tgccatttcc tcacttacac    7320
tgaacaggta aacaacataa ttactgactt caacttctag ttaattcctt cttttatcac    7380
tgagtatcct ttggctggga gttttgttgg ctatgctgcc atttttttcta gttatcacag    7440 tcctataaca taccaatcct tcaatataac tcatctttaa attgtggttt taccttctca    7500
agaagttatt aattatgcca gtgctaaatc ttctaaaatg attgttgact tgttgattag    7560
cccccatgca attcccctct cccgtccctc agcacgtaag gaatggccct ttgcttactt    7620
ccacagatcc ttaaatctac cagttagaag ctaatagcct acctctctac caggaaggaa    7680
ctgtgggctg aacataata catgttgact tataatttct tagaaaattg tgtgagaaac    7740
atcaaactcc tgattccagg atatgccaaa gacacatcat taaaaagcaa aacaaaacaa    7800
aacaaacctc atttgacgtt gctagtagtg gcatatttca tcaagatcag ctcaaataaa    7860
tagaagtgag attttcacac aaattagact gtagtgcttt ttttttttaac ttatctttac    7920 catatgattt taacggtaa aaaaaatcgt ttgagatatt agatgtataa tatttatcat    7980
ccaattactt cattagttca atcttttttc aatggcgctc ctgcatctga aataaggtc    8040 agaaaatttc atgttctgat ttcatgctga ttttcagaag aaaaatgtta gttttgtata    8100
gaataaccca tcctaagaaa tacatttctt attatatttc ttatcttata tttcttagga    8160
caatgagcta ttcaaagggt gatgataacc agcaccatca gtcagcatta tctaagaata    8220
agaatctgtg tttctacata cagacctcct aaaaaggaac ctacacttaa caggattccc    8280
caggcaattt ggatgcacat taagcttga gcaaacactgc attagaaagt tagttttcca    8340
tcacaaaaac agtaacaaaa ggaatataaa gtaagttact ttaataatat aagaagaggg    8400
```

-continued

```
gcaggccggg cgcagtggct cacgcctgta atcccagcac tttgggaggc tgaggcgggt    8460
ggatcacctg aggtc                                                     8475

<210> SEQ ID NO 4
<211> LENGTH: 8401
<212> TYPE: DNA
<213> ORGANISM: Homo sapiens

<400> SEQUENCE: 4
tttcatctaa gactacattt ctattgtttt atataatcag cccccctaag atcaacatgt      60 ccacatttt tggcaaagac aaagcctact gatttcagga tcattatttt cctttttcaa      120
aagcacaaac ccaaactgag aaataaatca agagaaattc ccttttttc tatgctaatt      180 tagaagtaga gtctttattt cttttcaaac ccaaagagaa tcagacatac aatatgaatt     240
tatctacttt cgcttgctca gactgagagg aaagattaat attttcaggc tgttagtcaa    300
aactgttcat tcaaatatta tttaataaaa tccaagaacc agctaaaaag tcgcttaagc    360
taagaaacct tcaccagcct catgggaaat tgtgtacagt tttccactag aatagcctat    420
aaatgcttac tgaaaatgtc taagttcata tcttggtaac taacatttta attcaatctg    480
cagaataata tatgcttctt tagtgctaag atatgaatat tagaggcatt ctttcttaaa    540
atttctattt agttatactt tcacaaataa ctatataata ttaaaattct gcatgtggca    600
taaaacatat tttaatggag aaggtaatgt gtagggagtt tatttctgtt tgctattaga    660
acttgtgttt attcttggtt aaaaaaactg cagattacaa catagaaaaa aacaaaagta    720
tgttgtatat ctcttacagt agaagataaa gagtagttct aaatttagaa aggaaaata    780 aatatacaca gtgaaaatat gtgtcagtga gatgttaatc aaagatcaac tattgctgag    840
accagcaata ttaaatccct gcacaattac tcatattata atgagaattt taaaaagaaa    900
atatgaacac ataacataat gaaggcagaa gtcactctca tccttcatct ttgtattccc    960
aattcaggaa gctggtatag tatcttcatt ataattacta ttcaacaaac atttgtaaaa   1020
tgaatgaata aggaatgaat gatgagaaaa atgataaaca tctccctctg tctcctggga   1080
gttaactgca ctactttctt ttaaatttaa ttaatcctca atgtccttgt aaaatagcca   1140
aagggaaaat gtatttacat tactctaaat attgatgcaa tctacaaaaa gtgttaaaca   1200
acttcctcaa agtaaataaa atgttcacaa tccagctagg ataaaaggat ttaaatcatt   1260
tcctaggtag agggctttca attagagccc ctgctgcatt aaccatggga actcatctca   1320
ctctcttcat gatggagccc tgagtgttgc tgctaatctg tactctacca ttctaatgct   1380
tttaaggttc cttttcagcc cttcctcctc gtaatccaca aatactgaga ccaaggcatt   1440
ttttgggtca gtcctaattt caagcattct atcctgccct ccccaaatga actcacactt   1500
attagaccat atgttcctat attagttcag gaaggggggaa aaaatgttaa tcacacttgt   1560
atataagaga tcatagaaaa acagtttact aacctgtgaa ataccattc attctctgtt    1620 tacctctggt ccacagctaa gcaatcagca ggatataaat gtaccctatg ttcactattc   1680
agtattcata agtatactac ttatgaattg gaaatctgac acaacattta catgacctaa   1740
ttttgaaaat ttaaaatagt gtaaggcccc taggcttaat tttacagggg aaagattaaa   1800
gggacacaag caaacatata ttctctctct gtgctgtggg acactggtaa ttttttgact   1860
taaaatattt gatacttaaa atgccaaact tctacatttc tgcagtaaca aggcagttat   1920
catattgaat accattcctt tctctccagt aagtagagtt aatattagca catgaactga   1980
```

```
aaatattaag tgattataaa aacgtccaaa taaattcatt aaaatttagc ttggcaaaat    2040
gttagtttca tgttcttggt agaagtcctt ttatatttat attcaaatga aatgaacaat    2100
ttacaagcaa aggaaatggc atcaaatatt tcacaccctg cctcccaagg tgtattgatt    2160 catgctttt gctcagatct aggtttctcc actcaggaaa agaggagaat gtacccatac    2220
ttgggaaaac aagtttccga tggcacagct ttgatcaaac agcaaaattc tatccatcta    2280
tgtattgcca tctgacagta tgacaaatgg tcccatgtgc gatattcaca ctgcattgca    2340
gtcaaacctg taagtcaaag gatatgaaat aatagtaact atacattaag cacagaagaa    2400
aatgaaacaa acaaaaaggt tttaaaccaa ccaaaaatat gtcttatttt ggatgttcta    2460
tatgttctta cattctctca ggtcttttgt gtcattatga acacaattct aacaagcttg    2520
attattttat ttccattcac atattacagg caacaagctg aaaaagtaga acggggtgta    2580
gagagacagg acaaagtaca gattagggct tgaagtgccc ctgaccagtc gacagcaacc    2640
acatggaata atgactcatg tgcattaatg atcacactaa atgatatttg ttttttacc    2700 tagtccttca actgacagct taaagaactt caggttgttc tgattcttga gcctcctcta    2760
cagcttcaga gaggactttc attttatttt ggatcaaatg ctccacaact agttgaaact    2820
ggaattaaat tttatatgaa gttcctagat gatttaaagc tgtaagaaga agaataatga    2880
atcataagaa aacttgctgc tacagatatc aaaaaggaat gttaccatcc ctcatgctaa    2940 tcctttcat tttaaataaa caggatctaa aaaaatataa gctgggaagt cctaaccaca    3000
tcaagaatgc ctcagatcag tgacccaggg aaccttccag aatggatgaa atagacccaa    3060
agctgaattc acctaatttt agggccaaaa acccaaaaaa caaacaaga ccaaaaaaat    3120 cttcagatac tgggagaaca aatctcaatt gctcaattgt atcttatgaa aacaattttt    3180
caaaataaaa caagagatat ttaagattca ttaagttctt gtcatttcaa attttaagaa    3240
aaatattttc taatggaatt acatatattt atatgattct tctagttata tccatggtaa    3300
taaatactct tttcagttgg aaataaaacc catttgtgct atattattag ggaaaatatc    3360
tacataaatt agttttaat ttaactaaag tctatctttt gaattcataa gcataaaatt    3420
ttaaccactt gcaaaattta taacacactt aaggtagtca gatgccttgt caagtagttt    3480
aacaaaagtg attttcacct gtttgtttta ataacagtgc atcgatttta tgaaaatcag    3540
gcatgccctc gggtcctaac aaagtatacg aagctgaatg gatctatgcc aaatatgcca    3600
gattttactt tctgagtctg attttatact tctgtcctct ttcttaccac atggcttcca    3660
gtatcactta cagactaacc cttcaaaagg agaaggctaa gttactaaca tttggaaggc    3720
ttatgaaagt gaagcatagt tatgagccag caatgttttt atttagggaa tgtgtgcaaa    3780
ccatacactt aagcaagctc tggggaatga gagttggggg gaatcaactc ttttatttgc    3840
taattggtat ttccttttaaa agatagagtt cttccagatt ttaactgtgt aatagttac    3900 tctagaaaaa ttggagattt gtgtgcatat attttatgtt gtaaacagac acatacccag    3960
agacactgag agagacagac agacagtaaa cagaggagca ctaaccacaa acggtttaca    4020
aatgacctct gtgctcattc acctgtctgt tccccacctt gccttttata gcaactatag    4080
caacagccat gagagtcatt gtggaaagaa ataaataaa attaaaaaat cctggaagct    4140
tgtaaagaat gtgagcaaag gggaggaagt tgtgaaaaaa atgaataaag ggcaccgatc    4200
cagagtattg aagaaggcag agtggagagc ctagtaatga gtatctggta ccccagtatc    4260
ctctcccaca gaatctgtac agctctccgt ttatgacagt ttaaacttaa tttaaattat    4320
caaacagaca cttttcctcaa acatataaat gatgaggcag ttcattcagg ctgtatgtat    4380
```

```
aaagttgttc cagccacctt tttctaatgg cttctctata tcttttacat ggagacaatg    4440
agagatttgc ttaggacaat ttgactgtaa tttagaagta ggaaatggga agtatttgta    4500
tcttctttgc ctaactcaca ttagttactc aagtaagcat ttcttccgtt attgcatttt    4560
cctgattaca agttttatgt tttctctaaa acacatatca aaagaaatgt cctaagcact    4620
atgcaggggg aagccatgac atttatccac cactgtcagc aaaaacatga acttagccct    4680
caacagaata tttcacttca ttctagtgtc acctctgcgt cacctgcact ggagtcacca    4740
cttgcctgtt gggtaagacc aggatgcacc gctgaaataa aaggggtca gacaatacaa    4800 gaaaagccag tagaaattgc caaatgtatc agaatacaca caggcttttct aaggatatgg    4860 cccaagagga aggctctaga gcccaccctg aaacaggatt tttgacttca cagataaatt    4920
atttaatttt caataacaca attcaattaa agaaagggaa atacaaggct aaacaaataa    4980
gaaatgaaga caaaaaccca acctttcaaa tctaaagaaa ataatctgtt ttaaagacac    5040
agatgaagat caggaaccca aaacagaaga aggaaaggc aattaacgct ggcatctgat    5100
aacaacgaaa agtatggagt ctggagaatc gctagactct aaaaattata aaggtttaga    5160
cttggacttt gtacactgaa gaaagaaaaa ctgcatgcat ttatactgac caatgtacac    5220
tattgctgct ttttaacttt tgtgtatatg tagggtagat ttttttttaa gtgaaagcaa    5280
gcttattaag aaagtaaaag aataaaaagg tggcttctcc ataggcagaa aactagcgta    5340 gttttttat tagaaattgt tattcaataa tagtacatgt tacaaataaa taccattta    5400 aactgaaaaa attgtagact ttcaaatcag ttagggtggt caccctaaaa aagggcattt    5460
tttcccctta gtctccttgt tcatgttgct cacaacaaga aatgggctaa tgctatgaat    5520
aataataaca aacactgcct tctgtcaggc cctgtgctga ataccgtctg catatgtata    5580
ggaaagggtt aactcagcag gtcttgtttg cccagactct gtacatttcc aagaaaggtc    5640
tgcctttagg actggtcctt ggccagctcc tggagaatga gctctcagct tttagaaaat    5700
tctatctgct aagaatagtt ttgcatgtct caggtcttgg gccacaaaat atcagtttaa    5760
tcagatggtt tatgttaaca agtatgattt atggcaaaca tagatctcta atctccattt    5820
ctctctcata tatctatatt tatctatcca tatatatgta cctatatata tcaaaatgaa    5880
agatatgttt atagcaattg catataaata gagagatagt atgtagtagg aagagagaca    5940
tagatattat tcttcatttt agaatgttat cttggtatgt ttaaaaggaa aaacttaaga    6000
tgtgttgcaa ttgcagtatg agtttcaggt atgtacatgt tatgtgtgtg tgtgagagac    6060
acacacaaac acatttcaaa catgttttat gtttaagctc aatattcaaa cacagaaata    6120
taacatctat tcttaatatg ttttatgtaa gtacagcagc agcattatta aatactgtat    6180
ttctatggtg attgaaaatt agtaggcaga gaatttttgt aatggttctt ataattttt    6240 gtaatagtaa atgattactt tttgtttagt atagtttat aatctataca tgaataaagt    6300
ggatatttct attcatatag aaatgtgatt tactctcatg tacttatcta catgctaaaa    6360
ccataagtta tcaattttag ttctgtgcca aggcactttt actgaataaa aataatcagc    6420 taatttttata ttttcctgat tcaaatttat atgcccgtgt aatgttccgg ggttttttttt    6480 tttaatttct gtaaatcaga atattcagat gttgaaaaag tctttgcctt cagatttaaa    6540
agataccttt gaaatgtagc atatcccaaa atgcaaccca gaggctggca atgtcaacat    6600
ttttctgttt taaaaaacct cttatgaaaa ctattgccat actaaatttt ttacttgctg    6660
atgacttaca gctggaaagg attctgtaca tataagacat caaatattga ggatactgga    6720
```

-continued

```
acttttaaat taatggcaaa gaaagtcaac aaaggaagtt catatgaaat caaactagta    6780
atatgattac aaaaaaaaaa gtttaaaatt tttcttggcc ccagtcttat catttctgag    6840
ccaaatacaa ttctatcgaa atcacctgaa actgaaatca ccattctagg ctggttttcc    6900
cataaagatg gactgctcca aaagaggaa tcaagaaaga atttggctca cagtgaatta     6960
ttcactttgt cttagttaag taaaaataaa atctgactgt taactacaga atcatttca     7020
aattctgtgg tgataataaa gtaatgacca cttttcagct ggagggacta acttcttttt    7080
ttttttgct gcatatatag ctgtggtaca ttttaatgtg aaatgatgac tgcatcagct     7140
tatatccatg gagcagattt tagcattcag cttgggtctc ccagtcaata tctacgagtc    7200
tcttcttaag gagatcgatg acacagatac atacagacta acaaatgtga taccaataat    7260
caagaattca ctcagttaag attttgccca ctgatttcca cacaagaaac ctagaattta    7320
ctagattctt gtgcctgtga ggctccactc atttccctga atcacaaaag ctacagagta    7380
tttagataga aatatacctta ctcttaacat gaaccattt aaatatatgt attactgtgt    7440
ccacaggagt acactttaaa gcagggactt cactcttcaa tctctccaat cacgtgttac    7500
ctaaagtggc atgtggttcc ctaaagctta ataactgaca ttgccttaaa aaaggggttt    7560
gcttcccgac taatgtggaa aaagtctgaa aaatgatttt aaatctttca ctaaatttct    7620
catttggtca cgtggaggaa aatgatttca ccaaatagat actctcatta atttttaat    7680
gtaattatc aaagaaatga aatatttaga taaattccag atttcccca ccatgagctt     7740
ctccgaaagt atactccatc acagactgct cactaagaag ctctactgca gtcaaagtga   7800
ccgaatttaa ggggacataa tgactactc tgctacacag aaacattatc catctctaac    7860
acttccctat gagatggaag acggacttct aatcaggtac cagagagggc tctgccaact    7920
tcagggcttt gatgaataag aatggttgag agcgctcatc ataatgaat tcagtataac     7980
tgagtgagaa agtgagagaa ccagagaaat aaatcctcat gtagaaaatt taggggtatg    8040
aaatgccaaa tgccagttaa ccaaagcttt ctttgtcata aagcaacttc tataaaaatt    8100
gctgaaaata aattcttcat ggctcaatgt gaatcagtaa tttccatctc tattacactg    8160
ttgtttaccc aaaaactatt tttaatgact aagactcaga gttgccaga gtgttttcca    8220
caaaacaact gttttgagat actccagatc tgtaatcaag taagtctgaa aaaccccaaa    8280
tacctcactc acctcttgga tatgcataaa gcacactaat atataacgtt ctaaaaagcc    8340
aatcattaaa accgttttat attgtttaag catttcctag acatatttgg ctacaaatct    8400
a                                                                   8401
```

<210> SEQ ID NO 5
<211> LENGTH: 8427
<212> TYPE: DNA
<213> ORGANISM: Homo sapiens

<400> SEQUENCE: 5

```
gcacctgcca ccacgcccag ctaatttct attttcagta gagatgaggt tttgccatgt     60
tggccaggct ggtctcgaac tcttgacctc aggtgatcca cccgcctcag cctaccaaag    120
agctgggatt acaggcgtga gccaccgcgc ctggccatat taacaaattt taaatcacaa    180
ctatgtgggg ggggaggcta gtattattac agcagattgg tttgctatat aaacaagtac    240
tttaaaaaat atttcttggg ccaggcgtgg tggctcacgc ctgtaatccc agcactttgg    300
gaggccgagg tgggcagatc acttgaggcc aagagttaag agaccagcct ggccaacatg    360
gtgaaacccc atctctacta aaaatataac aattagccag gcatggaggt gcatgcctgt    420
```

```
aattccagct gctcgagagg ctgaggcatg agaactgctg gatcctggga ggcagaggtt      480
gcagtgagct gatattgcgc cactgcactc catatccagc ctgggcaaca tggcaagact      540
ccgtctcaaa taaataaata aataaataaa taaaactaaa ggcagagttt tcttaaataa      600
acatggtagc cctcagcaac aatattgtaa gaactcctcg caagagaaaa agctggaata      660
agatactggc taagcaagta agaaaggcac tgccctgctt ctgcatacat tcaaactaag      720
acatatacat tgcagcttac acttacattt tccaatatcc ccaggcatcc ctttcccttc      780
tcaaacagcc aaaaggaacc agccatgcaa ataaaaatac aagttcaaga gcctaaaaga      840
agtcagtgtc ctaaaagaga aaattaatgt aaagaattaa gattttttga aactacactt      900
tctttctggg gctgtttact ggcctccaat acatcaatcc tgtaacactg tgaactacag      960
tgatagattg gtacatgctt ctaaacacaa cagaattttt ccaaggttac atacactgta     1020
acaaaagggg cattttgcag catcttattt tccttaatca actagtttgg atattctaac     1080
agtgcaaaca ttgtaaacaa taaattttca ttaccttttg aactttctga agtcaaccaa     1140
aggcttgtgg tatggatgca atgagtacta gacaggcaga gctgaatact agtcaaaata     1200
ttcagttact ggtgtgatag tccttttggg ggcatacatc acttagggag aaactgaggt     1260
gcaaggacat tttacacaca gcaaaaacat tctcaggaat ttgtcacatc attaccataa     1320
gccaaaaatc tcaaggtctt agaacagcct gagcttctga tcaaattata ttgtaaaaag     1380
agaggaaaaa aatgtgaagc gtgctatttt ttaaaataac agtaactact actactgctg     1440
ctgctgctaa ttctaaacgt ttactgagcc cttattatgt gccaagcacc gtgctaggta     1500
cggtcataga ttttaacaat taatccctgt aacaaccctc tgatattagt taataaaatt     1560
aaagtagaat cctcaccaaa aaaatttaaa cttttccaaat aaaaatataa ataaattatt     1620
aaagacattt cacctctttc tctgcctcag actacatttt caagtattaa atttacacta     1680
aaaccacatt tattttcagg aattccagtt aaagcgtaca gatattcaag atgttgacaa     1740
ttattacaga agaatcacag aactctgaaa ttaaatactg gcacagaaaa ccttccatcc     1800
aaccttacgg aacaactatc cccattttaa aaaaaagga acagcatata tatcaggctt     1860
gataataaga ggcttctcat gcccacacta gcaatgaatg atgccataat tataaagaga     1920
cctgtatcgc cacatgcata aaaataattt acatctgcta agtcaagttt tcaatatatt     1980
attttgtgtg taaaccttat agtagctgat aaaaaataca ataaactaat ctaaggtaaa     2040
ctaaaacact aggttgtttc tgaagactca ctttagaatt tgagcagcat aataatcata     2100
atattagtaa tcaaactact tagcagaaag ttcttagagg gctgggaagc tgtgtataat     2160
aaaatggagc agacaagaag gaagggtttt ccgtactgtt taaatcaact acaggtccca     2220
gcatgcagtg ctctaatctg aagttaagca aaaactgcaa tgcatactgg gacttgtagt     2280
aagtaaacca cgttatcaca gcaagtttca agaaagtctg aactatctag cacaatttga     2340
ctatatctta ttatcagagt ctaatcaaat ttaaatcaaa tttgtatgtt ctctgatgtg     2400
gcacacagtt tctctagcac ataccggaaa aagtatcaat atttagacca acattttcac     2460
attagaaaaa tcttacgtag gagaagcaca gaaaaaaatg ctgaaaaagc aaaaaaactt     2520
gatgaataaa aaatataatt tttgaaatag ttttttaaag tttgaatgga tccatttcaa     2580
cattctctaa tcctccccca caaaaagttt aattgttttg gccgggcgcg gtggctcacg     2640
cctgtaatcc caacacttta ggaggctgag gcgggtgaat tacgagatca agagatcgag     2700
accatcctgg ccaacatggt gaaaccatct ctactaaaaa tacaaaaatt agttgggcgt     2760
```

| | |
|---|---|
| ggtggcgcac gcctgtagtc ccagctactc aggaggctga gacaggagaa ttgcttgaac | 2820 |
| ctggaggtg gaggctgcag tgagctaata tcgcaccact gcactccagc ctggtgacag | 2880 |
| tgtgagattc attctcaaaa aaaaaaaaaa aaaagtttta attgttttaa caggttgctt | 2940 |
| tttaacaatt attcaagatg tattttataa ataattttc ttgaagaaaa ttctcagaag | 3000 |
| caaacattcc ccatattcta atattgccca ccaggaaata attttttag taatacgcac | 3060 |
| acacccate acaaaaacaa acaaaaaaca ctgaagttct gcttttgtca agtccttact | 3120 |
| caatatttat gccctccatt cctcacctct aattccctac acacacacac acacgcac | 3180 |
| acatccccac acacacacgc ttctacaaag aacacttaga aaaacagtat tccaactaca | 3240 |
| agcccacttc tctcatccac tgacctcttc tgaaaacaca aaagattttt taagctatca | 3300 |
| gtaacacgtc caaacacaag ctgataagtt tgagctagaa tttacatata tacagttgct | 3360 |
| acacaccctc ctattttctg caagtctgtg aaggaggct gggaaagaac taagtgcaat | 3420 |
| ctgcatcagg aggcctaaca caggtggtgg gttattttca ggcaacagca ccttcacaaa | 3480 |
| catgttttgg aatatagtcc aagaaattcc taacaaggaa agataagctg gcacacaaat | 3540 |
| ttaacgcaat ccagctaaaa atcatctgca acacatgcta ctacatttca ccataaagt | 3600 |
| gacgggctac tataaaggat ttgaagcttc gtcaatacaa catactgtcc ataaggccag | 3660 |
| agatagcagt tgccatggtt actatacca cttttatcag gaaattactg tcattacccc | 3720 |
| aaagttttgg gtacttattt aaaatttaaa aaaaacacac acaatttagg gttctgactg | 3780 |
| ttaattgagt gaaataatca actactgttt gatttgtaag tatgtcgctt tggagatgca | 3840 |
| catggttaac aatacttgga tctgcagcag aaaaaaaatc aattccttc tgctgctcct | 3900 |
| tctcctcaag tactgacagt ttgtattctc aatgcagcca aaacaataaa acaaaaccca | 3960 |
| tcttttggc ttctgtgttt aagttatttt tccctaggc ccacaaacag agtcaaaata | 4020 |
| aagcctagat catcaacctg ttaggcctca tcccttcct atccctcca tactggttca | 4080 |
| cttcttgac tacttagaaa aggcagaaaa catttctgta actgattcca agtatagaa | 4140 |
| aagaatagtt gccttcaact gagatatttt caccaaagtc ttttttattt actttttttt | 4200 |
| taaggcaggg agaggggaga gacttgcagg gtactgaaag ggagaagtgg aggagtattc | 4260 |
| aaattgccac acaagtctag tgtaagaaag ttgctttaga agagtccaaa ggatggctga | 4320 |
| acctcacata taatttctaa aagctttgga agagttcacc ataatttaa gactgaattg | 4380 |
| agggacaagt aatagaaaag ttattcataa agtctacttc aacatttta caaagataa | 4440 |
| ctattcaaaa atttaacaca catataagaa ttatacgaaa gcctacaaaa tagtatggcc | 4500 |
| acatatacac acaaacatac aaagtagaaa acataagcta tttaagaaat aattatctac | 4560 |
| aataaattca atgcaatgtt aacatattat ctctttttta aaaatcgca aagcagcaaa | 4620 |
| aacatacacc tgagaaaatt aatgtgatca aaacgttaaa gaattcttag gcctataaaa | 4680 |
| aaagcccatg tacaaaagct cctgagaagt caacataaat cattaatatt tcccagcaca | 4740 |
| aaataatatg aaaattcaaa catgtttcaa gaaatcagtt ctagatatag atataaaga | 4800 |
| attccattaa aggtcagaga cctaaaactt taattccttc ccttctctgt ttgaatagta | 4860 |
| attaaataca aaagccttca gcaataaaat actaaggata caaaatttaa aagcacatta | 4920 |
| atataagctt aacttcagta tgtcttcaca gaaagcttta ctattcactg tctgtaggat | 4980 |
| gaaaaagtta ataacaccct gagaggtttc attttatct aaacagttaa gtgttttct | 5040 |
| caccgttcac agaagcaagt ttctatattt actttctaaa gggggcaatt tcaaaagaat | 5100 |
| agtcacttct aaaatttaag atactatacc ttttgatagg ctcataaaca cagggttcct | 5160 |

```
aattatctat attttacttt aaaatgtttc tattccaaat ttgtgagcag agtttataag    5220
aaagctgaaa ctcaaggctt taaacttttg ggttattttt acacaaaaat atttcagtgc    5280
actcctctag atttgagtag tcatttcctt gtgcatcctt ctaaaataga aaacaaaaa     5340 tgatatatcc atatatacct aatactaaca catacagata tacatctttt tcactgtgaa    5400
acaagcttga aagctttagg cagtaagaat ttttcagaaa gttagcagag tcagtcaaaa    5460
cattcaaaac ttgaaccatg acatctgtta ctctgtcaat aagagtctat agaagaatca    5520
gggaacttac atactcacta aaatcaacta ctatcacatc acatcaatgg agaaatgaag    5580
aaaaactgta atagggggaca tacaattcac aggatcttca aaagggaaaa tgatcttttt    5640 tttttttta aattatgaga aactgactag gcagcatttt ttcaaaagca gcttcaaaac    5700
tataacaaag acattttgg taaccacagc agtatttaaa aaacaaaaat ttaggccggg     5760
cgtggtggct cacgcctata atcccagcac tttgggaggc caaggcaggt ggatcacctg    5820
agtcaggagt tcaagaccag cctgaccaac atggtgatac cccgtctcta ctcaaaatac    5880
aaaacttagc cgggcgtagt ggcggacacc tctataatca cagctactca ggaggctgag    5940
aggcaggaga atcgcttgaa cctgggaggc agaggttgca gtgagccgag atcacgccgt    6000
tgcactccag cctgggaaac agagcgagac tccgtctcaa aaataaaaa aataaaaaaa    6060 ctatagtgtc cagggtgcac tttaaatgta ttactttctc aactgatatg gaaaagtta    6120 gcatttaaag acagaagctt ctgtccatgt attaattagt tacctatctc aacaacttaa    6180
tatctgcatg ctttcttacc atttatgaag aacttttata tgtattatct catttggtct    6240
tactgagaaa acagtatttt gcctacaaaa tagacaaaat tcaaagcaga tttatcaaac    6300
tttctagcat ccccaaattt ttaaaacttc gacacaaaac tttacaagca accacagtgg    6360
catgatattt tcagtgataa tcaattcacc taacactaac agagtttcaa aggaccatgt    6420
gctataaatg ctatgaaact gttaaagtag ctatattcat ctttatgcag ttactgttac    6480
atcaacaatg acctaccact gatacaactt gacttacagt tcaagaatct cagtctttgc    6540
aggctaactt aagtcatca accatatgta tttataaagc cgagtgccta aaaattgatc    6600
tatattagaa tcatagtctg taaatccgag gggaaaaaac tacaagaagt ctaaattttt    6660
ttcaacacac tatacccctt tccaaaatct caactactct atatcctatt tgtattaata    6720 ttatgggat gataacaagg cttaaagccc taaatcatac caactacttt tgtttataac    6780
aattacaaat aattttttaa aatacatgct caacatccca ctcatcaaca caagactaat    6840
tccccttcca aataaaataa ttctaaacag tgctctgtac caagggccag aatccttata    6900
ctatccgcaa tcgcacatct actttgtaca gtcaaagact tcactttcaa gtagcaaaca    6960
ttatttatga atgaatttt taaatggact tactcaaaat ctttctggaa ctttaaggtg    7020
ttaatcctgt tgcttagctg aagctaagca gagctgtaat aagtagcaag accctcaaaa    7080
ttcaaaaatt tcctttatct tgctgtagca cctcctgctg gatagcattt agagatcttc    7140
atgtaagcag aagaagagta tttcagaggc agctccttcc agaagactga ataggaaaaa    7200
ggatggaccc ttcaaagcta aagaaatag gccccatcca tcacttatac cttctaaaaa    7260
tacaatttag cccaggtagg tgtctttttc atctattact actccagttc cacaaagact    7320
tgcctcagtc caaaatacaa catgcttaaa taaagcctgc aaaattgtct aaaaactaag    7380
ttaaaaagca ttcaatagca cccaagcaaa acactttatt atgggcagcc aagcaatgtc    7440
agtcaaactg taaatactat tatgttacca aaagcaaaag tctgatgtta aaaaaaaaa    7500
```

| | |
|---|---:|
| aaaaaaagcc cctggaatat tcgtaacatg ttagccagat gtttgtgttt tgagaacttt | 7560 |
| gtgcactatt actatgctct tcacttaagg atagttgtac atctacaaac gttttaagta | 7620 |
| cagaaatttt tttataaaca ttagcataac tgtacacaaa atttcctctt tgccatgaaa | 7680 |
| agataggtcc tgggatttga aaatgtattt ttcagacatt tttaatgacc ccctaaaata | 7740 |
| aactagtttt aagcccacaa caccgattcc ataaacaagt aaagacagaa gaagagaata | 7800 |
| agaaggaact taccaaaatt aaaatgaata atagtatttc cagtaaaaat gtagtaacag | 7860 |
| tttccaacaa tgctgtaaac caaataaatt gtgaaactta aaaaggaag gaggggccca | 7920 |
| gtcttcaaag accaaaagca aagctgacct atttatttct attgcttaga gtgaacacca | 7980 |
| gatgtaaaca aatatcataa acactgaaaa gtacgcttac atggtttagc ctcaatttca | 8040 |
| gtacccttac caggccctca ataaagctac agatgttggt gagaactcgc tcaaaaagga | 8100 |
| gataattcca gccctcgcc ttaaagaatc cctatcaagt gaacctgtga aaagacttcc | 8160 |
| ttcccagagt gcacaactgc tttaaaaaaa aaaactttc atcagcccaa attaatctga | 8220 |
| ttctaatatt caactatcca ttatttatat ataaatgttc ttccctctct aactttccca | 8280 |
| gctcgagcat ctacattcct gacaccgact attagcaaaa atgcacaact ccttccccag | 8340 |
| ctatggggca aatctttgaa atctgaaaca cagcccacaaa gttcactgtc aaggccaggt | 8400 |
| gatgaggccc acacatgccc ggacctt | 8427 |

<210> SEQ ID NO 6
<211> LENGTH: 1704
<212> TYPE: DNA
<213> ORGANISM: Artificial Sequence
<220> FEATURE:
<223> OTHER INFORMATION: Synthetic

<400> SEQUENCE: 6

| | |
|---|---:|
| ggtaccaccc aagctggcta ggtaagcttg ctagcgccac catggtgctg cagacccagg | 60 |
| tgttcatctc cctgctgctg tggatctccg gcgcatatgg cgatatcgtg atgattaaac | 120 |
| gtacggtggc cgccccctcc gtgttcatct tccccccctc cgacgagcag ctgaagtccg | 180 |
| gcaccgcctc cgtggtgtgc ctgctgaata acttctaccc cagagaggcc aaggtgcagt | 240 |
| ggaaggtgga caacgccctg cagtccggga actcccagga gagcgtgacc gagcaggaca | 300 |
| gcaaggacag cacctacagc ctgagcagca ccctgaccct gagcaaagcc gactacgaga | 360 |
| agcacaaggt gtacgcctgc gaggtgaccc accagggcct gagctccccc gtcaccaaga | 420 |
| gcttcaacag ggggagtgt taggggcccg tttaaacggg tggcatccct gtgacccctc | 480 |
| cccagtgcct ctcctggccc tggaagttgc cactccagtg cccaccagcc ttgtcctaat | 540 |
| aaaattaagt tgcatcattt tgtctgacta ggtgtccttc tataatatta tggggtggag | 600 |
| gggggtggta tggagcaagg gcaagttgg gaagacaacc tgtagggcct gcggggtcta | 660 |
| ttgggaacca agctggagtg cagtggcaca atcttggctc actgcaatct ccgcctcctg | 720 |
| ggttcaagcg attctcctgc ctcagcctcc cgagttgttg ggattccagg catgcatgac | 780 |
| caggctcacc taattttgt ttttttggta gagacggggt ttcaccatat tggccaggct | 840 |
| ggtctccaac tcctaatctc aggtgatcta cccaccttgg cctcccaaat tgctgggatt | 900 |
| acaggcgtga accactgctc cacgcgccct gtagcggcgc attaagcgcg cgggtgtgg | 960 |
| tggttacgcg cagcgtgacc gctacacttg ccagcgccct agcgcccgct cctttcgctt | 1020 |
| tcttcccttc ctttctcgcc acgttcgccg gctttccccg tcaagctcta aatcgggggc | 1080 |
| tccctttagg gttccgattt agtgctttac ggcacctcga ccccaaaaaa cttgattagg | 1140 |

```
gtgatggttc acgtagtggg ccatcgccct gatagacggt ttttcgccct ttgacgttgg      1200
agtccacgtt cttaatagt ggactcttgt tccaaactgg aacaacactc aaccctatct       1260
cggtctattc ttttgattta taagggattt tgccgatttc ggcctattgg ttaaaaaatg     1320
agctgattta acaaaattt aacgcgaatt aattctgtgg aatgtgtgtc agttagggtg      1380
tggaaagtcc ccaggctccc cagcaggcag aagtatgcaa agcatgcatc tcaattagtc    1440
agcaaccagg tgtggaaagt ccccaggctc ccagcaggc agaagtatgc aaagcatgca     1500
tctcaattag tcagcaacca tagtcccgcc cctaactccg cccatcccgc cctaactcc     1560 gcccagttcc gcccattctc cgccccatgg ctgactaatt ttttttattt atgcagaggc    1620
cgaggccgcc tctgcctctg agctattcca gaagtagtga ggaggctttt ttggaggcct    1680
aggcttttgc aaaaagctcc cggg                                            1704

<210> SEQ ID NO 7
<211> LENGTH: 1120
<212> TYPE: DNA
<213> ORGANISM: Artificial Sequence
<220> FEATURE:
<223> OTHER INFORMATION: Synthetic

<400> SEQUENCE: 7
tgctagcgcc accatgaaac acctgtggtt cttcctcctg ctggtggcag ctcccagatg     60
ggtgctgagc caggtgcaat gtgcaggcg gttagctcag cctccaccaa gggcccaagc     120 gtcttcccc tggcaccctc ctccaagagc acctctggcg gcacagccgc cctgggctgc    180
ctggtcaagg actacttccc cgaacccgtg accgtgagct ggaactcagg cgccctgacc   240
agcggcgtgc acaccttccc cgctgtcctg cagtcctcag gactctactc cctcagcagc  300
gtggtgaccg tgccctccag cagcttgggc acccagacct acatctgcaa cgtgaatcac   360
aagcccagca caccaaggt ggacaagaga gttgagccca atcttgtga caaaactcac     420 acatgcccac cctgcccagc acctgaactc ctggggggac cctcagtctt cctcttcccc     480
ccaaaaccca aggacaccct catgatctcc cggaccctg aggtcacatg cgtggtggtg    540
gacgtgagcc acgaagaccc tgaggtcaag ttcaactggt acgtggacgg cgtggaggtg    600
cataatgcca agacaaagcc ccgggaggag cagtacaaca gcacgtaccg ggtggtcagc   660
gtcctcaccg tcctgcacca ggactggctg aatggcaagg agtacaagtg caaggtctcc   720
aacaaagccc tcccagcccc catcgagaaa accatctcca agccaaagg ccagccccgg    780 gaaccacagg tgtacacccct gcccccatcc cgggaggaga tgaccaagaa ccaggtcagc   840
ctgacctgcc tggtcaaagg cttctatccc agcgacatcg ccgtggagtg ggagagcaat   900
ggccagcccg agaacaacta caagaccacc cctcccgtgc tggactccga cggctccttc   960
ttcctctaca gcaagctcac cgtggacaag agcaggtggc agcagggcaa cgtcttctca  1020
tgctccgtga tgcatgaggc tctgcacaac cactacaccc agaagagcct ctccctgtct  1080
cccggcaaat gagatatcgg gcccgtttaa acgggtggca                         1120

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
```
tactagcggt tttacgggcg                                           20

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
tcgaacagga ggagcagaga gcga                                      24

<210> SEQ ID NO 10
<211> LENGTH: 37
<212> TYPE: DNA
<213> ORGANISM: Artificial Sequence
<220> FEATURE:
<223> OTHER INFORMATION: Synthetic

<400> SEQUENCE: 10
aaagctagca tgctgctgct gctgctgctg ctgggcc                        37

<210> SEQ ID NO 11
<211> LENGTH: 36
<212> TYPE: DNA
<213> ORGANISM: Artificial Sequence
<220> FEATURE:
<223> OTHER INFORMATION: Synthetic

<400> SEQUENCE: 11
aaaagatctt catgtctgct cgaagcggcc ggccgc                         36

<210> SEQ ID NO 12
<211> LENGTH: 78
<212> TYPE: DNA
<213> ORGANISM: Artificial Sequence
<220> FEATURE:
<223> OTHER INFORMATION: Synthetic

<400> SEQUENCE: 12
ggaaattgag aagtatcatt cacaacagta ccacaaacat gaaataaatg tggatcctat    60
taatagtaat caattacg                                             78

<210> SEQ ID NO 13
<211> LENGTH: 78
<212> TYPE: DNA
<213> ORGANISM: Artificial Sequence
<220> FEATURE:
<223> OTHER INFORMATION: Synthetic

<400> SEQUENCE: 13
ctcattctgt gggttgtcat ttcacttcct tgatgctatc ctttcaagca aaatcctagt    60
caataatcaa tgtcaacg                                             78

<210> SEQ ID NO 14
<211> LENGTH: 77
<212> TYPE: DNA
<213> ORGANISM: Artificial Sequence
<220> FEATURE:
<223> OTHER INFORMATION: Synthetic

<400> SEQUENCE: 14
cttattttct aagtagtata gacttaattg tgagaacaaa ataaaaactt ggatcctatt    60
aatagtaatc aattacg                                              77

```
<210> SEQ ID NO 15
<211> LENGTH: 74
<212> TYPE: DNA
<213> ORGANISM: Artificial Sequence
<220> FEATURE:
<223> OTHER INFORMATION: Synthetic

<400> SEQUENCE: 15
ctcttcccat tctcatttga atctacttca aaaggtttac catactaaga cctagtcaat    60
aatcaatgtc aacg                                                       74

<210> SEQ ID NO 16
<211> LENGTH: 79
<212> TYPE: DNA
<213> ORGANISM: Artificial Sequence
<220> FEATURE:
<223> OTHER INFORMATION: Synthetic

<400> SEQUENCE: 16
cgcctgtaat cccagcactt tgggaggctg aggcgggtgg atcacctgag gtcgatccta    60
ttaatagtaa tcaattacg                                                  79

<210> SEQ ID NO 17
<211> LENGTH: 77
<212> TYPE: DNA
<213> ORGANISM: Artificial Sequence
<220> FEATURE:
<223> OTHER INFORMATION: Synthetic

<400> SEQUENCE: 17
catacagaag ccagtttgaa ctgagacctc actccatttc ttacaagtta tgccctagtc    60
aataatcaat gtcaacg                                                    77

<210> SEQ ID NO 18
<211> LENGTH: 78
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 18
naccgtttta tattgtttaa gcatttccta gacatatttg gctacaaatc tagatcctat    60
taatagtaat caattacg                                                   78

<210> SEQ ID NO 19
<211> LENGTH: 77
<212> TYPE: DNA
<213> ORGANISM: Artificial Sequence
<220> FEATURE:
<223> OTHER INFORMATION: Synthetic

<400> SEQUENCE: 19
gatcttaggg gggctgatta tataaaacaa tagaaatgta gtcttagatg aaacctagtc    60
aataatcaat gtcaacg                                                    77

<210> SEQ ID NO 20
<211> LENGTH: 79
<212> TYPE: DNA
```

<213> ORGANISM: Artificial Sequence
<220> FEATURE:
<223> OTHER INFORMATION: Synthetic

<400> SEQUENCE: 20
cacaaagttc actgtcaagg ccaggtgatg aggcccacac atgcccggac cttgatccta    60
ttaatagtaa tcaattacg                                                 79

<210> SEQ ID NO 21
<211> LENGTH: 78
<212> TYPE: DNA
<213> ORGANISM: Artificial Sequence
<220> FEATURE:
<223> OTHER INFORMATION: Synthetic

<400> SEQUENCE: 21
caaaacctca tctctactga aaatagaaaa ttagctgggc gtggtggcag gtgccctagt    60
caataatcaa tgtcaacg                                                  78

<210> SEQ ID NO 22
<211> LENGTH: 38
<212> TYPE: DNA
<213> ORGANISM: Artificial Sequence
<220> FEATURE:
<223> OTHER INFORMATION: Synthetic

<400> SEQUENCE: 22
aaaactagtc agagaggaat ctttgcagct aatggacc                            38

<210> SEQ ID NO 23
<211> LENGTH: 35
<212> TYPE: DNA
<213> ORGANISM: Artificial Sequence
<220> FEATURE:
<223> OTHER INFORMATION: Synthetic

<400> SEQUENCE: 23
aaagatatcc ctagccagct tgggtggtac caagc                               35

<210> SEQ ID NO 24
<211> LENGTH: 35
<212> TYPE: DNA
<213> ORGANISM: Artificial Sequence
<220> FEATURE:
<223> OTHER INFORMATION: Synthetic

<400> SEQUENCE: 24
aaaactagtc tgtggaatgt gtgtcagtta gggtg                               35

<210> SEQ ID NO 25
<211> LENGTH: 34
<212> TYPE: DNA
<213> ORGANISM: Artificial Sequence
<220> FEATURE:
<223> OTHER INFORMATION: Synthetic

<400> SEQUENCE: 25
aaagatatca gcttttttgca aaagcctagg cctc                               34

<210> SEQ ID NO 26
<211> LENGTH: 77
<212> TYPE: DNA
<213> ORGANISM: Artificial Sequence
<220> FEATURE:
<223> OTHER INFORMATION: Synthetic

<400> SEQUENCE: 26
ggaaattgag aagtatcatt cacaacagta ccacaaacat gaaataaatg tgctagtcag      60
agaggaatct ttgcagc                                                    77

<210> SEQ ID NO 27
<211> LENGTH: 79
<212> TYPE: DNA
<213> ORGANISM: Artificial Sequence
<220> FEATURE:
<223> OTHER INFORMATION: Synthetic

<400> SEQUENCE: 27
ggaaattgag aagtatcatt cacaacagta ccacaaacat gaaataaatg tgctagtctg      60
tggaatgtgt gtcagttag                                                  79

<210> SEQ ID NO 28
<211> LENGTH: 78
<212> TYPE: DNA
<213> ORGANISM: Artificial Sequence
<220> FEATURE:
<223> OTHER INFORMATION: Synthetic

<400> SEQUENCE: 28
ctcattctgt gggttgtcat ttcacttcct tgatgctatc ctttcaagca aaattttaaa      60
actttatcca tctttgca                                                   78

<210> SEQ ID NO 29
<211> LENGTH: 76
<212> TYPE: DNA
<213> ORGANISM: Artificial Sequence
<220> FEATURE:
<223> OTHER INFORMATION: Synthetic

<400> SEQUENCE: 29
cttattttct aagtagtata gacttaattg tgagaacaaa ataaaaactt gctagtcaga      60
gaggaatctt tgcagc                                                     76

<210> SEQ ID NO 30
<211> LENGTH: 78
<212> TYPE: DNA
<213> ORGANISM: Artificial Sequence
<220> FEATURE:
<223> OTHER INFORMATION: Synthetic

<400> SEQUENCE: 30
cttattttct aagtagtata gacttaattg tgagaacaaa ataaaaactt gctagtctgt      60
ggaatgtgtg tcagttag                                                   78

<210> SEQ ID NO 31
<211> LENGTH: 80
<212> TYPE: DNA
<213> ORGANISM: Artificial Sequence
<220> FEATURE:
<223> OTHER INFORMATION: Synthetic

<400> SEQUENCE: 31
ctcttcccat tctcatttga atctacttca aaaggtttac catactaaga actagttttta     60 aaactttatc catctttgca                                                 80

<210> SEQ ID NO 32

<210> SEQ ID NO 32
<211> LENGTH: 28
<212> TYPE: DNA
<213> ORGANISM: Artificial Sequence
<220> FEATURE:
<223> OTHER INFORMATION: Synthetic

<400> SEQUENCE: 32
ccacgcgccc tgtagcggcg cattaagc                                    28

<210> SEQ ID NO 33
<211> LENGTH: 30
<212> TYPE: DNA
<213> ORGANISM: Artificial Sequence
<220> FEATURE:
<223> OTHER INFORMATION: Synthetic

<400> SEQUENCE: 33
aaacccggga gcttttttgca aaagcctagg                                 30

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
cgcggccgca ctagtgacgt                                             20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
cactagtgcg gccgcgacgt                                             20

<210> SEQ ID NO 36
<211> LENGTH: 25
<212> TYPE: DNA
<213> ORGANISM: Artificial Sequence
<220> FEATURE:
<223> OTHER INFORMATION: Synthetic

<400> SEQUENCE: 36
aaacatatgg cgacatccag atgac                                       25

<210> SEQ ID NO 37
<211> LENGTH: 26
<212> TYPE: DNA
<213> ORGANISM: Artificial Sequence
<220> FEATURE:
<223> OTHER INFORMATION: Synthetic

<400> SEQUENCE: 37
aaacgtacgc ttgatctcca ccttgg                                      26

<210> SEQ ID NO 38
<211> LENGTH: 26
<212> TYPE: DNA
<213> ORGANISM: Artificial Sequence
<220> FEATURE:
<223> OTHER INFORMATION: Synthetic

<400> SEQUENCE: 38
aaagctgagc caggtgcagc tgcagg                                   26

<210> SEQ ID NO 39
<211> LENGTH: 28
<212> TYPE: DNA
<213> ORGANISM: Artificial Sequence
<220> FEATURE:
<223> OTHER INFORMATION: Synthetic

<400> SEQUENCE: 39
aaagctgagc tcacggtcac cagggttc                                 28

<210> SEQ ID NO 40
<211> LENGTH: 44
<212> TYPE: DNA
<213> ORGANISM: Artificial Sequence
<220> FEATURE:
<223> OTHER INFORMATION: Synthetic

<400> SEQUENCE: 40
cttttgcaaa aagcttcgcg ttacataact tacggtaaat ggcc               44

<210> SEQ ID NO 41
<211> LENGTH: 43
<212> TYPE: DNA
<213> ORGANISM: Artificial Sequence
<220> FEATURE:
<223> OTHER INFORMATION: Synthetic

<400> SEQUENCE: 41
ttcatggtgg cgctagcccg cagatatcga tccgagctcg gta                43

<210> SEQ ID NO 42
<211> LENGTH: 44
<212> TYPE: DNA
<213> ORGANISM: Artificial Sequence
<220> FEATURE:
<223> OTHER INFORMATION: Synthetic

<400> SEQUENCE: 42
tgacgtcgac aagcttcgcg ttacataact tacggtaaat ggcc               44

<210> SEQ ID NO 43
<211> LENGTH: 107
<212> TYPE: DNA
<213> ORGANISM: Artificial Sequence
<220> FEATURE:
<223> OTHER INFORMATION: Synthetic

<400> SEQUENCE: 43
ctggatgtcg ccatatgcgc cggagatcca cagcagcagg gagatgaaca cctgggtctg    60
cagcaccatg gtggcgctag cccgcagata tcgatccgag ctcggta                  107

<210> SEQ ID NO 44
<211> LENGTH: 80
<212> TYPE: DNA
<213> ORGANISM: Artificial Sequence
<220> FEATURE:
<223> OTHER INFORMATION: Synthetic

<400> SEQUENCE: 44
ctcttcccat tctcatttga atctacttca aaaggtttac catactaaga ctcgaggcac    60
tagtgacgtc aggtggcact                                                80

<210> SEQ ID NO 45
<211> LENGTH: 80
<212> TYPE: DNA
<213> ORGANISM: Artificial Sequence
<220> FEATURE:
<223> OTHER INFORMATION: Synthetic

<400> SEQUENCE: 45
ctcttcccat tctcatttga atctacttca aaaggtttac catactaaga gcactagtga      60
cgtcaggtgg cacttttcgg                                                  80

<210> SEQ ID NO 46
<211> LENGTH: 79
<212> TYPE: DNA
<213> ORGANISM: Artificial Sequence
<220> FEATURE:
<223> OTHER INFORMATION: Synthetic

<400> SEQUENCE: 46
catgcacaga ttagccattt agtacttact aaatcaaact caatttctga agtctagtta      60
ttaatagtaa tcaattacg                                                   79

<210> SEQ ID NO 47
<211> LENGTH: 80
<212> TYPE: DNA
<213> ORGANISM: Artificial Sequence
<220> FEATURE:
<223> OTHER INFORMATION: Synthetic

<400> SEQUENCE: 47
ctcattctgt gggttgtcat ttcacttcct tgatgctatc ctttcaagca aaattcaata      60
atcaatgtca acgcgtatat                                                  80

<210> SEQ ID NO 48
<211> LENGTH: 80
<212> TYPE: DNA
<213> ORGANISM: Artificial Sequence
<220> FEATURE:
<223> OTHER INFORMATION: Synthetic

<400> SEQUENCE: 48
acactggtca aagggacagg tcattgttat gctggcaatg caggctgctg aaaactagtt      60
attaatagta atcaattacg                                                  80

<210> SEQ ID NO 49
<211> LENGTH: 80
<212> TYPE: DNA
<213> ORGANISM: Artificial Sequence
<220> FEATURE:
<223> OTHER INFORMATION: Synthetic

<400> SEQUENCE: 49
actgtagctt cttattttttt acctgcagtg cattcctgta aaagtagtgt ggagtcaata     60
atcaatgtca acgcgtatat                                                  80

<210> SEQ ID NO 50
<211> LENGTH: 80
<212> TYPE: DNA
<213> ORGANISM: Artificial Sequence
<220> FEATURE:
<223> OTHER INFORMATION: Synthetic

<400> SEQUENCE: 50

```
ctggaaattg agaagtatca ttcacaacag taccacaaac atgaaataaa tgtgctagtt    60
attaatagta atcaattacg                                                80
```

<210> SEQ ID NO 51
<211> LENGTH: 80
<212> TYPE: DNA
<213> ORGANISM: Artificial Sequence
<220> FEATURE:
<223> OTHER INFORMATION: Synthetic

<400> SEQUENCE: 51

```
ccaagcttgt ccaaccgcgg cctgcaggct gcatgcagcc tgtgaaggct ttgatcaata    60
atcaatgtca acgcgtatat                                                80
```

<210> SEQ ID NO 52
<211> LENGTH: 80
<212> TYPE: DNA
<213> ORGANISM: Artificial Sequence
<220> FEATURE:
<223> OTHER INFORMATION: Synthetic

<400> SEQUENCE: 52

```
tcaatcattt atcaatttta tcttcaaagt ccctcacttc agggagatga tatactagtt    60
attaatagta atcaattacg                                                80
```

<210> SEQ ID NO 53
<211> LENGTH: 80
<212> TYPE: DNA
<213> ORGANISM: Artificial Sequence
<220> FEATURE:
<223> OTHER INFORMATION: Synthetic

<400> SEQUENCE: 53

```
atatataaaa gttcatgtat atataaaatc atgcaataca cggccttttg tgactcaata    60
atcaatgtca acgcgtatat                                                80
```

<210> SEQ ID NO 54
<211> LENGTH: 80
<212> TYPE: DNA
<213> ORGANISM: Artificial Sequence
<220> FEATURE:
<223> OTHER INFORMATION: Synthetic

<400> SEQUENCE: 54

```
cgcataaaag gaaaagcatc cttaaaataa acaccatcaa tggctcctcg gtggctagtt    60
attaatagta atcaattacg                                                80
```

<210> SEQ ID NO 55
<211> LENGTH: 79
<212> TYPE: DNA
<213> ORGANISM: Artificial Sequence
<220> FEATURE:
<223> OTHER INFORMATION: Synthetic

<400> SEQUENCE: 55

```
gggaggctac agcttgcctc tctaaccact aaaaggcatg accctcctca aagctagtta    60
ttaatagtaa tcaattacg                                                 79
```

<210> SEQ ID NO 56
<211> LENGTH: 80
<212> TYPE: DNA

<213> ORGANISM: Artificial Sequence
<220> FEATURE:
<223> OTHER INFORMATION: Synthetic

<400> SEQUENCE: 56

```
tctggcttcc ctgggccacg ctggaagaag aattgtcttg cgccacacat aaaactagtt    60
attaatagta atcaattacg                                                80
```

<210> SEQ ID NO 57
<211> LENGTH: 80
<212> TYPE: DNA
<213> ORGANISM: Artificial Sequence
<220> FEATURE:
<223> OTHER INFORMATION: Synthetic

<400> SEQUENCE: 57

```
agctgatttt tacgttaaat gtaacatgta aagaaatata tgtgtgtttt tagatcaata    60
atcaatgtca acgcgtatat                                                80
```

<210> SEQ ID NO 58
<211> LENGTH: 80
<212> TYPE: DNA
<213> ORGANISM: Artificial Sequence
<220> FEATURE:
<223> OTHER INFORMATION: Synthetic

<400> SEQUENCE: 58

```
gtgaagagga ggagatgtca aaattcaaag tcttaaatga tgtagtttta agtactagtt    60
attaatagta atcaattacg                                                80
```

<210> SEQ ID NO 59
<211> LENGTH: 80
<212> TYPE: DNA
<213> ORGANISM: Artificial Sequence
<220> FEATURE:
<223> OTHER INFORMATION: Synthetic

<400> SEQUENCE: 59

```
atgacacttg atattgttgt ttatattgct ggttagtatg tgccttcatt tacctcaata    60
atcaatgtca acgcgtatat                                                80
```

<210> SEQ ID NO 60
<211> LENGTH: 80
<212> TYPE: DNA
<213> ORGANISM: Artificial Sequence
<220> FEATURE:
<223> OTHER INFORMATION: Synthetic

<400> SEQUENCE: 60

```
aaaaacaaaa ctggagtaaa caagatgaat tgttttaata gaggcactgt attactagtt    60
attaatagta atcaattacg                                                80
```

<210> SEQ ID NO 61
<211> LENGTH: 80
<212> TYPE: DNA
<213> ORGANISM: Artificial Sequence
<220> FEATURE:
<223> OTHER INFORMATION: Synthetic

<400> SEQUENCE: 61

```
atacaatgtt ccatgtattc tgtgcctgaa cctatgcagc tgatgtagct gaagtcaata    60
atcaatgtca acgcgtatat                                                80
```

<210> SEQ ID NO 62
<211> LENGTH: 80
<212> TYPE: DNA
<213> ORGANISM: Artificial Sequence
<220> FEATURE:
<223> OTHER INFORMATION: Synthetic

<400> SEQUENCE: 62
gatcttattt tctaagtagt atagacttaa ttgtgagaac aaaataaaaa cttgctagtt    60
attaatagta atcaattacg                                                80

<210> SEQ ID NO 63
<211> LENGTH: 80
<212> TYPE: DNA
<213> ORGANISM: Artificial Sequence
<220> FEATURE:
<223> OTHER INFORMATION: Synthetic

<400> SEQUENCE: 63
tgttgttttc agccactaag tttgaggtga tttgttctgg cagtcctagg aaactcaata    60
atcaatgtca acgcgtatat                                                80

<210> SEQ ID NO 64
<211> LENGTH: 80
<212> TYPE: DNA
<213> ORGANISM: Artificial Sequence
<220> FEATURE:
<223> OTHER INFORMATION: Synthetic

<400> SEQUENCE: 64
agcctacact acccttttgca gcctttggta actatccttc tgctgtctac ctcctcaata    60
atcaatgtca acgcgtatat                                                80

<210> SEQ ID NO 65
<211> LENGTH: 80
<212> TYPE: DNA
<213> ORGANISM: Artificial Sequence
<220> FEATURE:
<223> OTHER INFORMATION: Synthetic

<400> SEQUENCE: 65
aggagctcct gaatgaagga catcactcag ctgtgttaag tatctggaac aatactagtt    60
attaatagta atcaattacg                                                80

<210> SEQ ID NO 66
<211> LENGTH: 80
<212> TYPE: DNA
<213> ORGANISM: Artificial Sequence
<220> FEATURE:
<223> OTHER INFORMATION: Synthetic

<400> SEQUENCE: 66
gacataaaat gtaagatatg atatgctatg taagatatga tacctgcctt aaaatcaata    60
atcaatgtca acgcgtatat                                                80

<210> SEQ ID NO 67
<211> LENGTH: 80
<212> TYPE: DNA
<213> ORGANISM: Artificial Sequence
<220> FEATURE:
<223> OTHER INFORMATION: Synthetic

<400> SEQUENCE: 67
cactgcttga tacttactgt ggactttgaa aattatgaat gtgtgtgtgt gtgtctagtt    60
attaatagta atcaattacg    80

<210> SEQ ID NO 68
<211> LENGTH: 80
<212> TYPE: DNA
<213> ORGANISM: Artificial Sequence
<220> FEATURE:
<223> OTHER INFORMATION: Synthetic

<400> SEQUENCE: 68
caattacatt ccagtgatct gctacttaga atgcatgact gaactcctgg gtggtcaata    60
atcaatgtca acgcgtatat    80

<210> SEQ ID NO 69
<211> LENGTH: 80
<212> TYPE: DNA
<213> ORGANISM: Artificial Sequence
<220> FEATURE:
<223> OTHER INFORMATION: Synthetic

<400> SEQUENCE: 69
ttattttgaa gagaaactcc tggttcccac ttaaaatcct ttcttgtttc caagctagtt    60
attaatagta atcaattacg    80

<210> SEQ ID NO 70
<211> LENGTH: 80
<212> TYPE: DNA
<213> ORGANISM: Artificial Sequence
<220> FEATURE:
<223> OTHER INFORMATION: Synthetic

<400> SEQUENCE: 70
aagcagtgtg tgtttacctg catgtgtatg tgaattaact ctgttcctga ggcatcaata    60
atcaatgtca acgcgtatat    80

<210> SEQ ID NO 71
<211> LENGTH: 80
<212> TYPE: DNA
<213> ORGANISM: Artificial Sequence
<220> FEATURE:
<223> OTHER INFORMATION: Synthetic

<400> SEQUENCE: 71
attgcatgtt ctcatttatt tgtgggatgt aaaaatcaaa acaatagaac gtatctagtt    60
attaatagta atcaattacg    80

<210> SEQ ID NO 72
<211> LENGTH: 80
<212> TYPE: DNA
<213> ORGANISM: Artificial Sequence
<220> FEATURE:
<223> OTHER INFORMATION: Synthetic

<400> SEQUENCE: 72
ttgggaggcc gcagctggta gatcacttga ggccacgaat ttgacaccag caggtcaata    60
atcaatgtca acgcgtatat    80

<210> SEQ ID NO 73
<211> LENGTH: 79

```
<212> TYPE: DNA
<213> ORGANISM: Artificial Sequence
<220> FEATURE:
<223> OTHER INFORMATION: Synthetic

<400> SEQUENCE: 73
atcccctgct ctgctaaaaa agaatggatg ttgactctca ggccctagtt cttgatccta    60
ttaatagtaa tcaattacg                                                 79

<210> SEQ ID NO 74
<211> LENGTH: 78
<212> TYPE: DNA
<213> ORGANISM: Artificial Sequence
<220> FEATURE:
<223> OTHER INFORMATION: Synthetic

<400> SEQUENCE: 74
ctaaagtgct gggattacag gcataagcca ccgtgcccgg ctggagcatt gggatcctat    60
taatagtaat caattacg                                                  78

<210> SEQ ID NO 75
<211> LENGTH: 75
<212> TYPE: DNA
<213> ORGANISM: Artificial Sequence
<220> FEATURE:
<223> OTHER INFORMATION: Synthetic

<400> SEQUENCE: 75
actacttaca catttcgagt tttaaataag gcgttcaata tagagtgaac acctagtcaa    60
taatcaatgt caacg                                                     75

<210> SEQ ID NO 76
<211> LENGTH: 77
<212> TYPE: DNA
<213> ORGANISM: Artificial Sequence
<220> FEATURE:
<223> OTHER INFORMATION: Synthetic

<400> SEQUENCE: 76
caggcataag ccaccgcacc cggccacccc ttactaattt ttagtaacgt cgatcctatt    60
aatagtaatc aattacg                                                   77

<210> SEQ ID NO 77
<211> LENGTH: 76
<212> TYPE: DNA
<213> ORGANISM: Artificial Sequence
<220> FEATURE:
<223> OTHER INFORMATION: Synthetic

<400> SEQUENCE: 77
ctgattgact ttgacctctg ctttccaact ttgccccaaa gaaagttagt cacctagtca    60
ataatcaatg tcaacg                                                    76

<210> SEQ ID NO 78
<211> LENGTH: 77
<212> TYPE: DNA
<213> ORGANISM: Artificial Sequence
<220> FEATURE:
<223> OTHER INFORMATION: Synthetic

<400> SEQUENCE: 78
ttcaatgaaa caagctctgt gaggctcatt tgtacccatt ttgttcagta ctgcctagtc    60
```

-continued aataatcaat gtcaacg                                              77

<210> SEQ ID NO 79
<211> LENGTH: 77
<212> TYPE: DNA
<213> ORGANISM: Artificial Sequence
<220> FEATURE:
<223> OTHER INFORMATION: Synthetic

<400> SEQUENCE: 79
acatacccag agacactgag agagacagac agacagtaaa cagaggagca cgatcctatt    60
aatagtaatc aattacg                                              77

<210> SEQ ID NO 80
<211> LENGTH: 76
<212> TYPE: DNA
<213> ORGANISM: Artificial Sequence
<220> FEATURE:
<223> OTHER INFORMATION: Synthetic

<400> SEQUENCE: 80
gctcaattgt atcttatgaa aacaattttt caaaataaaa caagagatat gatcctatta    60
atagtaatca attacg                                               76

<210> SEQ ID NO 81
<211> LENGTH: 77
<212> TYPE: DNA
<213> ORGANISM: Artificial Sequence
<220> FEATURE:
<223> OTHER INFORMATION: Synthetic

<400> SEQUENCE: 81
cctgtgctga ataccgtctg catatgtata ggaaagggtt aactcagcag ggatcctatt    60
aatagtaatc aattacg                                              77

<210> SEQ ID NO 82
<211> LENGTH: 77
<212> TYPE: DNA
<213> ORGANISM: Artificial Sequence
<220> FEATURE:
<223> OTHER INFORMATION: Synthetic

<400> SEQUENCE: 82
tatgtgaatg gaaataaaat aatcaagctt gttagaattg tgttcataat gaccctagtc    60
aataatcaat gtcaacg                                              77

<210> SEQ ID NO 83
<211> LENGTH: 75
<212> TYPE: DNA
<213> ORGANISM: Artificial Sequence
<220> FEATURE:
<223> OTHER INFORMATION: Synthetic

<400> SEQUENCE: 83
gaaagtctac aattttttca gtttaaaatg gtatttattt gtaacatgta ccctagtcaa    60
taatcaatgt caacg                                                75

<210> SEQ ID NO 84
<211> LENGTH: 77
<212> TYPE: DNA
<213> ORGANISM: Artificial Sequence
<220> FEATURE:
<223> OTHER INFORMATION: Synthetic

<400> SEQUENCE: 84
caaagatgaa ggatgagagt gacttctgcc ttcattatgt tatgtgttca tatcctagtc    60
aataatcaat gtcaacg                                                  77

<210> SEQ ID NO 85
<211> LENGTH: 76
<212> TYPE: DNA
<213> ORGANISM: Artificial Sequence
<220> FEATURE:
<223> OTHER INFORMATION: Synthetic

<400> SEQUENCE: 85
cagtgaatta ttcactttgt cttagttaag taaaaataaa atctgactgt gatcctatta    60
atagtaatca attacg                                                   76

<210> SEQ ID NO 86
<211> LENGTH: 76
<212> TYPE: DNA
<213> ORGANISM: Artificial Sequence
<220> FEATURE:
<223> OTHER INFORMATION: Synthetic

<400> SEQUENCE: 86
gaacagacag gtgaatgagc acagaggtca tttgtaaacc gtttgtggtt agcctagtca    60
ataatcaatg tcaacg                                                   76

<210> SEQ ID NO 87
<211> LENGTH: 79
<212> TYPE: DNA
<213> ORGANISM: Artificial Sequence
<220> FEATURE:
<223> OTHER INFORMATION: Synthetic

<400> SEQUENCE: 87 cttttttggct tctgtgttta agttattttt ccccctaggcc cacaaacaga gtcgatccta    60
ttaatagtaa tcaattacg                                                79

<210> SEQ ID NO 88
<211> LENGTH: 74
<212> TYPE: DNA
<213> ORGANISM: Artificial Sequence
<220> FEATURE:
<223> OTHER INFORMATION: Synthetic

<400> SEQUENCE: 88
aaccttggaa aaattctgtt gtgtttagaa gcatgtacca atctatcact cctagtcaat    60
aatcaatgtc aacg                                                     74

<210> SEQ ID NO 89
<211> LENGTH: 76
<212> TYPE: DNA
<213> ORGANISM: Artificial Sequence
<220> FEATURE:
<223> OTHER INFORMATION: Synthetic

<400> SEQUENCE: 89
ctattcactg tctgtaggat gaaaaagtta ataacaccct gagaggtttc gatcctatta    60
atagtaatca attacg                                                   76

<210> SEQ ID NO 90

```
<211> LENGTH: 75
<212> TYPE: DNA
<213> ORGANISM: Artificial Sequence
<220> FEATURE:
<223> OTHER INFORMATION: Synthetic

<400> SEQUENCE: 90
ccttagatta gtttattgta tttttatca gctactataa ggtttacaca ccctagtcaa      60
taatcaatgt caacg                                                     75

<210> SEQ ID NO 91
<211> LENGTH: 78
<212> TYPE: DNA
<213> ORGANISM: Artificial Sequence
<220> FEATURE:
<223> OTHER INFORMATION: Synthetic

<400> SEQUENCE: 91
caagaccctc aaaattcaaa aatttccttt atcttgctgt agcacctcct gcgatcctat     60
taatagtaat caattacg                                                  78

<210> SEQ ID NO 92
<211> LENGTH: 75
<212> TYPE: DNA
<213> ORGANISM: Artificial Sequence
<220> FEATURE:
<223> OTHER INFORMATION: Synthetic

<400> SEQUENCE: 92
ggaggggata ggaaggggat gaggcctaac aggttgatga tctaggcttt acctagtcaa    60
taatcaatgt caacg                                                     75

<210> SEQ ID NO 93
<211> LENGTH: 77
<212> TYPE: DNA
<213> ORGANISM: Artificial Sequence
<220> FEATURE:
<223> OTHER INFORMATION: Synthetic

<400> SEQUENCE: 93
ctcaaaaagg agataattcc agcccctcgc cttaaagaat ccctatcaag tgatcctatt    60
aatagtaatc aattacg                                                   77

<210> SEQ ID NO 94
<211> LENGTH: 76
<212> TYPE: DNA
<213> ORGANISM: Artificial Sequence
<220> FEATURE:
<223> OTHER INFORMATION: Synthetic

<400> SEQUENCE: 94
cgcttgaacc tgggaggcag aggttgcagt gagccgagat cacgccgttg gatcctatta    60
atagtaatca attacg                                                    76

<210> SEQ ID NO 95
<211> LENGTH: 78
<212> TYPE: DNA
<213> ORGANISM: Artificial Sequence
<220> FEATURE:
<223> OTHER INFORMATION: Synthetic

<400> SEQUENCE: 95
ttaacttttt catcctacag acagtgaata gtaaagcttt ctgtgaagac atacccctagt    60
```

```
caataatcaa tgtcaacg                                                    78

<210> SEQ ID NO 96
<211> LENGTH: 76
<212> TYPE: DNA
<213> ORGANISM: Artificial Sequence
<220> FEATURE:
<223> OTHER INFORMATION: Synthetic

<400> SEQUENCE: 96
aaattatttc ctggtgggca atattagaat atggggaatg tttgcttctg agcctagtca     60
ataatcaatg tcaacg                                                      76
```